(12) United States Patent
Gan et al.

(10) Patent No.: US 7,037,705 B2
(45) Date of Patent: May 2, 2006

(54) ISOLATED HUMAN PROTEASE PROTEINS, NUCLEIC ACID MOLECULES ENCODING HUMAN PROTEASE PROTEINS, AND USES THEREOF

(75) Inventors: Weiniu Gan, Germantown, MD (US); Jane Ye, Germantown, MD (US); Valentina Di Francesco, Rockville, MD (US); Ellen M. Beasley, Darnestown, MD (US)

(73) Assignee: Applera Corporation, Norwalk, CT (US)

( * ) Notice: Subject to any disclaimer, the term of this patent is extended or adjusted under 35 U.S.C. 154(b) by 501 days.

(21) Appl. No.: 10/274,031

(22) Filed: Oct. 21, 2002

(65) Prior Publication Data

US 2003/0129726 A1   Jul. 10, 2003

Related U.S. Application Data

(62) Division of application No. 09/820,002, filed on Mar. 29, 2001, now Pat. No. 6,482,630.

(51) Int. Cl.
C12P 21/06 (2006.01)
C12N 9/00 (2006.01)
C12N 9/50 (2006.01)
C07H 21/04 (2006.01)

(52) U.S. Cl. .............................. 435/219; 435/4; 435/6; 435/69.1; 435/183; 435/190; 435/195; 435/212; 435/218; 530/350; 536/23.2

(58) Field of Classification Search .................... 435/4, 435/6, 69.1, 183, 190, 195, 212, 218, 219; 530/350; 536/23.2
See application file for complete search history.

(56) References Cited

OTHER PUBLICATIONS

International Search Report, Oct. 25, 2002.
Database GenBank, US National Library of Medicine, (Bethesda, MD, USA) Accession No. AAA36013, Leytus et al., Jun. 1993.
Database GenBank, US National Library of Medicine, (Bethesda, MD, USA) Accession No. CAA30558, Leytus et al., Sep. 1995.
Database GenBank, US National Library of Medicine, (Bethesda, MD, USA) Accession No. CAA30058, Leytus et al., Sep. 1995.
Database GenBank, US National Library of Medicine, (Bethesda, MD, USA) Accession No. M18930, Leytus et al., Jun. 1993.
Database GenBank, US National Library of Medicine, (Bethesda, MD, USA) Accession No. X07732, Leytus et al., Sep. 1995.
Database GenBank, US National Library of Medicine, (Bethesda, MD, USA) Accession No. X07002, Leytus et al., Sep. 1995.

*Primary Examiner*—Manjunath N. Rao
(74) *Attorney, Agent, or Firm*—Celera Genomics; Lin Sun-Hoffman

(57) ABSTRACT

The present invention provides amino acid sequences of peptides that are encoded by genes within the human genome, the protease peptides of the present invention. The present invention specifically provides isolated peptide and nucleic acid molecules, methods of identifying orthologs and paralogs of the protease peptides, and methods of identifying modulators of the protease peptides.

4 Claims, 13 Drawing Sheets

```
   1 TGGGCACCTG GTTGTTCACA CGGCAGGGGA GGAACAGCCC TGTCAACTGC
  51 TGGCCCCGGG AAACTGGGCC TGGGGAGGAC ATGCTTGGGC ATAATAAGTT
 101 AGCCCTGGGG GCAGGGCAGA GCTGGCCTCG GGCCCAGACC CTGCCGCAAT
 151 GAGGACAGGC CTGGCTGTGG CCCCAGCATG GTGTCTGTTG CAGGTGGCCG
 201 GACTGTGCCA TGCTGCTCCA GACCCAAGGT GGCAGCTCTC ACTGCGGGGA
 251 CCCTGCTACT TCTGACAGCC ATCGGGCGG CATCCTGGGC CATTGTGGCT
 301 GTTCTCCTCA GGAGTGACCA GGAGCCGCTG TACCCAGTGC AGGTCAGCTC
 351 TGCGGACGCT CGGCTCATGG TCTTTGACAA GACGGAAGGG ACGTGGCGGC
 401 TGCTGTGCTC CTCGCGCTCC AACGCCAGGG TAGCCGGACT CAGCTGCGAG
 451 GAGATGGGCT TCCTCAGTGA TTGCCCCAGA GGCCGTTTCT TGGCCGCCAT
 501 CTGCCAAGAC TGTGGCCGCA GGAAGCTGCC CGTGGACCGC ATCGTGGGAG
 551 GCCGGGACAC CAGCTTGGGC CGGTGGCCGT GGCAAGTCAG CCTTCGCTAT
 601 GATGGAGCAC ACCTCTGTGG GGATCCCTG CTCTCCGGGG ACTGGGTGCT
 651 GACAGCCGCC CACTGCTTCC CGGAGCGGAA CCGGGTCCTG TCCCGATGGC
 701 GAGTGTTTGC CGGTGCCGTG GCCCAGGCCT CTCCCCACGG TCTGCAGCTG
 751 GGGGTGCAGG CTGTGGTCTA CCACGGGGGC TATCTTCCCT TTCGGGACCC
 801 CAACAGCGAG GAGAACAGCA ACGATATTGC CCTGGTCCAC CTCTCCAGTC
 851 CCCTGCCCCT CACAGAATAC ATCCAGCCTG TGTGCCTCCC AGCTGCCGGC
 901 CAGGCCCTGG TGGATGGCAA GATCTGTACC GTGACGGGCT GGGGCAACAC
 951 GCAGTACTAT GGCCAACAGG CCGGGGTACT CCAGGAGGCT CGAGTCCCCA
1001 TAATCAGCAA TGATGTCTGC AATGGCGCTG ACTTCTATGG AAACCAGATC
1051 AAGCCCAAGA TGTTCTGTGC TGGCTACCCC GAGGGTGGCA TTGATGCCTG
1101 CCAGGGCGAC AGCGGTGGTC CCTTTGTGTG TGAGGACAGC ATCTCTCGGA
1151 CGCCACGTTG GCGGCTGTGT GGCATTGTGA GTTGGGGCAC TGGCTGTGCC
1201 CTGGCCCAGA AGCCAGGCGT CTACACCAAA GTCAGTGACT TCCGGGAGTG
1251 GATCTTCCAG GCCATAAAGA CTCACTCCGA AGCCAGCGGC ATGGTGACCC
1301 AGCTCTGACC GGTGGCTTCT CGCTGCGCAG CCTCCAGGGC CCGAGGTGAT
1351 CCCGGTGGTG GGATCCACGC TGGGCCGAGG ATGGGACGTT TTTCTTCTTG
1401 GGCCCGGTCC ACAGGTCCAA GGACACCCTC CCTCCAGGGT CCTCTCTTCC
1451 ACAGTGGCGG GCCCACTCAG CCCCGAGACC ACCCAACCTC ACCCTCCTGA
1501 CCCCCATGTA AATATTGTTC TGCTGTCTGG GACTCCTGTC TAGGTGCCCC
1551 TGATGATGGG ATGCTCTTTA AATAATAAAG ATGGTTTTGA TTAAAAAAAA
1601 AAAAAAAAAA AAAAA
   (SEQ ID NO: 1)
```

FEATURES:
5'UTR:        1 - 177
Start Codon:  178
Stop Codon:   1306
3'UTR:        1309

Homologous proteins:

| | | |
|---|---|---|
| CRA\|108000024653037 /altid=gi\|12742005 /def=ref\|XP_009324.2\| he... | 763 | 0.0 |
| CRA\|18000004924290 /altid=gi\|4504481 /def=ref\|NP_002142.1\| heps... | 761 | 0.0 |
| CRA\|18000004939616 /altid=gi\|8393560 /def=ref\|NP_058808.1\| heps... | 684 | 0.0 |
| CRA\|18000005110005 /altid=gi\|6680267 /def=ref\|NP_032307.1\| heps... | 682 | 0.0 |
| CRA\|18000004992740 /altid=gi\|899286 /def=emb\|CAA30058.1\| (X0700... | 601 | e-170 |
| CRA\|98000043610144 /altid=gi\|12832865 /def=dbj\|BAB22289.1\| (AK0... | 514 | e-144 |
| CRA\|157000140328272 /altid=gi\|13173471 /def=ref\|NP_076927.1\| tr... | 240 | 5e-62 |
| CRA\|107000045070717 /altid=gi\|12246826 /def=dbj\|BAB20078.1\| (AB... | 235 | 2e-60 |
| CRA\|107000045071722 /altid=gi\|12248777 /def=dbj\|BAB20276.1\| (AB... | 219 | 6e-56 |
| CRA\|150000075552928 /altid=gi\|9757700 /def=dbj\|BAB08217.1\| (AB0... | 217 | 3e-55 |

EST:

| | | |
|---|---|---|
| gi\|9877313 /dataset=dbest /taxon=960... | 1229 | 0.0 |
| gi\|11947931 /dataset=dbest /taxon=96... | 1023 | 0.0 |
| gi\|12945271 /dataset=dbest /taxon=960... | 920 | 0.0 |
| gi\|10288610 /dataset=dbest /taxon=96... | 866 | 0.0 |
| gi\|12271076 /dataset=dbest /taxon=960... | 761 | 0.0 |

EXPRESSION INFORMATION FOR MODULATORY USE:
gi|9877313 liver
gi|11947931 prostate
gi|12945271T cells from T cell leukemia
gi|10288610 hepatocellular carcinoma
gi|12271076 lung_tumor

FIGURE 1

```
  1 MVSVAGGRTV PCCSRPKVAA LTAGTLLLLT AIGAASWAIV AVLLRSDQEP
 51 LYPVQVSSAD ARLMVFDKTE GTWRLLCSSR SNARVAGLSC EEMGFLSDCP
101 RGRFLAAICQ DCGRRKLPVD RIVGGRDTSL GRWPWQVSLR YDGAHLCGGS
151 LLSGDWVLTA AHCFPERNRV LSRWRVFAGA VAQASPHGLQ LGVQAVVYHG
201 GYLPFRDPNS EENSNDIALV HLSSPLPLTE YIQPVCLPAA GQALVDGKIC
251 TVTGWGNTQY YGQQAGVLQE ARVPIISNDV CNGADFYGNQ IKPKMFCAGY
301 PEGGIDACQG DSGGPFVCED SISRTPRWRL CGIVSWGTGC ALAQKPGVYT
351 KVSDFREWIF QAIKTHSEAS GMVTQL
    (SEQ ID NO:2)
```

FEATURES

[1] PDOC00005 PS00005 PKC_PHOSPHO_SITE
Protein kinase C phosphorylation site
Number of matches: 4
      1    72-74   TWR
      2    78-80   SSR
      3   138-140  SLR
      4   325-327  TPR

[2] PDOC00006 PS00006 CK2_PHOSPHO_SITE
Casein kinase II phosphorylation site
Number of matches: 4
      1    46-49   SDQE
      2    57-60   SSAD
      3    89-92   SCEE
      4   365-368  THSE

[3] PDOC00007 PS00007 TYR_PHOSPHO_SITE
Tyrosine kinase phosphorylation site
          45-52   RSDQEPLY

[4] PDOC00008 PS00008 MYRISTYL
N-myristoylation site
Number of matches: 9
      1   124-129  GGRDTS
      2   143-148  GAHLCG
      3   149-154  GSLLSG
      4   188-193  GLQLGV
      5   262-267  GQQAGV
      6   303-308  GGIDAC
      7   304-309  GIDACQ
      8   337-342  GTGCAL
      9   339-344  GCALAQ

[5] PDOC00009 PS00009 AMIDATION
Amidation site
          112-115  CGRR

[6] PDOC00124 PS00134 TRYPSIN_HIS
Serine proteases, trypsin family, histidine active site
          158-163  LTAAHC

[7] PDOC00124 PS00135 TRYPSIN_SER
Serine proteases, trypsin family, serine active site
          306-317  DACQGDSGGPFV Membrane spanning structure and domains:

| Helix | Begin | End | Score | Certainity |
|---|---|---|---|---|
| 1 | 24 | 44 | 2.013 | Certain |
| 2 | 145 | 165 | 0.823 | Putative |
| 3 | 328 | 348 | 0.660 | Putative |

FIGURE 2A

BLAST Alignment to Top Hit:
>CRA|108000024653037 /altid=gi|12742005 /def=ref|XP_009324.2| hepsin
    (transmembrane protease, serine 1) [Homo sapiens]
    /org=Homo sapiens /taxon=9606 /dataset=nraa /length=417
         Length = 417

Score = 763 bits (1948), Expect = 0.0
Identities = 372/417 (89%), Positives = 372/417 (89%), Gaps = 41/417 (9%)
Frame = +1

```
Query:  178  MVSVAGGRTVPCCSRPKVAALTAGTLLLLTAIGAASWAIVAVLLRSDQEPLYPVQVSSAD  357
             M    GGRTVPCCSRPKVAALTAGTLLLLTAIGAASWAIVAVLLRSDQEPLYPVQVSSAD
Sbjct:    1  MAQKEGGRTVPCCSRPKVAALTAGTLLLLTAIGAASWAIVAVLLRSDQEPLYPVQVSSAD   60

Query:  358  ARLMVFDKTEGTWRLLCSSRSNARVAGLSCEEMGFL------------------------  465
             ARLMVFDKTEGTWRLLCSSRSNARVAGLSCEEMGFL
Sbjct:   61  ARLMVFDKTEGTWRLLCSSRSNARVAGLSCEEMGFLRALTHSELDVRTAGANGTSGFPCV  120

Query:  466  -----------------SDCPRGRFLAAICQDCGRRKLPVDRIVGGRDTSLGRWPWQVSL  594
                              SDCPRGRFLAAICQDCGRRKLPVDRIVGGRDTSLGRWPWQVSL
Sbjct:  121  DEGRLPHTQRLLEVISPSDCPRGRFLAAICQDCGRRKLPVDRIVGGRDTSLGRWPWQVSL  180

Query:  595  RYDGAHLCGGSLLSGDWVLTAAHCFPERNRVLSRWRVFAGAVAQASPHGLQLGVQAVVYH  774
             RYDGAHLCGGSLLSGDWVLTAAHCFPERNRVLSRWRVFAGAVAQASPHGLQLGVQAVVYH
Sbjct:  181  RYDGAHLCGGSLLSGDWVLTAAHCFPERNRVLSRWRVFAGAVAQASPHGLQLGVQAVVYH  240

Query:  775  GGYLPFRDPNSEENSNDIALVHLSSPLPLTEYIQPVCLPAAGQALVDGKICTVTGWGNTQ  954
             GGYLPFRDPNSEENSNDIALVHLSSPLPLTEYIQPVCLPAAGQALVDGKICTVTGWGNTQ
Sbjct:  241  GGYLPFRDPNSEENSNDIALVHLSSPLPLTEYIQPVCLPAAGQALVDGKICTVTGWGNTQ  300

Query:  955  YYGQQAGVLQEARVPIISNDVCNGADFYGNQIKPKMFCAGYPEGGIDACQGDSGGPFVCE 1134
             YYGQQAGVLQEARVPIISNDVCNGADFYGNQIKPKMFCAGYPEGGIDACQGDSGGPFVCE
Sbjct:  301  YYGQQAGVLQEARVPIISNDVCNGADFYGNQIKPKMFCAGYPEGGIDACQGDSGGPFVCE  360

Query: 1135  DSISRTPRWRLCGIVSWGTGCALAQKPGVYTKVSDFREWIFQAIKTHSEASGMVTQL    1305
             DSISRTPRWRLCGIVSWGTGCALAQKPGVYTKVSDFREWIFQAIKTHSEASGMVTQL
Sbjct:  361  DSISRTPRWRLCGIVSWGTGCALAQKPGVYTKVSDFREWIFQAIKTHSEASGMVTQL    417
             (SEQ ID NO:4)
```

HMM results:
Scores for sequence family classification (score includes all domains):
| Model | Description | Score | E-value | N |
|---|---|---|---|---|
| PF00089 | Trypsin | 289.0 | 6e-91 | 1 |
| PF01667 | Ribosomal protein S27 | 7.0 | 1.9 | 1 |
| PF01673 | Herpesvirus putative major envelope glycopro | 4.0 | 0.76 | 1 |
| CE00388 | E00388 kininogen | 3.4 | 8.1 | 1 |

Parsed for domains:
| Model | Domain | seq-f | seq-t | hmm-f | hmm-t | | score | E-value |
|---|---|---|---|---|---|---|---|---|
| PF01667 | 1/1 | 100 | 113 | .. | 1 | 14 [. | 7.0 | 1.9 |
| CE00388 | 1/1 | 120 | 171 | .. | 1 | 57 [. | 3.4 | 8.1 |
| PF00089 | 1/1 | 122 | 359 | .. | 1 | 259 [] | 289.0 | 6e-91 |
| PF01673 | 1/1 | 354 | 375 | .. | 1 | 22 [. | 4.0 | 0.76 |

FIGURE 2B

```
   1 CTGGGAATAA AATCCCTTTT CCTGTGCCAC CAGGCCTCCC CAGCTGGCCC
  51 CAGCCTTGGT TCCCACTACC TTCCCCAAGC TCTGGCCATC TGGCCATCTC
 101 GATGGCCTCT CCAGCCTCTG ACATAAGAGA GCCTGCTTAT TCTTGCCTCA
 151 AGGCCTTTGC CTGTGCTGTT CCCTCTGCCC ACAGTGCCCT TCCTTGTGGT
 201 CTGTGTGTGG CTGGCACCTC ACCTTTCAGA GCTTAGCTCA GAAGTCTCCT
 251 CTAGGGGAGG CCCTGTGATC CCTGATCCCC TGCAGAAGCC CACCTGCTGC
 301 CCCAGCCTGC ACGGTTTTCT TCACAGAATC TGCCACAATC TGGAAATTAT
 351 TGGGTTCATT TACTTGTTTC CTTGTTAATG TCTCCCACTC CCCACCTACA
 401 CGCATGAGAA CGTGAACCCC TGAGAGTCGT AACCTTATCT GTCTTCTTTG
 451 GGTTATGTTC CCGGAACCTA GAAAGGTGCC AAGCACACAG CGGATGTTCA
 501 GTAGGATGGT AAACAAATAA AGCTTCTTTA GGCTGATGAA AAAACTGAGG
 551 GTCAGGCGCG GTGGCTCACG CCTGCAATTC CAACACTTTG TTTGGGAGGC
 601 TGAGACAAGC AGATAACTTG AGTCTGGGAG TTCACGACCA GCCTGGTCAA
 651 CATGGCAAAC CCCGTCAATA CAAAAAATAC AAAAATTAGC CATGTGTGGT
 701 GGTGTGCGCC TATAATCCCA GCTACTCGGG AGGCTCAGAA TTACCTGAGC
 751 CTGAGCGCTT GAGACTGCAG TGTGCCATGA TCGCGCCGCT GCACTCCAGC
 801 CTGGGCAGCA CAGTGAAACC CTGTCTCAAA AAAAAAAAAA AGAAAAAGAA
 851 AGGAGAGAGA GAGAGAAGAA AGAAAGAAAG AAAGAAAGAA AGAAAGAAAG
 901 AAAGAAAGAA AGAAAAAAGG AAGGAAGGAA GGAAGGAAAA GAAAAAAACT
 951 GAGGCTGAGG CTCAGAGAGG GGAGGGGAGT TGCTCAGGCC CACACATCTC
1001 TGATGATTTA TAAAGCATTT ATAGAGAACT TGCTATGTGC CAGGCACTTC
1051 CGCACAGTGA GAGCCAGGAT GGCTTCGTGG CTGTACACAG GGGACCTGGC
1101 ATCAAACCTG CCCAGGGTTC TGGACGCTGC TCTGCCTCTT CCAGGCTGTC
1151 ACTGTGGGCA CGTGACCCCA CTTCTCTGAG CTATCTCAAA AACAGGAATC
1201 ATAGTTGTGG GATTGAAATA AGGACTAAAT GAGCTGATGT ATTTAGAACG
1251 GTGCTTAGCA CCTGGAGGCA TCAATACAAT TTGAGCTATT CTTCTTCTTC
1301 TTGAAAATAA CTTTAAATTA TTATTTTTAG AAGTAGGTGC TCAGTGGATG
1351 CCCATTTAAT AGATAAGAAA GTTGAGGCTC AAAGATATGA TGGCACCTGC
1401 CTTAGGTTCC AGCTAGGAAG GGGTAGGGTC AATATTTTTA AATGAGGCTG
1451 GCCAGACGCA GTGGCTCACT CCTGTAATCT CAGCATTTTG GGAGGCTGAG
1501 GAAGGAAGAT CGCTTGAGCC CAGGAGTTTG AGACCAGCCT GGGCAACATA
1551 GCAAGACCAC GTCGCTAAAA AAATTAATAC ATAAAATAAA ATGAGGCTGG
1601 CAGATTTTCA AGTGGAGGGG CAAATTTGAT CTTGCAACTG GGTACCATGA
1651 GAGAGGTCTG ATTTAGGGGG TATCTAGGGG CAAAGCATCT AGAACAGCAG
1701 AAACGACTGA GGCAGCGAGG AAATGCCAGC GGCAGGGAAG AGAGCTACCA
1751 AGAGGGCAAA GGTTGGGGGT CACAGTCCCA AGAAGAGATG GCCCAAAGCA
1801 AAGACAGAAA TACAAAAGCA CAGTGTCACT GGGGAGGAGA CATTCCCTAA
1851 GTGCCCCAAG GAAAACGTGA CAGGCGGTCG GGANNNNNNN NNNNNNNNNN
1901 NNNNNNNNNN NNNNNNNNNN NNNNNNNNNN NNNNNNNNNN NNNNNNNNNN
1951 NNNNNNNNNN NNNNNNNNNN NNNNNNNNNN NNNNNNNNNN NNNNNNNNNN
2001 AATAAGTTAG CCCTGGGGGC AGGGCAGACT GGCCTCGGGC CCAGACCCTG
2051 CCGCAATGAG GACAGGCCTG GCTGTGGCCC CAGCATGGTG TCTGTTGCAG
2101 GTGGCCGGAC TGTGCCATGC TGCTCCAGAC CCAAGGTGGC AGCTCTCACT
2151 GCGGGGACCC TGCTACTTCT GACAGCCATC GGGGCGGCAT CCTGGGCCAT
2201 TGGTGAGAGC GGTTCCTGTG CCTCTGACCT CCCCTGGCCC CTGCAGCCTC
2251 CAGCCTGCCT GCCCTCACCC CTCCCTTCTC TGCAGTGGCT GTTCTCCTCA
2301 GGAGTGACCA GGAGCCGCTG TACCCAGGTG AGTGGAGCAG GCTGGGACCC
2351 TCTGGGGGAG CCCTGGAGGA CACGTGTATC TGGCGGGAGC TCAACAAGCG
2401 TATTTGTTGA ATAAATGCAC AAATGCATGC AGAAATGCTA ATCATAATAG
2451 TGCATTTGTA TTGAGTGCCT GCTATGTACC AGGCACTATT CTAAGCACCC
2501 CACATGTCTA ACCCAGACTT TTTCAGACAC CAGTGTATTA CTCATGAGTG
2551 CCTCATAAAA TTAAATTAGT GAGTTGGAAA ACCATGTTTT TTTTTTAAGT
2601 ATGAAATAGA TTCGATTACA GACTATCACA GTACATCTCT CAGTAAGTAA
2651 AGGTTATGCT AATTTTTGTT TGTTTTTTTT TTTTTGCAT CCATATACAT
2701 GTAATCCCAC TGCATCCCCT CACTCTGAGG GTGGGACTGT TATTCTCCCT
2751 GTTTTACAGA TGGGGAAACT GAGGCTTTGA GCAATGCGGC AGTTTGCCCC
2801 AGACTACAGA GCTATGGGCT ACATCAGGAT GTAAAAATGT GTTTCTTACT
2851 GCGTGGCATG GTGAAAACAT GTTGGGGAGG CATGATATAA ATTCAGTGGA
2901 CCCTTCTAAC TCTCCTAGGA GGTAGTTTTT TGTTTGTTT GTTTTAAAAA
2951 AGAAAAAAGT CTTGCTCTGT CACCCAGGCT AGAGTGCAAT GGTGCAGTCT
3001 CAGCTCACCG CAACCTCTGC CTCCCAGGTT CAAGCGATTC TCCTGCTTCA
3051 GCCTCCCAAG TACCTGGGAA TACAGGCGTG TGCCACCATG CCCAGTTAAT
3101 TTTTTGTATT TTTAGTAGAG ATGAGATTTC ACCATGTTGG CCAGGACGGT
3151 CTCGATCTCC TGACCTTGTG ATCCACCCGC CTCACCTCTG CAAAGTGCTG
3201 GGATTACAGG CATGAGCCAC TGCGCCTGTC CCTGGTATTA GCTCCATTTT
3251 ACAGATGTGC AAAATGAGGA CCAGAGAGGA CATGCAGCTG GGAACGAGG
3301 GGCCAGGAAC AGCTCTTAGA CTTATCCACT GTAAGTGTGT CTGCAGGCAT
3351 GTGGAATGAA TGGCCACACA AATAAATAGA TAAAGAAACT AACTGTGGGA
```

FIGURE 3A

```
3401 TGAATGAATG AATCTTCCCA AATGCCAACT TCAAGCTGCC ATTCCCTGAT
3451 GCAGGACAGC AGGAAAAAAG GGGAAGTTGG GTGGTGGGAT GTATTTTCA
3501 TGTCTGTGAG CCTCATCTAA TTCCATAAAG GATTCAGTTC ACACTAAAAT
3551 CAGAAATGAA AATCCAGACA AGAAAAGCCA ACATCAACAT TAATCATCAT
3601 TACCAGCACT TAGCATTTGT ATGCACCAGC CAAGGCCTTG GGACCTTATG
3651 ATATCAACTC ATTAAGTCTT CCCAACAACC TGTTGTTTTT CTTTTCTTTT
3701 TTTTTTCTTT CTTTCTTTCT TTCTTTTTTT TTTTTTTTTT TTGAGATGGG
3751 GTCTTGCTCT GTCGCCCAGG CTGGAGTGCA GTGACACGAT CTTAGCTCAT
3801 TGTAACCTAC ATCTCCTGGG CTCAAGCAAT CCTCCCATCT CAGCCTTCTG
3851 AGTAGCTGGG ACTATAGGCT AATGCCACCA TGCCTACACA AAATTATTTT
3901 GTCAATAACA AATTATTGTT ATTTTTATCT TTTTGAGCCA GAGTCTCGCT
3951 GTGTCGCCCA GGCAGGAGTG CTGTGGCGCG ATCTTGGCTC ACTGCAATCT
4001 CCATCTCCCA GGTTCAAGTG ATTCTCCTGC CTCAGCCTCC TGAGTAGCTA
4051 GGACTACAGG CACGTGCCAC CACACCCAGC TAATTTTTGT ATTTTTAGTA
4101 GAGGCGGGGT TTCACCATGT TGGCCAGGAT GGTCTCAAAC TCCTGACCTC
4151 AGGTGATCCA CCCGTCTCGG CCTCCCAAAG TGCTGGGACT ACAGGCATGA
4201 GCCACCACAC CCAACCTCAT TTTTTAAATT TTTAGTAGAG ATGGGATCTT
4251 GCTACATTGC CCAGTCTGAT CTTGAACTCC TGAGCTCAAA GCAGTCCTCT
4301 CAGATCAGCC TCCCAAAGTG CAGGGATTAC AGGTGTGCAC CACCACAACC
4351 CATTTTCCTA TGGGGATGCT GAGGCACAGA AAGGCTGAGT GACTTGCCCC
4401 AGGTCATGGA GCTAGTCAGT GTCAGGGCTG GGATTTGAAC CCAGGCAGCC
4451 TGCGTAGTAA CTGTATATAG TGTCTACACT TGATTGCTTG TTAAAAAAAA
4501 AAAAAAGAAC AGCTGAATTC ATTGCCATAG TAAAGACTGA CATATGCCAG
4551 GCCCTGGCGG CAGCCTTTAC CCAGCAGGCC TATGAAGTTA GGGCTGTTAC
4601 ATCCCAACAT TTTGCATTTG GGGAAATTG AGTCCCAGTG AAGCAAACTG
4651 ACTTGCCCGA GGCTGACCAC ACATCAGAGA CAGAGCGAAG GGATCACGCC
4701 CCTGTCAAAA GCCCCTCCGT GACAACACGT GGCATTGAGA TAAAATCCCA
4751 ACCCATCACA GGCTCCAAGC CTCCTAGTGT GGAGGCCCCT CTCCACCCCC
4801 ACCTCACACT GGCTTCTAGC ACCCTCAGGG CCCAGTCCCT TGCTCAAATG
4851 ACCTGCTCAC ACAGAAGTCT CTACTCACCC ACTTCTTTCT AGCTCACACC
4901 CAGAGGCAGA TTTCAGTTCT GCACAGTTCC TTCTGAGCTG TGGGGCCTCC
4951 CACCAGTCCC TACTCTCTCC AAGACTCAAT TTCCTCATCT GTGAGATGGG
5001 GGTAAGAAGA ATCAGTGGGA ATAAGAGGAG ATAAAAATCT GTGTAGTACT
5051 TGGGCGGGGT GCGGTGGCTC ACCCCTGTAA TCCCAGCACT TTGGGAGGCC
5101 GAGGCAGGCA GATCACCTGA GGTCAGGAGT TCGAGACCAG CCTGGCCAAC
5151 GTGGTGAAAC CTCATCTGTA CTAAAACAC AAAAATTGGC CAGGCGTGGT
5201 GGCGGGCGCC TGTAATCCCA GCTACTCAGG AGGCTGAGGC AGGAGAACTG
5251 TTTGAACCTG GGAGGCGCGG GTTGCAGGTT GCAGTGAACT GAGATCACGC
5301 CACTGCACTC CAGCCTGGGT GACAGAGCAA GAGTCTGTCT CAAAAAAAAA
5351 AAAAAAAAAA AGGCTGTGCA GTACTTGCCT CTTAGCCAGC ACAGTGGACA
5401 TTGGCTTTTG TATCTCACTC CTGAAATTCT TTCTTGAAAT TCTTGAGCA
5451 AGATCTTCCT GGACTTCCAG ACTCTATGGC CTCTCACCCT ATGGTGTGTC
5501 CCTGCCACCC CGGTAAAACC CTCCTCACTC ATTGTGAATT ATTTACTCCT
5551 GGCGAACTCC AGGAAGGCAG GGACCTTTTG TGGTCAGACG GTGCCTGGCA
5601 CATAGTAGGT TCTCAGGAAA TCCTTGAGTT ATGAGTGCAC CCAAAGCCAA
5651 AACACTGGGA TGAACTAGAG AGTCATGGGC CTCCAGCTGG AAAGGAGCGA
5701 GGCCACCACT CACAACCGGC TCTGGCCAGC ACCACGCCGC CACCCTGCAG
5751 AGGTATTTGG GTTTTTCAAC AACTCAGGGA AATGATGAAA CAAACAAACA
5801 AACAAAAACA ACCCCAAGCT TGTATCCCCA CCTCGCTTTT TTTTTCCTGG
5851 GATTTTCACA CTTCTAAATA TATCCAACAA CTTGGCAGGC ACACCAGGTG
5901 ACCCAGAACA TCCTTTTTGT GTTGCCTGAA ATGATAGGAA CAAGAATAAA
5951 GAATTTAAAA GTGAGAAACA GCAGCAGAGA GTGTGACTTT AAAAATAGCC
6001 AGAGGGGACA TTTGATGTTC TCTCCCCACT CCCATCTCCC CCAACACACA
6051 TCTATAAAGT GATTTTCCCC CCTAAAACCT CACACTTTCT GGAAATCACA
6101 TTTCCAGAGC AGTTAACAGT CATTTTAAAA TAAGAATCCA CCCCTCTTCC
6151 TGCCCCAGCT GGTGTTTCAA ACTCCAAGCC TTGGCTTTCA TGGGGTGATG
6201 AGGACCCCCC AGCTAGAGGT GCCAGGCATT CCCTGCCCCA ACCCCAGAGC
6251 AGGAGACCGT AATTAAGGCA GGCCAGGCCG GTGCGGTGGC TCACGCCTGT
6301 AATCCCAGCA CTTTGGGAGG CCCAAATGGG CAGATCACTT GAGGTCAGGA
6351 GACCAGCCTG GCCAACATGG CAAAACCCCA TCTCTACTAA AAATACAAAA
6401 ATTAGCCGGG CGTGGTGGCT GGTGCCTGTA ATCCCAGCTA TTTGGGAGGC
6451 TGAGGCATGA GAATCGCTTG AACTCAGGAG GCAGAGGTTA CAGTGAGCTG
6501 AGATCGTGCC ACTGCACTCT AGCCTGGGAG ACAGAGCAAG ACTCCATCTC
6551 AAAACAAACT TAAAATAGAA TAAAAATCCG CCCCCTCCC
6601 CGCCCCAGTT GGTGTTTCAA ACCCTGAGAC TTGGCCTTGG AATTCATGGG
6651 GTGATGAGGA CCCCACAGCC AGAGGTGCCA GGCGTTCCCT GCCCCAACCC
6701 CAGAGCAGGA GGCCATCATT AAGGCAGGCC AGCCAGGTGG CTTTTCAGTG
6751 CCAGCCGTAG CTGAATATAT TAGGCAGGGA GACAGGCAAG GGTTTGTATG
```

FIGURE 3B

```
6801 AGACCCACAG AAGGAACAGG GAATATGCTG GTCTGGGTTC AAGTCCCGGT
6851 TTTGCTGGTT AGCCGTGTGC CTCTGGGCAA GTTTATTCCT CTGAGGCTTA
6901 GTTTTCCCAT CTGTAAGATG GGCATAGAAG TGGTCACTAC TGGCTGGGCA
6951 CAGTGGCTCA CGCCTGTAAT CCCAGCACTT GGGGAGGCCA AGGCAGGTGG
7001 ATCACCTGAG GCCAGAAGTT CGAGACCAGC CTGGCCAACA TGGTGAAACG
7051 CTGTTTCTAC TAAGAACACA AAAGTTAGCC AGGTGTAGTA GCATGTGCCT
7101 GTAATCCCAG CTACTCGGGA GGCTGAGGCA GGAGGATCGC TTGAACCTGG
7151 GAGGCAGAGG TTGCAGTGAG CCGAGATCAT GCCACTGCAC TCCAGCCTGA
7201 GCAACAGAGC AAGATTATGT CTCAAAAAAA AAAAAAAAAA CCGAAGTGGT
7251 CACTATCTCC GAGGATGGTT GTGGGATTCA GAGAGCCACT TGGATAGGAT
7301 GCATAGCATG GGGCCAGCCC ACTGACACCC CCCAGTAAAC GTAGCCAGTG
7351 CTATTATTAC TGTGCTGTTG TTTAACCCTC CAGAGGGGAA GTCTCTTGAG
7401 AGGCTGTCCA GGGCAATGTT AAAAGCTTGG GGTTTGAAGT CACTCAGACC
7451 TGATTTCGAA TCCTCTCTCC CTGCTTCTCG TGCATTTGGT GACGTTGGGG
7501 AAGCCACCCC ACCTCTCTGA GCCTCAGCTT CCCCGTCTGG AATTTGGGGA
7551 TGATCTTCGT GGCTCCTGGG GTGTGCGACG AGGCCTTGGT TGATGGTGGG
7601 GCAGAGGTAG CCTAGCCCCA GGAACACAGT AGGTCCTCAG CTGGGGAGAG
7651 TTCTACTTGG AAGTCTTGCT TCTCCTTGTC CCAACCTGCG GGGCTGTGGG
7701 AAGACCCCTC AGCTGGTGTG TGGCCTCACC AGGTTCCTTC TAAGAGGATG
7751 CAAAAGCAAG TTTTCATTTG ACTCGGTTTC CCAGAATGTG CTCTCAGAGC
7801 CCAGGCCAGG CAGGAGGCTC TTGAGAAAAG GACAAAAGA CATGGTGGCT
7851 CACACCTGCC ATCCCAGCAC TTTGGGAGGC CAAGGTGGGA GGATTGCTTG
7901 AGGCCAGGAG TTTGAGATCA GCCTGGACAA TATAGCAATA CCCTGTCTCT
7951 ACAGAAAAAA ATAAATTTAA AAGGCGTTTT TAGCTCAGGC TTTGCTGGGT
8001 TCTAACCTGG CTATTGTCAC TCAGCTTTAT CCTAACATAA AAAAATAAAC
8051 AAATTAGCAG GGTGTGGTGG TATGCCCCTG TGGTCCTAGC TACTTGGGAG
8101 GTTGAGGCGG GAGGATCGTT TGAGCCCAGG AGGTTGAGGC TGCAATGAGC
8151 TATGATCGTG CCACTGCACT CCAGCCTGGG TGGTGGAGCG AGACCCTGTC
8201 TCAAAAAAGA AAAAAAAAAA GTGGCAGGGA GAAGGAAAGG AAAGGACAAA
8251 GAGGTTCACA GCTGATCTCT CCCTGAACCT GCTCCTTCCG TCCCCATCTC
8301 TGTCAGCCCC ATCTTTTCAG GCTCAGGCCA AACCCCTCGG TTACCCTCCC
8351 AGTTCCTCCA GTCACCCATG AATCAGATCT TGCAGGAAAC CCTGTCAGCT
8401 GCACCTACAG AACCTCTCCA AAATCTGAAC TCTTCTCCCC GTCCACTGCC
8451 CCCACCCTGC TCCAGCCCCC TTCCCCTCCC CTCTGGACAT CCCAGAGCCT
8501 CCTCCCTGGC CTCCCTGCTC CCATCCCTGC CCCCAATCA TATCCCACAA
8551 AGGGGATATG ACTCACTCAC TTAACCGGCA ATTCTGGAGG GTCTTAAAAC
8601 CTGGCTGCCT CAAGAGGCTT TAAAATGTTA TCAGATGGGG GCCAGGTACA
8651 GTGGCTCATG CTGGTTCCCC ACTTGCAGCC AGAGGGAGCT GGTGACCACC
8701 TGAGTCAGGT CAGGGCCCTC CCCTGGCTGC ACCTCACACC AGGTGCCAGC
8751 AAAGCCCTGA TGTTGCTCTA TTTCTAGCTC CCACCTGATC TGCCCCTCCC
8801 TGGCTCACTC TGCTCTGGCC TCCCACTGTT CCTGGAGCAC TCCCCCCAGT
8851 CCCCCACACC AGCCTTGGGA TCTTTGCATC TGCAAGTCCC TCTGTCTCCG
8901 TGCTGATCTC ACACACCTCC TGACACTTTC TCACCTCCTG CAGGTCTTTG
8951 TTCCTGCACC ACCTTCCCAG GGACGCTCTC CTTGCAGCGA CTGAAAAGTG
9001 CAACCTCACC CCACCCTCCA CACCGGCACT CCCCTCCCTC GGTGGCATTT
9051 TATTTTTCTC TGTGGCCCCT TCCTATCTTG TGACACATAA TATATCCTAC
9101 TTATTTGTCC CTTTCTTGAT TTGTCTCACC TACTGAGCTT TGAGTTCCAC
9151 AGGGGTCGGG GTTTTTGTCT GATTTGTTCA TTGCAGTGGT TTGTTGTTCA
9201 CTGCCTAAAA TAGAGCCTGG CAGGTACAAA GTGTTTGGTA AATAGAAATC
9251 AATACCCCAG GGTCTGTGAC CTGACTTAGG TGTTAACAGG TTCCTCTGAG
9301 GTGTGTGGGG AACAGACTGA GGGGTTTCAG GGGACATCTG TTCTCACCAC
9351 AAATTGCCCC CCAACCAGCC CCAGACATGA ACAGTCTCCC GGGAGCTCCC
9401 TCTAGCCTTC TCGTATATCC CAGCCCTGCC TCATGTCACA ATTTGTAATG
9451 ATGTGTTTGG CTGGGTGACA TTTTATGGCC ATCTGTCTCC CTATCCCCTA
9501 TAATGTGGTT TGCCGAAAGC AAAGCCCAGG ACTGTCTCGG CCATCTGTGT
9551 CTCCAGGATC ACCCCTCACT GGGCATGGAG TATGTGTCCA GTTAACGCTT
9601 GCTGAGTGAA TGAATGAATA CTCCATCCTC TGCCTGGAGA ATTACGCACT
9651 TTAGCATATC CAAGGCTCTG ACAAGTCCTG CATAAAAGAG CATTATTGTT
9701 TTCTTTCTTT CTTTCCTTCT TTCCCTCTTC TTTTCTTTCT GACTATAGGA
9751 TATTGATTAT CAATCTGGCA ATAGTCAAGA TTGGCAGTCT GGTGTATTAG
9801 TCAAAGGTTT TCAGCCTACA AAAGACAAAA AGAAAAAATA AACTGGCTAA
9851 AAACAAAAGG GGATATGATT TACTAACTCA CTTAACCGAC AGTCACAGAG
9901 GTTCTTCAAA CCTGCTGTA TCAAGGGGCT TTAAAATGTT ATCAGATGGG
9951 GGCCAGGTGC AGTAGCTCAC GCCTGTCATC CAGCACTTTG GGAGGCCAAG
10001 ACAGGCAGAT CACTTGAGGT CAGGAGTTCG AGACCAGCCT GGCCAACATG
10051 GTGAAACCCC GTGTCTACTA AAAATACAAA AAATTAGCCA GGTGTGGTGG
10101 CATGTGTCTG TAGCTCCAGC TACTCGGGAG GCTGAGGCAG GACAATGGCT
10151 TGAATCCGGG AGGCGGAGGT TACAGTGACC CAAGGTTGCA CCAGTGCATT
```

FIGURE 3C

```
10201 CCAGCCTGGG TGACAGAGCG AGACTCTGTC TCAAAAAAAA AAAAAAAGTT
10251 ATCAGATGGG AAATGAATTC CGATATTAAA AATTGATATG TATTTATACT
10301 ATATTATTAA AGTTATTTTT CATAAAACAT AGAAGGGTAA GTTTAAGAAA
10351 TGAGAAGTAT TTATACCAAA ATGATTAAAT ATTATTTAAT TTAAAGATAT
10401 AAATGTCTTG TTGGACAAAT AATTCAAAAT TTCCATTAGA CAGGAAAAAT
10451 AAGTTCAAGA GATATATTGA ACAACATGGT GATTATAGTT AATAACAATA
10501 TATTATATAC TTGAACATTG CTAAAAGATA TTTTAAGTGT TCTCACCACA
10551 CACAAAGGGT AGTGCATGTG TTAATTAGCT TGATTTAGCC GTTCCACAAC
10601 GTATACATAT TTCACATCAT CTTGTACACC ATCAATGTAT ATAATTTTGT
10651 CAATTAAAAT AAATACATAT TTTAAGGCCG GGTGCAGTGG CTCACACCTA
10701 TAATCGCAGC ACTTTGGGAG GCCGAGGCAG GCAGATCACC TGAGGTCAGG
10751 AGTTTGAGAC TAGCCTGGCC AACATGGTGA AACCCCATTC TCTACTTAAA
10801 ATACAAAAAA ATTAGCTGGG CATGGTGGTG CATGTCTGTA ATCCCAGCCA
10851 CTCGGGAGGC TGAGGCAGAA GAATCGCTTG AACCCGGGAG GCAGAGGTTG
10901 CAGTGAGCTG AGATTGCACC ACTGCACACC AGCCTGGACA ACAGAAGTGA
10951 GACTCCGTCT CAAAAAAATA AATAAATAAA AATAAAATAA ATACATATAT
11001 ATTTTTGAGA TGGAGTCTCA CTCTGTCGCC CAAACTGGAG TGCAGTGGCA
11051 CGATCTTGGC TCACTGCAAC CTCTGCTGCC CAGGTTCAAG CAATTCTCCT
11101 GCCTCAGCCT CCCGAGTAGC TGGGATTACA GGCACCTGCC ATCATGCCTG
11151 GCTAATTTTT GTAGTTTTCA TAGAGACGAG GTTTCATCAT CTTGGCCAGG
11201 CTGGTCTTGA ACTCCTGACC TTGTGATCCA CCCATCTCGG CCTCCCAAAT
11251 AAATACATAT TTTAAAAGAT AGAAATCACT CTGGAAGGAG AGTTAATCTG
11301 TTTGATATAA TAATAATATA TTAATATTAT ATTATAACAA TATATTAGTA
11351 TTATATTCTA ATAATATATT AATATTATAT TATAATAATA TATTATTATA
11401 TTATAACAAT ATATTAATAT TATATTATAA CAATATATTA ATATTATATT
11451 ATGTAATAAT ACTACTACTC CATATAGCTA TGGAAAAGTT CATATGAAGA
11501 AACCAGGCTA TGATCTACAA ACTGGCAACA AATTTGTTCT TCTATTTTCC
11551 ATATGCTGTC TGTGTACGTA TAAAGTGAGA GGTCTTTTTA TATGAGTTAA
11601 GGGTGTGACC AAAGACAAAT GGAAAAAGAC AAATGACAAA CATACTAATA
11651 AAGAGCTTCG GTTTCTCCAC AAAAAATACA ATAATAAAAT AAAATGTTAT
11701 CAGAAATCTC TTGACTCTCC TCCACGTTAG CTCACTTTTT CCCTCAAGAG
11751 GGTGAACATG ACCCTTAACA GATCCAGCCT CAAGTGCTGG ATTCTCTTGG
11801 GAACTTGGTT AAATGGTTTT TTTTCTTCCC GAATGTCCAA GTCACCTTCC
11851 AGACCTGCAG CTCCTGAGCA GCCAACTTAG GACTTCTAAT GGAGAGTGAA
11901 GTTCCCCTGG TTCGCGGAGG GGCCGGCCAC AGCCTCAAGG CTGCTGTTGA
11951 TTGGTCCGAC CTGAGTCCTT GAGTCTGGCA GAGTGCCATG GTGCTCTGTA
12001 ATCCCACCTG TAATCCCAGC ATTTTAGGAG GCAGAGGCAG GAAGATTGCT
12051 TGAGCCTAGG AGTTCAAGAC CAGCCTGGGC AACATAGCAA GACCCGTCTC
12101 TACAAAACAA AACAAAACAA AACAAACAAA CAAAAAAATT AGCCAGGTGT
12151 GGTGGTGCAC GCCTGTGGTC CTAGCTACTC AGGAGGTTGA GGTAGGAGGA
12201 TTTCTTGAGT CTGGGAGGTC AAGGCTACAG TGAGCCAAGA TCACACCACT
12251 ACACTCCAGC CTGGGCAACA GAGCGAGACC CTGTCTTTAA AAAAAAAAAG
12301 TCCTTGAGTC ATGATTCCAG ATGCAATCGC AGATGTGGGG GCTGCAACCC
12351 TCCGATGGGC TGGGGTTCAC GTCTACACCA CATGGCTGGA GCACAGGCCA
12401 GGAGGGGCTC CGGCTGGGGA AGCATGTGGG GAGCCTGGCT GTGGGACCCA
12451 GGCGGCCCCG GGCCCTGTCG CCCTGCAGTG CAGGTCAGCT CTGCGGACGC
12501 TCGGCTCATG GTCTTTGACA AGACGGAAGG GACGTGGCGG CTGCTGTGCT
12551 CCTCGCGCTC CAACGCCAGG GTAGCCGGAC TCAGCTGCGA GGAGATGGGC
12601 TTCCTCAGGT ACTGGGGGCC CTCGGAGGGG TGGGAGCCGG GAGGGGCTGG
12651 GGAGCAGGCC TAACCCCTGC CCCGCCCAGG GCACTGACCC ACTCCGAGCT
12701 GGACGTGCGA ACGGCGGGCG CCAATGGCAC GTCGGGCTTC TTCTGTGTGG
12751 ACGAGGGGAG GCTGCCCCAC ACCCAGAGGC TGCTGGAGGT CATCTCCGTG
12801 TGGTGAGGAG GGCAGCGGGC AGGTGGGGCA ACACCTCAGA CCCCCAAGGC
12851 ACTCCCTCTC CCCGTTTTCC TTCCACCTGT CTTAACTGGT CTCTATTTCC
12901 TTTCTTTCTG TGTCTCCAAT CCCATCTCTC CCAGTGATTG CCCCAGAGGC
12951 CGTTTCTTGG CCGCCATCTG CCAAGGTGAG ATCCTAAAAC TCAGAACCCT
13001 CTCCTTTAGG CCCTTGGGGA GGCCACGTCC CCTCAAGCTC CCCAGGATGG
13051 GGCCATGTAC TTTCAGACCC CCTAGGGCAG GGCCAAGCCT GGGCTCTGGG
13101 GACCTGGGCT CCAGTCCCCT GTCGCCGCCC CCTGCTGACC CTTGTCCCAC
13151 AGACTGTGGC CGCAGGAAGC TGCCCGTGGA CCGCATCGTG GGAGGCCGGG
13201 ACACCAGCTT GGGCCGGTGG CCGTGGCAAG TCAGCCTTCG CTATGATGGA
13251 GCACACCTCT GTGGGGATCC CTGCTCTCC GGGGACTGGG TGCTGACAGC
13301 CGCCCACTGC TTCCCGGAGT GAGTGCCCCC CAATGGCGCT GATGATGGGG
13351 AGGCAGAGGA GCGGAGAGAC AGTGGGGAGG AGGGCGGATT GTGCCCAGGC
13401 AGGTGGCCAC CCTCCACCCC TTTCCCTGGT AGGCGGAACC GGGTCCTGTC
13451 CCGATGCGA GTGTTTGCCG GTGCCGTGGC CCAGGCCTCT CCCCACGGTC
13501 TGCAGCTGGG GGTGCAGGCT GTGGTCTACC ACGGGGCTA TCTTCCCTTT
13551 CGGGACCCCA ACAGCGAGGA GAACAGCAAC GATATTGCCC TGGTCCACCT
```

FIGURE 3D

```
13601 CTCCAGTCCC CTGCCCCTCA CAGGTAAGTC TAAGGGCTGA GCCATGGGGC
13651 TTGAGGACCC GAGGCCAGGA GGACAGAGGA GGGGACCAGG GGCACAAGGC
13701 AATCAACTTA TGGCTCAGGC ATCCTTGGCA ATAAGGGGAA TGATCTCGAG
13751 GGAGCACAAA GTGGGCCTTA ACTATCAATG ATCAGTGCAG CCAATTTGGA
13801 AAATTTGCCA GCATTTCCCC AAGAAGTATA CATAAAGTTA CCATTGGACC
13851 CAACACTTCC ACTCCCAGGA CAGGAGGTAT ATACCTAAGA CAAATGGAAA
13901 CTGTGTCTGC ACCAAAACTC GTACATCAGT GTTCATAGCA GCATTATTCA
13951 TAATAGCCCA AAGATGGAAA CAGCCCAAGA GTGTTTCATC GGACAAATGC
14001 ATAAAGAAAA TGTGGTATAT TGACCGGGCG CGGTGGCTCA TGCCTGTAAT
14051 CCCAGCACTT TGGGAGGCCG AGGTGGGTGG ATACACGAGG TCAGGAGTTT
14101 GAAACCAGCC TGGCCAACAT GGTGAAACTC CTCTCTACTA AAAATACAAA
14151 AATTAGNNNN NNNNNNNNNN NNNNNNNNNN NNNNNNNNNN NNNNNNNNNN
14201 NNNNNNNNNN NNNNNNNNNN NNNNNNNNNN NNNNNNNNNN NNNNNNNNNN
14251 NNNNNNNNNN NNNNNNNNNN NNNNNNNNNN NNNNNNNNNN NNNNNNNNNN
14301 NNNNNNNNNN NNNNNNNNNN NNNNNNNNNN NNNNNNNNNN NNNNNNNNNN
14351 NNNNNNNNNN NNNNNNNNNN NNNNNNNNNN NNNNNNNNNN NNNNNNNNNN
14401 NNNNNNNNNN NNNNNNNNNN NNNNNNNNNN NNNNNNNNNN NNNNNNNNNN
14451 NNNNNNNNNN NNNNNNNNNN NNNNNNNNNN NNNNNNNNNN NNNNNNNNNN
14501 NNNNNNNNNN NNNNNNNNNN NNNNNNNNNN NNNNNNNNNN NNNNNNNNNN
14551 NNNNNNNNNN NNNNNNNNNN NNNNNNNNNN NNNNNNNNNN NNNNNNNNNN
14601 NNNNNNNNNN NNNNNNNNNN NNNNNNNNNN NNNNNNNNNN NNNNNNNNNN
14651 NNNNNNNNNN NNNNNNNNNN NNNNNNNNNN NNNNNNNNNN NNNNNNNNNN
14701 NNNNNNNNNN NNNNNNNNNN NNNNNNNNNN NNNNNNNNNN NNNNNNNNNN
14751 NNNNNNNNNN NNNNNNNNNN NNNNNNNNNN NNNNNNNNNN NNNNNNNNNN
14801 NNNNNNNNNN NNNNNNNNNN NNNNNNNNNN NNNNNNNNNN NNNNNNNNNN
14851 NNNNNNNNNN NNNNNNNNNN NNNNNNNNNN NNNNNNNNNN NNNNNNNNNN
14901 NNNNNNNNNN NNNNNNNNNN NNNNNNNNNN NNNNNNNNNN NNNNNNNNNN
14951 NNNNNNNNNN NNNNNNNNNN NNNNNNNNNN NNNNNNNNNN NNNNNNNNNN
15001 NNNNNNNNNN NNNNNNNNNN NNNNNNNNNN NNNNNNNNNN NNNNNNNNNN
15051 NNNNNNNNNN NNNNNNNNNN NNNNNNNNNN NNNNNNNNNN NNNNNNNNNN
15101 NNNNNNNNNN NNNNNNNNNN NNNNNNNNNN NNNNNNNNNN NNNNNNNNNN
15151 NNNNNNNNNN NNNNNNNNNN NNNNNNNNNN NNNNNNNNNN NNNNNNNNNN
15201 NNNNNNNNNN NNNNNNNNNN NNNNNNNNNN NNNNNNNNNN NNNNNNNNNN
15251 NNNNNNNNNN NNNNNNNNNN NNNNNNNNNN NNNNNNNNNN NNNNNNNNNN
15301 NNNNNNNNNN NNNNNNNNNN NNNNNNNNNN NNNNNNNNNN NNNNNNNNNN
15351 NNNNNNNNNN NNNNNNNNNN NNNNNNNNNN NNNNNNNNNN NNNNNNNNNN
15401 NNNNNNNNNN NNNNNNNNNN NNNNNNNNNN NNNNNNNNNN NNNNNNNNNN
15451 NNNNNNNNNN NNNNNNNNNN NNNNNNNNNN NNNNNNNNNN NNNNNNNNNN
15501 NNNNNNNNNN NNNNNNNNNN NNNNNNNNNN NNNNNNNNNN NNNNNNNNNN
15551 NNNNNNNNNN NNNNNNNNNN NNNNNNNNNN NNNNNNNNNN NNNNNNNNNN
15601 NNNNNNNNNN NNNNNNNNNN NNNNNNNNNN NNNNNNNNNN NNNNNNNNNN
15651 NNNNNNNNNN NNNNNNNNNN NNNNNNNNNN NNNNNNNNNN NNNNNNNNNN
15701 NNNNNNNNNN NNNNNNNNNN NNNNNNNNNN NNNNNNNNNN NNNNNNNNNN
15751 NNNNNNNNNN NNNNNNNNNN NNNNNNNNNN NNNNNNNNNN NNNNNNNNNN
15801 NNNNNNNNNN NNNNNNNNNN NNNNNNNNNN NNNNNNNNNN NNNNNNNNNN
15851 NNNNNNNNNN NNNNNNNNNN NNNNNNNNNN NNNNNNNNNN NNNNNNNNNN
15901 NNNNNNNNNN NNNNNNNNNN NNNNNNNNNN NNNNNNNNNN NNNNNNNNNN
15951 NNNNNNNNNN NNNNNNNNNN NNNNNNNNNN NNNNNNNNNN NNNNNNNNNN
16001 NNNNNNNNNN NNNNNNNNNN NNNNNNNNNN NNNNNNNNNN NNNNNNNNNN
16051 NNNNNNNNNN NNNNNNNNNN NNNNNNNNNN NNNNNNNNNN NNNNNNNNNN
16101 NNNNNNNNNN NNNNNNNNNN NNNNNNNNNN NNNNNNNNNN NNNNNNNNNN
16151 NNNNNNNNNN NNNNNNNNNN NNNNNNNNNN NNNNNNNNNN NNNNNNNNNN
16201 NNNNNNNNNN NNNNNNNNNN NNNNNNNNNN NNNNNNNNNN NNNNNNNNNN
16251 NNNNNNNNNN NNNNNNNNNN NNNNNNNNNN NNNNNNNNNN NNNNNNNNNN
16301 NNNNNNNNNN NNNNNNNNNN NNNNNNNNNN NNNNNNNNNN NNNNNNNNNN
16351 NNNNNNNNNN NNNNNNNNNN NNNNNNNNNN NNNNNNNNNN NNNNNNNNNN
16401 NNNNNNNNNN NNNNNNNNNN NNNNNNNNNN NNNNNNNNNN NNNNNNNNNN
16451 NNNNNNNNNN NNNNNNNNNN NNNNNNNNNN NNNNNNNNNN NNNNNNNNNN
16501 NNNNNNNNNN NNNNNNNNNN NNNNNNNNNN NNNNNNNNNN NNNNNNNNNN
16551 NNNNNNNNNN NNNNNNNNNN NNNNNNNNNN NNNNNNNNNN NNNNNNNNNN
16601 NNNNNNNNNN NNNNNNNNNN NNNNNNNNNN NNNNNNNNNN NNNNNNNNNN
16651 NNNNNNNNNN NNNNNNNNNN NNNNNNNNNN NNNNNNNNNN NNNNNNNNNN
16701 NNNNNNNNNN NNNNNNNNNN NNNNNNNNNN NNNNNNNNNN NNNNNNNNNN
16751 NNNNNNNNNN NNNNNNNNNN NNNNNNNNNN NNNNNNNNNN NNNNNNNNNN
16801 NNNNNNNNNN NNNNNNNNNN NNNNNNNNNN NNNNNNNNNN NNNNNNNNNN
16851 NNNNNNNNNN NNNNNNNNNN NNNNNNNNNN NNNNNNTTGC CACACCCTTC
16901 TCCTTAGTGA AAAGTAGTGA GAGAGTTAAT ATTGAAGTAA GGACGCATCT
16951 TTGAGGACAG GTGGACAGGT GGAAGCGGCT GGGATTTCAG ACACAGGGCT
```

FIGURE 3E

```
17001 GAGGGGGTCA CAGCATGGGC TTTGGGGTCA GATTCAGATA TTTGCCAACT
17051 GTGTGATCTT GGACACATGA CTTCACCTCA CCGTGTCTCA GTTTCCCTTA
17101 TCTGTAAAAT GACTTCCTAG GGTTATTGAG ACAATTAAAA GGGTTAATAT
17151 GAGTAAAGAG CTTAGAGAAC TGCCAGCACA TAGTGAACAC TGGTAAATGT
17201 TAGCAATTGC TACTATTGTT GTTTAATACT TTTACTAGTT ATATGAACAC
17251 TTGCTGTTTG CCTGGCATGC AACTCAATGA CTCACCAATT TCTCACTACA
17301 ACTTCTGGGG ATAAGTGATT ATTATTTCCA TTCTACATCT GAGAGCTCTA
17351 AGACTCAGGC AGGTGATGTC ATCAGCAGGC AGCAGGCAAC AGGCAGGGCT
17401 GCCAGGAACC CTTGCATAGG TTGTGCACTG CACAAGGACA CCACATCTCA
17451 GGGTTACCAC TCTCTCTGTA GACCTGTGTA TTTATTATTA TGATTTTCTG
17501 CCAGGTGGAA GTCAAATGTC TCAAGATAGG AGTGTCTCTC TCTCTCTCTC
17551 TCTTTCTTCT CTCTCTCTCT TTCTTTTTTT GAGACAGAGT CTTGCTCTGT
17601 CACCCAGGCT GGAGTGCAAT GGCGCAATCT CGGCTCCCTG CAAACTCTGC
17651 CTCCTAGGTT CAAGCGATTC TCCTGCCTCA GCCTCCTGAG TAGCTGGGAT
17701 TACAGGCACC TGCCATCTGT AATCCCAGTG CTTTGGGAGG CTGAGGCAGG
17751 AGGATTGCTT GAGCCCAGGA GGCCGAGGCT GCAGTGAGCC ATGTTCCTGC
17801 CACTGCACTC TGGCCTGGGT GACACTGCAG GCTTAGAAAT GAAAACAAGC
17851 TGTGTTAAAA CATACATGTT ATGAAACTTT GGACACGTGA CTTGGCCTCA
17901 TTTTCCCCCT CTCTAAAATG GGATAATATA GACCCTACCT CTCTGGGCTG
17951 ATGAAACATT AAAGAAAATG GTGCAGGAAG GCGCCTAGTA TGCGATGAGC
18001 TCTTGGTACG TGGCGACTTC CGTTGTGGCT TTTTTGTTTG TTTGTTTGTT
18051 TTTGAGACAG AGTCTTGCTC TGTCGCCCAG GCTGGAGTGC AATGACATGA
18101 TCTCGGCTCA CTGCAACCTC CACCTCCTGG GTTCAAGTGA TTCTTCTGCC
18151 TCAGTCTCCC GAGTAGCTGG GATTACAGGT GCGTGCCACC ATGCCCGGCT
18201 AATTTTTGTA TTTTTAGTAG AGATGAGGTT TCGCCATGTT GGCCAGGCTG
18251 GTCTCAAACT CCTGACATCA AGTGATCCTC CTGCCTCGGC CTCCCAAAGT
18301 GCTGGTATTA CAGGCATGAG CCACTGTGCC CAGCCTATTG TGGTTTTTTT
18351 TTTAAAGAAC AGAGAGGGCA GGGTGTGTTA GGGGCCATGG TAGCAGCTGG
18401 ACAGAGGTTT GTACCAGGTG GGGCAGGCCA GCAGGGGCTG GACCAGCATT
18451 GTCTCTCTCA CAGAATACAT CCAGCCTGTG TGCCTCCCAG CTGCCGGCCA
18501 GGCCCTGGTG GATGGCAAGA TCTGTACCGT GACGGGCTGG GGCAACACGC
18551 AGTACTATGG TGAGTCCTGT CCTCTGCCTC TGATGCCACC ATTTGGGAGA
18601 CTCTGAACTG GGCTGGGGAT GGGCAGTCTG GCTGGTTGGA TGAGTCTTGA
18651 CCATGAGGAG TAGGGATGCT GAGGGGAATG GGGTGGGCAC CAGGAGGGAA
18701 GGGGGGTGTG TACACCCCCC AGCTCTGGCC AGCCTTGCCT GCACACCCCC
18751 AGGCCAACAG GCCGGGGTAC TCCAGGAGGC TCGAGTCCCC ATAATCAGCA
18801 ATGATGTCTG CAATGGCGCT GACTTCTATG GAAACCAGAT CAAGCCCAAG
18851 ATGTTCTGTG CTGGCTACCC CGAGGGTGGC ATTGATGCCT GCCAGGTGAG
18901 GGACTCTGTA GGGGCAGCCC CCTGGTCGCT GCCACCCCAG GGATGGAGAC
18951 GCAGGGGAGT GGGTGGTCGG GCTCCCCATC TAAAAGCCTG AGGGCTCTGG
19001 GGCCACAGCC CATGTCATCC CGGGGGGGCC TCCTGTCTAA CCACTTTGGC
19051 CTCCAGCCAG ACCTCCCTCT CCCCTCCCAG GGCGACAGCG GTGGTCCCTT
19101 TGTGTGTGAG GACAGCATCT CTCGGACGCC ACGTTGGCGG CTGTGTGGCA
19151 TTGTGAGTTG GGGCACTGGC TGTGCCCTGG CCCAGAAGCC AGGCGTCTAC
19201 ACCAAAGTCA GTGACTTCCG GGAGTGGATC TTCCAGGCCA TAAAGGTGAA
19251 AGTTGGGTCC AGATGGGAGC CAGGGTGGGG ACGTTTGGGT GTCTAATGGG
19301 GGAAGGGAGG CAGAGATTTG TTTTAGGAAA CCTACGCTCA GGCCTAGAAG
19351 AGGGCCCCCC TTGGGAACAG ATGGACTTTG AAGGGTTCCT GGGGAAGGGA
19401 AGCCAGTGGT GGGACGTGGA AGCCTCTCAG ACCTCGGGAG CCCCCAGCTG
19451 TCTTTCCCCA GACTCACTCC GAAGCCAGCG GCATGGTGAC CCAGCTCTGA
19501 CCGGTGGCTT CTCGCTGCGC AGCCTCCAGG GCCCGAGGTG ATCCCGGTGG
19551 TGGGATCCAC GCTGGGCCGA GGATGGGACG TTTTTCTTCT TGGGCCCGGT
19601 CCACAGGTCC AAGGACACCC TCCCTCCAGG GTCCTCTCTT CCACAGTGGC
19651 GGGCCCACTC AGCCCCGAGA CCACCCAACC TCACCCTCCT GACCCCCATG
19701 TAAATATTGT TCTGCTGTCT GGGACTCCTG TCTAGGTGCC CCTGATGATG
19751 GGATGCTCTT TAAATAATAA AGATGGTTTT GATTAATGTG GCCTCCGAGC
19801 TTACAAATGT ACACAGCAAT GAGGACATTT TGTCAGGAAG GAAGAGAAGA
19851 ATTAGGACCT GGCGCAAATC AGACAGAGAG TGTGGGTCCC TCAGTTCCCA
19901 CTGATTTGAG ATTTAAGATT TTAATTGGTT CACTTAACTG GAATTTTCCT
19951 GGAGCAAATT GGCTTCAGGT ACAGCTGGAT CCAGCTGCTC TCTCAAATCT
20001 GCCTTAGGCT GTGTTAGCTT CATTTCCAAG CAGCCTCTCC TACAACCAGA
20051 GAGAGAGATG TCCCCTTCCA CACAAACTCT TTCCCAATCA CTGCAGAAAA
20101 AGACCCAGGC AACAACAACA ACAAAACCCC AGGCCCAGCT CCCATTGTAC
20151 AGATTTGGGT CACGTGCTCA TCCCTTGGCA AATCACTGTG CACCGGATGT
20201 ACGCGGTAGG GGTGGAGCGG GGTGGAGTGG GAGGAGCTAG GCCTTCAAGA
20251 ATCGTGTGAC CTGAGTGTGG GAGTCCCAAA GGAAATAGGG TGCTATTTCC
20301 AGAAGTGGAA ATAGATGCTC AGTGAGCAAA AAAGACATCT ACCTTTGAACC
20351 AACACGGAAA ACGGGGCCCT GTAAGGTGGA GATAGGGAGA CGCTGGGAAC
```

FIGURE 3F

```
20401 ACAGCCTGAG ACCCTCCCCC AACCCCTTTC TCCATCTGGG CAGCTTCTGG
20451 GGAGGAACCC CCTTCTGTAG AGCCTCTGCA GAGCCTCATG CAGCCCCGAT
20501 GGCCACCAGG GGGCACTGCT GCCCCAACAT TGTGACACAT TAAGGGGTTT
20551 CCTGCCTGGA GTCAGCCGCA TGTTGCTGAA AACCTGCTGT TCTGCTGAAG
20601 AAAGGCTCAG CGGGGGAGCC TGTTCACCAT GACTTTAAAT AATAACAATT
20651 ATCATACATC ACCCATGGAC CACAGCTTCC AAGCAATTTC CTTTTTTTTT
20701 TTTTTTTTTT TTTTTTGAGA CAGAGTTTCA CTCTTGTCTC CCAGGTTGGA
20751 GTGCAGTGGC GTGATCTTAG CTCACTACAA CCTCCGCCTC CTGGGTTCAA
20801 GCGATTCTCC TGCCTCGGCC TCCCGAGTAG CTGGGATTAC AGGCGTGCCC
20851 CACCACGCCC AGCTGATTTT TGTATTTTTA GTAGAGACGG GCTGTCACCA
20901 TGTTGGCCAG GCTGCTCTCG AACTCCTGAC CTCAGGTGAT CCACCTGCCT
20951 CGGCCTCCCA AAGTGCTGGG TGTCACGCGC ATCCATGTGA AGAGACCACC
21001 AAACAGGCTT TGTGTGAGCA ATAAAGCTTT CTAATCACCT GGGTGCAGGC
21051 AGGCTGAGTC CGAAAAGAGA GTCAGTGAAG GGAGGTAGGG GTGGGGCCGT
21101 TTTATGGGAT TTGGATAGGT AGTGGAAAAT TACAGTCAAA GGGGGTTGTT
21151 CTCTGGCGGG CAGGGGTGGG GGTCACAAGG TGCTCAGTGG GGGAGCTTCT
21201 GAGCCAGGAG AAGGAATTTC ACAAGGTAAT GTCATCAGTT AAGGCAGGAA
21251 CCGGCCATTT TCACTTCTTT TGTGATTCTT CAGTTACTTC AGGCCATCTG
21301 GATGTATACA TGCAGGCTTG GGCTCAGAGG CCTGACACTG GGATTACAGA
21351 TGTCTGCTGC CACACCTGGC TAATTTTTGT ATTTTTAGTA GAGACGGGTT
21401 TCACCATGTT GGCAGGCTGG TCTCGAACTC CTGACCTCAG GTGATCCGCC
21451 CACCTTGGCC TCCCAAAGTG CTGGGATTAC AAGCCTAAGC CACTGCACCC
21501 AGCCCAGCTT CCTAAAATAT AGATGATCTA CAAGAGCTCC TTTGAGAAAC
21551 TGACAAACTG TGCATTTGGA AAACGATCCC AGCGTCACTC CCCGATCCCC
21601 ACACCCCTGG CGAGGTTGAG CCCCACCACT GCTTTGTTGG TCAGGAGCCC
21651 CCAGGCCCAC ATCGTGTTAG CAGAGCCTCA GTGCAGTTTC CCCAAACGTC
21701 TACCTCTGGC TGTGGTGTTC TACCCATGGC ATGTGGGATG TAATTTGAGA
21751 CCTGACCTAC GGCTTGCTTT GTTAGAAACG TATT
     (SEQ ID NO:3)
```

FEATURES:
Start:    2085
Exon:     2085-2202
Intron:   2203-2285
Exon:     2286-2327
Intron:   2328-12478
Exon:     12479-12608
Intron:   12609-12934
Exon:     12935-12975
Intron:   12976-13152
Exon:     13153-13318
Intron:   13319-13432
Exon:     13433-13623
Intron:   13624-18463
Exon:     18464-18559
Intron:   18560-18752
Exon:     18753-18895
Intron:   18896-19080
Exon:     19081-19245
Intron:   19246-19461
Exon:     19462-19497
Stop:     19498

FIGURE 3G

Allelic Variants (SNPs):

| DNA Position | Major | Minor | Domain | Protein Position | Major | Minor |
|---|---|---|---|---|---|---|
| 5658 | G | A | Intron | | | |
| 5715 | A | C | Intron | | | |
| 6865 | G | A | Intron | | | |
| 7180 | T | C | Intron | | | |
| 9022 | A | G | Intron | | | |
| 9713 | T | - | Intron | | | |
| 9716 | C | - | Intron | | | |
| 9887 | C | G | Intron | | | |
| 11462 | C | A | Intron | | | |
| 13132 | - | C | Intron | | | |
| 13526 | C | T | Exon | 197 | V | V |
| 13718 | G | T | Intron | | | |

Context:

DNA Position

5658
AAAAGGCTGTGCAGTACTTGCCTCTTAGCCAGCACAGTGGACATTGGCTTTTGTATCTCA
CTCCTGAAATTCTTTCTTGAAATTTCTTGAGCAAGATCTTCCTGGACTTCCAGACTCTAT
GGCCTCTCACCCTATGGTGTGTCCCTGCCACCCCGGTAAAACCCTCCTCACTCATTGTGA
ATTATTTACTCCTGGCGAACTCCAGGAAGGCAGGGACCTTTTGTGGTCAGACGGTGCCTG
GCACATAGTAGGTTCTCAGGAAATCCTTGAGTTATGAGTGCACCCAAAGCCAAAACACTG
[G,A]
GATGAACTAGAGAGTCATGGGCCTCCAGCTGGAAAGGAGCGAGGCCACCACTCACAACCG
GCTCTGGCCAGCACCACGCCGCCACCCTGCAGAGGTATTTGGGTTTTTCAACAACTCAGG
GAAATGATGAAACAAACAAACAAACAAAAACAACCCCAAGCTTGTATCCCCACCTCGCTT
TTTTTTTCCTGGGATTTTCACACTTCTAAATATATCCAACAACTTGGCAGGCACACCAGG
TGACCCAGAACATCCTTTTTGTGTTGCCTGAAATGATAGGAACAAGAATAAAGAATTTAA
(SEQ ID NO:5)

5715
TCACTCCTGAAATTCTTTCTTGAAATTTCTTGAGCAAGATCTTCCTGGACTTCCAGACTC
TATGGCCTCTCACCCTATGGTGTGTCCCTGCCACCCCGGTAAAACCCTCCTCACTCATTG
TGAATTATTTACTCCTGGCGAACTCCAGGAAGGCAGGGACCTTTTGTGGTCAGACGGTGC
CTGGCACATAGTAGGTTCTCAGGAAATCCTTGAGTTATGAGTGCACCCAAAGCCAAAACA
CTGGGATGAACTAGAGAGTCATGGGCCTCCAGCTGGAAAGGAGCGAGGCCACCACTCACA
[A,C]
CCGGCTCTGGCCAGCACCACGCCGCCACCCTGCAGAGGTATTTGGGTTTTTCAACAACTC
AGGGAAATGATGAAACAAACAAACAAACAAAAACAACCCCAAGCTTGTATCCCCACCTCG
CTTTTTTTTTCCTGGGATTTTCACACTTCTAAATATATCCAACAACTTGGCAGGCACACC
AGGTGACCCAGAACATCCTTTTTGTGTTGCCTGAAATGATAGGAACAAGAATAAAGAATT
TAAAAGTGAGAAACAGCAGCAGAGAGTGTGACTTTAAAAATAGCCAGAGGGGACATTTGA
(SEQ ID NO:6)

6865
ATAGAATAAAATAAAATAAGAATCCGCCCCCCTCCCCGCCCCAGTTGGTGTTTCAAACCC
TGAGACTTGGCCTTGGAATTCATGGGGTGATGAGGACCCCACAGCCAGAGGTGCCAGGCG
TTCCCTGCCCCAACCCCAGAGCAGGAGGCCATCATTAAGGCAGGCCAGCCAGGTGGCTTT
TCAGTGCCAGCCGTAGCTGAATATATTAGGCAGGGAGACAGGCAAGGGTTTGTATGAGAC
CCACAGAAGGAACAGGGAATATGCTGGTCTGGGTTCAAGTCCCGGTTTTGCTGGTTAGCC
[G,A]
TGTGCCTCTGGGCAAGTTTATTCCTCTGAGGCTTAGTTTTCCCATCTGTAAGATGGGCAT
AGAAGTGGTCACTACTGGCTGGGCACAGTGGCTCACGCCTGTAATCCCAGCACTTGGGGA
GGCCAAGGCAGGTGGATCACCTGAGGCCAGAAGTTCGAGACCAGCCTGGCCAACATGGTG
AAACGCTGTTTCTACTAAGAACACAAAAGTTAGCCAGGTGTAGTAGCATGTGCCTGTAAT
CCCAGCTACTCGGGAGGCTGAGGCAGGAGGATCGCTTGAACCTGGGAGGCAGAGGTTGCA
(SEQ ID NO:7)

7180
AGTTTATTCCTCTGAGGCTTAGTTTTCCCATCTGTAAGATGGGCATAGAAGTGGTCACTA
CTGGCTGGGCACAGTGGCTCACGCCTGTAATCCCAGCACTTGGGGAGGCCAAGGCAGGTG
GATCACCTGAGGCCAGAAGTTCGAGACCAGCCTGGCCAACATGGTGAAACGCTGTTTCTA
CTAAGAACACAAAAGTTAGCCAGGTGTAGTAGCATGTGCCTGTAATCCCAGCTACTCGGG
AGGCTGAGGCAGGAGGATCGCTTGAACCTGGGAGGCAGAGGTTGCAGTGAGCCGAGATCA
[T,C]

FIGURE 3H

```
      GCCACTGCACTCCAGCCTGAGCAACAGAGCAAGATTATGTCTCAAAAAAAAAAAAAAAAA
      CCGAAGTGGTCACTATCTCCGAGGATGGTTGTGGGATTCAGAGAGCCACTTGGATAGGAT
      GCATAGCATGGGGCCAGCCCACTGACACCCCCAGTAAACGTAGCCAGTGCTATTATTAC
      TGTGCTGTTGTTTAACCCTCCAGAGGGGAAGTCTCTTGAGAGGCTGTCCAGGGCAATGTT
      AAAAGCTTGGGGTTTGAAGTCACTCAGACCTGATTTCGAATCCTCTCTCCCTGCTTCTCG
      (SEQ ID NO:8)
```

9022
```
      CCTGGCTGCACCTCACACCAGGTGCCAGCAAAGCCCTGATGTTGCTCTATTTCTAGCTCC
      CACCTGATCTGCCCCTCCCTGGCTCACTCTGCTCTGGCCTCCCACTGTTCCTGGAGCACT
      CCCCCCAGTCCCCCACACCAGCCTTGGGATCTTTGCATCTGCAAGTCCCTCTGTCTCCGT
      GCTGATCTCACACACCTCCTGACACTTTCTCACCTCCTGCAGGTCTTTGTTCCTGCACCA
      CCTTCCCAGGGACGCTCTCCTTGCAGCGACTGAAAAGTGCAACCTCACCCCACCCTCCAC
      [A,G]
      CCGGCACTCCCCTCCCTCGGTGGCATTTTATTTTTCTCTGTGGCCCCTTCCTATCTTGTG
      ACACATAATATATCCTACTTATTTGTCCCTTTCTTGATTTGTCTCACCTACTGAGCTTTG
      AGTTCCACAGGGGTCGGGGTTTTTGTCTGATTTGTTCATTGCAGTGGTGATTTGTTCACT
      GCCTAAAATAGAGCCTGGCAGGTACAAAGTGTTTGGTAAATAGAAATCAATACCCCAGGG
      TCTGTGACCTGACTTAGGTGTTAACAGGTTCCTCTGAGGTGTGTGGGGAACAGACTGAGG
      (SEQ ID NO:9)
```

9713
```
      GTATATCCCAGCCCTGCCTCATGTCACAATTTGTAATGATGTGTTTGGCTGGGTGACATT
      TTATGGCCATCTGTCTCCCTATCCCCTATAATGTGGTTTGCCGAAAGCAAAGCCCAGGAC
      TGTCTCGGCCATCTGTGTCTCCAGGATCACCCCTCACTGGGCATGGAGTATGTGTCCAGT
      TAACGCTTGCTGAGTGAATGAATGAATACTCCATCCTCTGCCTGGAGAATTACGCACTTT
      AGCATATCCAAGGCTCTGACAAGTCCTGCATAAAAGAGCATTATTGTTTTCTTTCTTTCT
      [T,-]
      TCCTTCTTTCCCTCTTCTTTTCTTTCTGACTATAGGATATTGATTATCAATCTGGCAATA
      GTCAAGATTGGCAGTCTGGTGTATTAGTCAAAGGTTTTCAGCCTACAAAAGACAAAAAGA
      AAAAATAAACTGGCTAAAAACAAAAGGGGATATGATTTACTAACTCACTTAACCGACAGT
      CACAGAGGTTCTTCAAACCTGGCTGTATCAAGGGGCTTTAAAATGTTATCAGATGGGGGC
      CAGGTGCAGTAGCTCACGCCTGTCATCCAGCACTTTGGGAGGCCAAGACAGGCAGATCAC
      (SEQ ID NO:10)
```

9716
```
      TATCCCAGCCCTGCCTCATGTCACAATTTGTAATGATGTGTTTGGCTGGGTGACATTTTA
      TGGCCATCTGTCTCCCTATCCCCTATAATGTGGTTTGCCGAAAGCAAAGCCCAGGACTGT
      CTCGGCCATCTGTGTCTCCAGGATCACCCCTCACTGGGCATGGAGTATGTGTCCAGTTAA
      CGCTTGCTGAGTGAATGAATGAATACTCCATCCTCTGCCTGGAGAATTACGCACTTTAGC
      ATATCCAAGGCTCTGACAAGTCCTGCATAAAAGAGCATTATTGTTTTCTTTCTTTCTTTC
      [C,-]
      TTCTTTCCCTCTTCTTTTCTTTCTGACTATAGGATATTGATTATCAATCTGGCAATAGTC
      AAGATTGGCAGTCTGGTGTATTAGTCAAAGGTTTTCAGCCTACAAAAGACAAAAGAAAA
      AATAAACTGGCTAAAAACAAAAGGGGATATGATTTACTAACTCACTTAACCGACAGTCAC
      AGAGGTTCTTCAAACCTGGCTGTATCAAGGGGCTTTAAAATGTTATCAGATGGGGGCCAG
      GTGCAGTAGCTCACGCCTGTCATCCAGCACTTTGGGAGGCCAAGACAGGCAGATCACTTG
      (SEQ ID NO:11)
```

9887
```
      TCCAGTTAACGCTTGCTGAGTGAATGAATGAATACTCCATCCTCTGCCTGGAGAATTACG
      CACTTTAGCATATCCAAGGCTCTGACAAGTCCTGCATAAAAGAGCATTATTGTTTTCTTT
      CTTTCTTTCCTTCTTTCCCTCTTCTTTTCTTTCTGACTATAGGATATTGATTATCAATCT
      GGCAATAGTCAAGATTGGCAGTCTGGTGTATTAGTCAAAGGTTTTCAGCCTACAAAAGAC
      AAAAAGAAAAATAAACTGGCTAAAAACAAAAGGGGATATGATTTACTAACTCACTTAAC
      [C,G]
      GACAGTCACAGAGGTTCTTCAAACCTGGCTGTATCAAGGGGCTTTAAAATGTTATCAGAT
      GGGGGCCAGGTGCAGTAGCTCACGCCTGTCATCCAGCACTTTGGGAGGCCAAGACAGGCA
      GATCACTTGAGGTCAGGAGTTCGAGACCAGCCTGGCCAACATGGTGAAACCCCGTGTCTA
      CTAAAAATACAAAAAATTAGCCAAGTGTGGTGGCATGTGTCTGTAGCTCCAGCTACTCGG
      GAGGCTGAGGCAGGACAATGGCTTGAATCCGGGAGGCGGAGGTTACAGTGACCCAAGGTT
      (SEQ ID NO:12)
```

11462
```
      TAGTTTTCATAGAGACGAGGTTTCATCATCTTGGCCAGGCTGGTCTTGAACTCCTGACCT
      TGTGATCCACCCATCTCGGCCTCCCAAATAAATACATATTTTAAAAGATAGAAATCACTC
      TGGAAGGAGAGTTAATCTGTTTGATATAATAATAATATATTAATATTATATTATAACAAT
      ATATTAGTATTATATTCTAATAATATATTAATATTATATTATAATAATATATTATTATAT
      TATAACAATATATTAATATTATATTATAACAATATATTAATATTATATTATGTAATAATA
      [C,A]
      TACTACTCCATATAGCTATGGAAAAGTTCATATGAAGAAACCAGGCTATGATCTACAAAC
      TGGCAACAAATTTGTTCTTCTATTTTCCATATGCTGTCTGTGTACGTATAAAGTGAGAGG
      TCTTTTTATATGAGTTAAGGGTGTGACCAAAGACAAATGGAAAAAGACAAATGACAAACA
```

FIGURE 3I

TACTAATAAAGAGCTTCGGTTTCTCCACAAAAAATACAATAATAAAATAAAATGTTATCA
GAAATCTCTTGACTCTCCTCCACGTTAGCTCACTTTTTCCCTCAAGAGGGTGAACATGAC
(SEQ ID NO:13)

13132   CACCTCAGACCCCCAAGGCACTCCCTCTCCCCGTTTTCCTTCCACCTGTCTTAACTGGTC
TCTATTTCCTTTCTTTCTGTGTCTCCAATCCCATCTCTCCCAGTGATTGCCCCAGAGGCC
GTTTCTTGGCCGCCATCTGCCAAGGTGAGATCCTAAAACTCAGAACCCTCTCCTTTAGGC
CCTTGGGGAGGCCACGTCCCCTCAAGCTCCCCAGGATGGGGCCATGTACTTTCAGACCCC
CTAGGGCAGGGCCAAGCCTGGGCTCTGGGGACCTGGGCTCCAGTCCCCTGTCGCCGCCCC
[-,C]
TGCTGACCCTTGTCCCACAGACTGTGGCCGCAGGAAGCTGCCCGTGGACCGCATCGTGGG
AGGCCGGGACACCAGCTTGGGCCGGTGGCCGTGGCAAGTCAGCCTTCGCTATGATGGAGC
ACACCTCTGTGGGGGATCCCTGCTCTCCGGGGACTGGGTGCTGACAGCCGCCCACTGCTT
CCCGGAGTGAGTGCCCCCAATGGCGCTGATGATGGGGAGGCAGAGGAGCGGAGAGACAG
TGGGGAGGAGGGCGGATTGTGCCCAGGCAGGTGGCCACCCTCCACCCCTTTCCCTGGTAG
(SEQ ID NO:14)

13526   GCAAGTCAGCCTTCGCTATGATGGAGCACACCTCTGTGGGGGATCCCTGCTCTCCGGGGA
CTGGGTGCTGACAGCCGCCCACTGCTTCCCGGAGTGAGTGCCCCCAATGGCGCTGATGA
TGGGGAGGCAGAGGAGCGGAGAGACAGTGGGGAGGAGGGCGGATTGTGCCCAGGCAGGTG
GCCACCCTCCACCCCTTTCCCTGGTAGGCGGAACCGGGTCCTGTCCCGATGGCGAGTGTT
TGCCGGTGCCGTGGCCCAGGCCTCTCCCCACGGTCTGCAGCTGGGGGTGCAGGCTGTGGT
[C,T]
TACCACGGGGGCTATCTTCCCTTTCGGGACCCCAACAGCGAGGAGAACAGCAACGATATT
GCCCTGGTCCACCTCTCCAGTCCCCTGCCCCTCACAGGTAAGTCTAAGGGCTGAGCCATG
GGGCTTGAGGACCCGAGGCCAGGAGGACAGAGGAGGGGACCAGGGGCACAAGGCAATCAA
CTTATGGCTCAGGCATCCTTGGCAATAAGGGGAATGATCTCGAGGGAGCACAAAGTGGGC
CTTAACTATCAATGATCAGTGCAGCCAATTTGGAAAATTTGCCAGCATTTCCCCAAGAAG
(SEQ ID NO:15)

13718   CCCTTTCCCTGGTAGGCGGAACCGGGTCCTGTCCCGATGGCGAGTGTTTGCCGGTGCCGT
GGCCCAGGCCTCTCCCCACGGTCTGCAGCTGGGGGTGCAGGCTGTGGTCTACCACGGGGG
CTATCTTCCCTTTCGGGACCCCAACAGCGAGGAGAACAGCAACGATATTGCCCTGGTCCA
CCTCTCCAGTCCCCTGCCCCTCACAGGTAAGTCTAAGGGCTGAGCCATGGGGCTTGAGGA
CCCGAGGCCAGGAGGACAGAGGAGGGGACCAGGGGCACAAGGCAATCAACTTATGGCTCA
[G,T]
GCATCCTTGGCAATAAGGGGAATGATCTCGAGGGAGCACAAAGTGGGCCTTAACTATCAA
TGATCAGTGCAGCCAATTTGGAAAATTTGCCAGCATTTCCCCAAGAAGTATACATAAAGT
TACCATTGGACCCAACACTTCCACTCCCAGGACAGGAGGTATATACCTAAGACAAATGGA
AACTGTGTCTGCACCAAAACTCGTACATCAGTGTTCATAGCAGCATTATTCATAATAGCC
CAAAGATGGAAACAGCCCAAGAGTGTTTCATCGGACAAATGCATAAAGAAAATGTGGTAT
(SEQ ID NO:16)

Chromosome mapping:
Chromosome 19

FIGURE 3J

ISOLATED HUMAN PROTEASE PROTEINS, NUCLEIC ACID MOLECULES ENCODING HUMAN PROTEASE PROTEINS, AND USES THEREOF

This application is a divisional of 09/820,002 filed on Mar. 29, 2001 which is now U.S. Pat. No. 6,482,630, issued Nov. 19, 2002.

FIELD OF THE INVENTION

The present invention is in the field of protease proteins that are related to the hepsin protease subfamily, recombinant DNA molecules, and protein production. The present invention specifically provides novel peptides and proteins that effect protein cleavage/processing/turnover and nucleic acid molecules encoding such peptide and protein molecules, all of which are useful in the development of human therapeutics and diagnostic compositions and methods.

BACKGROUND OF THE INVENTION

The proteases may be categorized into families by the different amino acid sequences (generally between 2 and 10 residues) located on either side of the cleavage site of the protease.

The proper functioning of the cell requires careful control of the levels of important structural proteins, enzymes, and regulatory proteins. One of the ways that cells can reduce the steady state level of a particular protein is by proteolytic degradation. Further, one of the ways cells produce functioning proteins is to produce pre or pro-protein precursors that are processed by proteolytic degradation to produce an active moiety. Thus, complex and highly-regulated mechanisms have been evolved to accomplish this degradation.

Proteases regulate many different cell proliferation, differentiation, and signaling processes by regulating protein turnover and processing. Uncontrolled protease activity (either increased or decreased) has been implicated in a variety of disease conditions including inflammation, cancer, arteriosclerosis, and degenerative disorders.

An additional role of intracellular proteolysis is in the stress-response. Cells that are subject to stress such as starvation, heat-shock, chemical insult or mutation respond by increasing the rates of proteolysis. One function of this enhanced proteolysis is to salvage amino acids from non-essential proteins. These amino acids can then be re-utilized in the synthesis of essential proteins or metabolized directly to provide energy. Another function is in the repair of damage caused by the stress. For example, oxidative stress has been shown to damage a variety of proteins and cause them to be rapidly degraded.

The International Union of Biochemistry and Molecular Biology (IUBMB) has recommended to use the term peptidase for the subset of peptide bond hydrolases (Subclass E.C 3.4.). The widely used term protease is synonymous with peptidase. Peptidases comprise two groups of enzymes: the endopeptidases and the exopeptidases, which cleave peptide bonds at points within the protein and remove amino acids sequentially from either N or C-terminus respectively. The term proteinase is also used as a synonym word for endopeptidase and four mechanistic classes of proteinases are recognized by the IUBMB: two of these are described below (also see: *Handbook of Proteolytic Enzymes* by Barrett, Rawlings, and Woessner A P Press, NY 1998). Also, for a review of the various uses of proteases as drug targets, see: Weber M, Emerging treatments for hypertension: potential role for vasopeptidase inhibition; Am J Hypertens 1999 November;12(11 Pt 2):139S–147S; Kentsch M, Otter W, Novel neurohormonal modulators in cardiovascular disorders. The therapeutic potential of endopeptidase inhibitors, Drugs R D 1999 April;1(4):331–8; Scarborough R M, Coagulation factor Xa: the prothrombinase complex as an emerging therapeutic target for small molecule inhibitors, J Enzym Inhib 1998;14(1):15–25; Skotnicki J S, et al., Design and synthetic considerations of matrix metalloproteinase inhibitors, Ann N Y Acad Sci 1999 Jun. 30;878:61–72; McKerrow J H, Engel J C, Caffrey C R, Cysteine protease inhibitors as chemotherapy for parasitic infections, Bioorg Med Chem 1999 April;7(4):639–44; Rice K D, Tanaka R D, Katz B A, Numerof R P, Moore W R, Inhibitors of tryptase for the treatment of mast cell-mediated diseases, Curr Pharm Des 1998 October;4(5):381–96; Materson B J, Will angiotensin converting enzyme genotype, receptor mutation identification, and other miracles of molecular biology permit reduction of NNT Am J Hypertens 1998 August;11(8 Pt 2):138S–142S Serine Proteases The serine proteases (SP) are a large family of proteolytic enzymes that include the digestive enzymes, trypsin and chymotrypsin, components of the complement cascade and of the blood-clotting cascade, and enzymes that control the degradation and turnover of macromolecules of the extracellular matrix. SP are so named because of the presence of a serine residue in the active catalytic site for protein cleavage. SP have a wide range of substrate specificities and can be subdivided into subfamilies on the basis of these specificities. The main sub-families are trypases (cleavage after arginine or lysine), aspases (cleavage after aspartate), chymases (cleavage after phenylalanine or leucine), metases (cleavage after methionine), and serases (cleavage after serine).

A series of six SP have been identified in murine cytotoxic T-lymphocytes (CTL) and natural killer (NK) cells. These SP are involved with CTL and NK cells in the destruction of virally transformed cells and tumor cells and in organ and tissue transplant rejection (Zunino, S. J. et al. (1990) J. Immunol. 144:2001–9; Sayers, T. J. et al. (1994) J. Immunol. 152:2289–97). Human homologs of most of these enzymes have been identified (Trapani, J. A. et al. (1988) Proc. Natl. Acad. Sci. 85:6924–28; Caputo, A. et al. (1990) J. Immunol. 145:737–44). Like all SP, the CTL-SP share three distinguishing features:1) the presence of a catalytic triad of histidine, serine, and aspartate residues which comprise the active site; 2) the sequence GDSGGP which contains the active site serine; and 3) an N-terminal IIGG sequence which characterizes the mature SP.

The SP are secretory proteins which contain N-terminal signal peptides that serve to export the immature protein across the endoplasmic reticulum and are then cleaved (von Heijne (1986) Nuc. Acid. Res. 14:5683–90). Differences in these signal sequences provide one means of distinguishing individual SP. Some SP, particularly the digestive enzymes, exist as inactive precursors or preproenzymes, and contain a leader or activation peptide sequence 3' of the signal peptide. This activation peptide may be 2–12 amino acids in length, and it extends from the cleavage site of the signal peptide to the N-terminal IIGG sequence of the active, mature protein. Cleavage of this sequence activates the enzyme. This sequence varies in different SP according to the biochemical pathway and/or its substrate (Zunino et al, supra; Sayers et al, supra). Other features that distinguish various SP are the presence or absence of N-linked glycosylation sites that provide membrane anchors, the number and distribution of cysteine residues that determine the secondary structure of the SP, and the sequence of a substrate binding sites such as S'. The S' substrate binding region is defined by residues extending from approximately +17 to +29 relative to the N-terminal I (+1). Differences in this region of the molecule are believed to determine SP substrate specificities (Zunino et al, supra).

Trypsinogens

The trypsinogens are serine proteases secreted by exocrine cells of the pancreas (Travis J and Roberts R. Biochemistry 1969; 8: 2884–9; Mallory P and Travis J, Biochemistry 1973; 12: 2847–51). Two major types of trypsinogen isoenzymes have been characterized, trypsinogen-1, also called cationic trypsinogen, and trypsinogen-2 or anionic trypsinogen. The trypsinogen proenzymes are activated to trypsins in the intestine by enterokinase, which removes an activation peptide from the N-terminus of the trypsinogens. The trypsinogens show a high degree of sequence homology, but they can be separated on the basis of charge differences by using electrophoresis or ion exchange chromatography. The major form of trypsinogen in the pancreas and pancreatic juice is trypsinogen-1 (Guy C O et al., Biochem Biophys Res Commun 1984; 125: 516–23). In serum of healthy subjects, trypsinogen-1 is also the major form, whereas in patients with pancreatitis, trypsinogen-2 is more strongly elevated (Itkonen et al., J Lab Clin Med 1990; 115:712–8). Trypsinogens also occur in certain ovarian tumors, in which trypsinogen-2 is the major form (Koivunen et al., Cancer Res 1990; 50: 2375–8). Trypsin-1 in complex with alpha-1-antitrypsin, also called alpha-1-antiprotease, has been found to occur in serum of patients with pancreatitis (Borgstrom A and Ohlsson K, Scand J Clin Lab Invest 1984; 44: 381–6) but determination of this complex has not been found useful for differentiation between pancreatic and other gastrointestinal diseases (Borgstrom et al., Scand J Clin Lab Invest 1989; 49:757–62).

Trypsinogen-1 and -2 are closely related immunologically (Kimland et al., Clin Chim Acta 1989; 184: 31–46; Itkonen et al., 1990), but by using monoclonal antibodies (Itkonen et al., 1990) or by absorbing polyclonal antisera (Kimland et al., 1989) it is possible to obtain reagents enabling specific measurement of each form of trypsinogen.

When active trypsin reaches the blood stream, it is inactivated by the major trypsin inhibitors alpha-2-macroglobulin and alpha-1-antitrypsin (AAT). AAT is a 58 kilodalton serine protease inhibitor synthesized in the liver and is one of the main protease inhibitors in blood. Whereas complexes between trypsin-1 and AAT are detectable in serum (Borgstrom and Ohlsson, 1984) the complexes with alpha-2-macroglobulin are not measurable with antibody-based assays (Ohlsson K, Acta Gastroenterol Belg 1988; 51: 3–12).

Inflammation of the pancreas or pancreatitis may be classified as either acute or chronic by clinical criteria. With treatment, acute pancreatitis can often be cured and normal function restored. Chronic pancreatitis often results in permanent damage. The precise mechanisms which trigger acute inflammation are not understood. However, some causes in the order of their importance are alcohol ingestion, biliary tract disease, post-operative trauma, and hereditary pancreatitis. One theory provides that autodigestion, the premature activation of proteolytic enzymes in the pancreas rather than in the duodenum, causes acute pancreatitis. Any number of other factors including endotoxins, exotoxins, viral infections, ischemia, anoxia, and direct trauma may activate the proenzymes. In addition, any internal or external blockage of pancreatic ducts can also cause an accumulation of pancreatic juices in the pancreas resulting cellular damage.

Anatomy, physiology, and diseases of the pancreas are reviewed, inter alia, in Guyton A C (1991) Textbook of Medical Physiology, W B Saunders Co, Philadelphia Pa.; Isselbacher K J et al (1994) Harrison's Principles of Internal Medicine, McGraw-Hill, New York City; Johnson K E (1991) Histology and Cell Biology, Harwal Publishing, Media Pa.; and The Merck Manual of Diagnosis and Therapy (1992) Merck Research Laboratories, Rahway N.J.

Metalloprotease

The metalloproteases may be one of the older classes of proteinases and are found in bacteria, fungi as well as in higher organisms. They differ widely in their sequences and their structures but the great majority of enzymes contain a zinc atom which is catalytically active. In some cases, zinc may be replaced by another metal such as cobalt or nickel without loss of the activity. Bacterial thermolysin has been well characterized and its crystallographic structure indicates that zinc is bound by two histidines and one glutamic acid. Many enzymes contain the sequence HEXXH, which provides two histidine ligands for the zinc whereas the third ligand is either a glutamic acid (thermolysin, neprilysin, alanyl aminopeptidase) or a histidine (astacin). Other families exhibit a distinct mode of binding of the Zn atom. The catalytic mechanism leads to the formation of a non covalent tetrahedral intermediate after the attack of a zinc-bound water molecule on the carbonyl group of the scissile bond. This intermediate is further decomposed by transfer of the glutamic acid proton to the leaving group.

Metalloproteases contain a catalytic zinc metal center which participates in the hydrolysis of the peptide backbone (reviewed in Power and Harper, in Protease Inhibitors, A. J. Barrett and G. Salversen (eds.) Elsevier, Amsterdam, 1986, p. 219). The active zinc center differentiates some of these proteases from calpains and trypsins whose activities are dependent upon the presence of calcium. Examples of metalloproteases include carboxypeptidase A, carboxypeptidase B, and thermolysin.

Metalloproteases have been isolated from a number of procaryotic and eucaryotic sources, e.g. *Bacillus subtilis* (McConn et al., 1964, J. Biol. Chem. 239:3706); *Bacillus megaterium*; Serratia (Miyata et al., 1971, Agr. Biol. Chem. 35:460); *Clostridium bifermentans* (MacFarlane et al., 1992, App. Environ. Microbiol. 58:1195–1200), *Legionella pneumophila* (Moffat et al., 1994, Infection and Immunity 62:751–3). In particular, acidic metalloproteases have been isolated from broad-banded copperhead venoms (Johnson and Ownby, 1993, Int. J. Biochem. 25:267–278), rattlesnake venoms (Chlou et al., 1992, Biochem. Biophys. Res. Commun. 187:389–396) and articular cartilage (Treadwell et al., 1986, Arch. Biochem. Biophys. 251:715–723). Neutral metalloproteases, specifically those having optimal activity at neutral pH have, for example, been isolated from *Aspergillus sojae* (Sekine, 1973, Agric. Biol. Chem. 37:1945–1952). Neutral metalloproteases obtained from *Aspergillus* have been classified into two groups, npI and npII (Sekine, 1972, Agric. Biol. Chem. 36:207–216). So far, success in obtaining amino acid sequence information from these fungal neutral metalloproteases has been limited. An npII metalloprotease isolated from *Aspergillus oryzae* has been cloned based on amino acid sequence presented in the literature (Tatsumi et al., 1991, Mol. Gen. Genet. 228:97–103). However, to date, no npI fungal metalloprotease has been cloned or sequenced. Alkaline metalloproteases, for example, have been isolated from *Pseudomonas aeruginosa* (Baumann et al., 1993, EMBO J 12:3357–3364) and the insect pathogen *Xenorhabdus luminescens* (Schmidt et al., 1998, Appl. Environ. Microbiol. 54:2793–2797).

Metalloproteases have been devided into several distinct families based primarily on activity and sturcture:1) water nucleophile; water bound by single zinc ion ligated to two His (within the motif HEXXH) and Glu, His or Asp; 2) water nucleophile; water bound by single zinc ion ligated to His, Glu (within the motif HXXE) and His; 3) water nucleophile; water bound by single zinc ion ligated to His, Asp and His; 4) Water nucleophile; water bound by single zinc ion ligated to two His (within the motif HXXEH) and Glu and 5) water nucleophile; water bound by two zinc ions ligated by Lys, Asp, Asp, Asp, Glu.

Examples of members of the metalloproteinase family include, but are not limited to, membrane alanyl aminopeptidase (*Homo sapiens*), germinal peptidyl-dipeptidase A (*Homo sapiens*), thimet oligopeptidase (*Rattus norvegicus*), oligopeptidase F (*Lactococcus lactis*), mycolysin (*Streptomyces cacaoi*), immune inhibitor A (*Bacillus thuringiensis*), snapalysin (*Streptomyces lividans*), leishmanolysin (*Leishmania major*), microbial collagenase (*Vibrio alginolyticus*), microbial collagenase, class I (*Clostridium perfringens*), collagenase 1 (*Homo sapiens*), serralysin (*Serratia marcescens*), fragilysin (*Bacteroides fragilis*), gametolysin (*Chlamydomonas reinhardtii*), astacin (*Astacus fluviatilis*), adamalysin (*Crotalus adamanteus*), ADAM 10 (*Bos taurus*), neprilysin (*Homo sapiens*), carboxypeptidase A (*Homo sapiens*), carboxypeptidase E (*Bos taurus*), gamma-D-glutamyl-(L)-meso-diaminopimelate peptidase I (*Bacillus sphaericus*), vanY D-Ala-D-Ala carboxypeptidase (*Enterococcus faecium*), endolysin (bacteriophage A118), pitrilysin (*Escherichia coli*), mitochondrial processing peptidase (*Saccharomyces cerevisiae*), leucyl aminopeptidase (*Bos taurus*), aminopeptidase I (*Saccharomyces cerevisiae*), membrane dipeptidase (*Homo sapiens*), glutamate carboxypeptidase (Pseudomonas sp.), Gly-X carboxypeptidase (*Saccharomyces cerevisiae*), O-sialoglycoprotein endopeptidase (*Pasteurella haemolytica*), beta-lytic metalloendopeptidase (*Achromobacter lyticus*), methionyl aminopeptidase I (*Escherichia coli*), X-Pro aminopeptidase (*Escherichia coli*), X-His dipeptidase (*Escherichia coli*), IgA1-specific metalloendopeptidase (*Streptococcus sanguis*), tentoxilysin (*Clostridium tetani*), leucyl aminopeptidase (*Vibrio proteolyticus*), aminopeptidase (*Streptomyces griseus*), IAP aminopeptidase (*Escherichia coli*), aminopeptidase T (*Thermus aquaticus*), hyicolysin (*Staphylococcus hyicus*), carboxypeptidase Taq (*Thermus aquaticus*), anthrax lethal factor (*Bacillus anthracis*), penicillolysin (*Penicillium citrinum*), fungalysin (*Aspergillus fumigatus*), lysostaphin (*Staphylococcus simulans*), beta-aspartyl dipeptidase (*Escherichia coli*), carboxypeptidase Ss1 (*Sulfolobus solfataricus*), FtsH endopeptidase (*Escherichia coli*), glutamyl aminopeptidase (*Lactococcus lactis*), cytophagalysin (Cytophaga sp.), metalloendopeptidase (vaccinia virus), VanX D-Ala-D-Ala dipeptidase (*Enterococcus faecium*), Ste24p endopeptidase (*Saccharomyces cerevisiae*), dipeptidyl-peptidase III (*Rattus norvegicus*), S2P protease (*Homo sapiens*), sporulation factor SpoIVFB (*Bacillus subtilis*), and HYBD endopeptidase (*Escherichia coli*).

Metalloproteases have been found to have a number of uses. For example, there is strong evidence that a metalloprotease is involved in the in vivo proteolytic processing of the vasoconstrictor, endothelin-1. Rat metalloprotease has been found to be involved in peptide hormone processing. One important subfamily of the metalloproteases are the matrix metalloproteases.

A number of diseases are thought to be mediated by excess or undesired metalloprotease activity or by an imbalance in the ratio of the various members of the protease family of proteins. These include: a) osteoarthritis (Woessner, et al., J. Biol. Chem. 259(6), 3633, 1984; Phadke, et al., J. Rheumatol. 10, 852, 1983), b) rheumatoid arthritis (Mullins, et al., Biochim. Biophys. Acta 695, 117, 1983; Woolley, et al., Arthritis Rheum. 20, 1231, 1977; Gravallese, et al., Arthritis Rheum. 34, 1076, 1991), c) septic arthritis (Williams, et al., Arthritis Rheum. 33, 533, 1990), d) tumor metastasis (Reich, et al., Cancer Res. 48, 3307, 1988, and Matrisian, et al., Proc. Nat'l. Acad. Sci., USA 83, 9413, 1986), e) periodontal diseases (Overall, et al., J. Periodontal Res. 22, 81, 1987), f) corneal ulceration (Bums, et al., Invest. Opthalmol. Vis. Sci. 30, 1569, 1989), g) proteinuria (Baricos, et al., Biochem. J. 254, 609, 1988), h) coronary thrombosis from atherosclerotic plaque rupture (Henney, et al., Proc. Nat'l. Acad. Sci., USA 88, 8154–8158, 1991), i) aneurysmal aortic disease (Vine, et al., Clin. Sci. 81, 233, 1991), j) birth control (Woessner, et al., Steroids 54, 491, 1989), k) dystrophobic epidermolysis bullosa (Kronberger, et al., J. Invest. Dermatol. 79, 208, 1982), and l) degenerative cartilage loss following traumatic joint injury, m) conditions leading to inflammatory responses, osteopenias mediated by MMP activity, n) tempero mandibular joint disease, o) demyelating diseases of the nervous system (Chantry, et al., J. Neurochem. 50, 688, 1988).

Aspartic Protease

Aspartic proteases have been divided into several distinct families based primarily on activity and structure. These include 1) water nucleophile; water bound by two Asp from monomer or dimer; all endopeptidases, from eukaryote organisms, viruses or virus-like organisms and 2) endopeptidases that are water nucleophile and are water bound by Asp and Asn.

Most of aspartic proteases belong to the pepsin family. The pepsin family includes digestive enzymes such as pepsin and chymosin as well as lysosomal cathepsins D and processing enzymes such as renin, and certain fungal proteases (penicillopepsin, rhizopuspepsin, endothiapepsin). A second family comprises viral proteases such as the protease from the AIDS virus (HIV) also called retropepsin. Crystallographic studies have shown that these enzymes are bilobed molecules with the active site located between two homologous lobes. Each lobe contributes one aspartate residue of the catalytically active diad of aspartates. These two aspartyl residues are in close geometric proximity in the active molecule and one aspartate is ionized whereas the second one is unionized at the optimum pH range of 2–3. Retropepsins, are monomeric, i.e carry only one catalytic aspartate and then dimerization is required to form an active enzyme.

In contrast to serine and cysteine proteases, catalysis by aspartic protease do not involve a covalent intermediate though a tetrahedral intermediate exists. The nucleophilic attack is achieved by two simultaneous proton transfer: one from a water molecule to the diad of the two carboxyl groups and a second one from the diad to the carbonyl oxygen of the substrate with the concurrent CO—NH bond cleavage. This general acid-base catalysis, which may be called a "push-pull" mechanism leads to the formation of a non covalent neutral tetrahedral intermediate.

Examples of the aspartic protease family of proteins include, but are not limited to, pepsin A (Homo sapiens), HIV1 retropepsin (human immunodeficiency virus type 1), endopeptidase (cauliflower mosaic virus), bacilliform virus putative protease (rice tungro bacilliform virus), aspergillopepsin II (*Aspergillus niger*), thermopsin (*Sulfolobus acidocaldarius*), nodavirus endopeptidase (flock house virus), pseudomonapepsin (*Pseudomonas* sp. 101), signal peptidase II (*Escherichia coli*), polyprotein peptidase (human spumaretrovirus), copia transposon (*Drosophila melanogaster*), SIRE-1 peptidase (*Glycine max*), retrotransposon bs1 endopeptidase (*Zea mays*), retrotransposon peptidase (*Drosophila buzzatii*), Tas retrotransposon peptidase (*Ascaris lumbricoides*), Pao retrotransposon peptidase (*Bombyx mori*), putative proteinase of Skippy retrotransposon (*Fusarium oxysporum*), tetravirus endopeptidase (*Nudaurelia capensis* omega virus), presenilin 1 (*Homo sapiens*).

Proteases and Cancer

Proteases are critical elements at several stages in the progression of metastatic cancer. In this process, the proteolytic degradation of structural protein in the basal membrane allows for expansion of a tumor in the primary site, evasion from this site as well as homing and invasion in distant, secondary sites. Also, tumor induced angiogenesis is required for tumor growth and is dependent on proteolytic tissue remodeling. Transfection experiments with various types of proteases have shown that the matrix metalloproteases play a dominant role in these processes in particular gelatinases A and B (MMP-2 and MMP-9, respectively). For an overview of this field see Mullins, et al., Biochim. Biophys. Acta 695, 177, 1983; Ray, et al., Eur. Respir. J. 7, 2062, 1994; Birkedal-Hansen, et al., Crit. Rev. Oral Biol. Med. 4, 197, 1993.

Furthermore, it was demonstrated that inhibition of degradation of extracellular matrix by the native matrix metalloprotease inhibitor TIMP-2 (a protein) arrests cancer growth (DeClerck, et al., Cancer Res. 52, 701, 1992) and that TIMP-2 inhibits tumor-induced angiogenesis in experimental systems (Moses, et al. Science 248, 1408, 1990). For a review, see DeClerck, et al., Ann. N.Y. Acad. Sci. 732, 222, 1994. It was further demonstrated that the synthetic matrix metalloprotease inhibitor batimastat when given intraperitoneally inhibits human colon tumor growth and spread in an orthotopic model in nude mice (Wang, et al. Cancer Res. 54, 4726, 1994) and prolongs the survival of mice bearing human ovarian carcinoma xenografts (Davies, et. al., Cancer Res. 53, 2087, 1993). The use of this and related compounds has been described in Brown, et al., WO-9321942 A2.

There are several patents and patent applications claiming the use of metalloproteinase inhibitors for the retardation of metastatic cancer, promoting tumor regression, inhibiting cancer cell proliferation, slowing or preventing cartilage loss associated with osteoarthritis or for treatment of other diseases as noted above (e.g. Levy, et al., WO-9519965 A1; Beckett, et al., WO-9519956 A1; Beckett, et al., WO-9519957 A1; Beckett, et al., WO-9519961 A1; Brown, et al., WO-9321942 A2; Crimmin, et al., WO-9421625 A1; Dickens, et al., U.S. Pat. No. 4,599,361; Hughes, et al., U.S. Pat. No. 5,190,937; Broadhurst, et al., EP 574758 A1; Broadhurst, et al., EP 276436; and Myers, et al., EP 520573 A1.

Hepsin

Extracellular proteases mediate the digestion of neighboring extracellular matrix components in initial tumor growth, allow shedding or desquamation of tumor cells into the surrounding environment, provide the basis for invasion of basement membranes in target metastatic organs, and are required for release and activation of many growth and angiogenic factors. Experimental evidence indicates that hepsin, a cell surface serine protease identified in hepatoma cells, is overexpressed in ovarian cancer. Hepsin is a serine protease found in most tissues, abundant in the liver. It is a membrane associated protein and is not found in the cytosol. Hepsin does not appear to be essential for development or homeostasis. On Northern blot analysis, the hepsin transcript was abundant in carcinoma but was almost never expressed in normal adult tissue, including normal ovary, suggesting that hepsin is frequently overexpressed in ovarian tumors and therefore may be a candidate protease in the invasive process and growth capacity of ovarian tumor cells.

For more information, see: Tanimoto, et al., Cancer Res. 1997 July 15;57(14):2884–7; Leytus, et al., Biochemistry 27: 1067–1074, 1988, PubMed ID : 2835076; Tsuji, et al., J. Biol. Chem. 266: 16948–16953, 1991, PubMed ID :1885621; and Wu, Q., et al., J. Clin. Invest. 101: 321–326, 1998, PubMed ID :9435303.

Protease proteins, particularly members of the hepsin subfamily, are a major target for drug action and development. Accordingly, it is valuable to the field of pharmaceutical development to identify and characterize previously unknown members of this subfamily of protease proteins. The present invention advances the state of the art by providing a previously unidentified human protease proteins that have homology to members of the hepsin subfamily.

SUMMARY OF THE INVENTION

The present invention is based in part on the identification of amino acid sequences of human protease peptides and proteins that are related to the hepsin protease subfamily, as well as allelic variants and other mammalian orthologs thereof. These unique peptide sequences, and nucleic acid sequences that encode these peptides, can be used as models for the development of human therapeutic targets, aid in the identification of therapeutic proteins, and serve as targets for the development of human therapeutic agents that modulate protease activity in cells and tissues that express the protease. Experimental data as provided in FIG. 1 indicates that protease proteins of the present invention are expressed in the liver, prostate, T cells from T cell leukemia, hepatocellular carcinoma, and lung tumor. Specifically, a virtual northern blot shows expression in the liver, prostate, T cells from T cell leukemia, hepatocellular carcinoma, and lung tumor.

DESCRIPTION OF THE FIGURE SHEETS

FIG. 1 provides the nucleotide sequence of a cDNA molecule or transcript sequence that encodes the protease protein of the present invention. (SEQ ID NO:1) In addition, structure and functional information is provided, such as ATG start, stop and tissue distribution, where available, that allows one to readily determine specific uses of inventions based on this molecular sequence. Experimental data as provided in FIG. 1 indicates that protease proteins of the present invention are expressed in the liver, prostate, T cells from T cell leukemia, hepatocellular carcinoma, and lung tumor. Specifically, a virtual northern blot shows expression in the liver, prostate, T cells from T cell leukemia, hepatocellular carcinoma, and lung tumor.

FIG. 2 provides the predicted amino acid sequence of the protease of the present invention. (SEQ ID NO:2) In addition structure and functional information such as protein family, function, and modification sites is provided where available, allowing one to readily determine specific uses of inventions based on this molecular sequence.

FIG. 3 provides genomic sequences that span the gene encoding the protease protein of the present invention. (SEQ ID NO:3) In addition structure and functional information, such as intron/exon structure, promoter location, etc., is provided where available, allowing one to readily determine specific uses of inventions based on this molecular sequence. Twelve (12) SNPs, including 3 indels, have been identified in the gene encoding the protease protein provided by the present invention and are given in FIG. 3.

DETAILED DESCRIPTION OF THE INVENTION

General Description

The present invention is based on the sequencing of the human genome. During the sequencing and assembly of the human genome, analysis of the sequence information revealed previously unidentified fragments of the human genome that encode peptides that share structural and/or sequence homology to protein/peptide/domains identified and characterized within the art as being a protease protein or part of a protease protein and are related to the hepsin protease subfamily. Utilizing these sequences, additional genomic sequences were assembled and transcript and/or cDNA sequences were isolated and characterized. Based on this analysis, the present invention provides amino acid sequences of human protease peptides and proteins that are related to the hepsin protease subfamily, nucleic acid sequences in the form of transcript sequences, cDNA sequences and/or genomic sequences that encode these protease peptides and proteins, nucleic acid variation (allelic information), tissue distribution of expression, and information about the closest art known protein/peptide/domain that has structural or sequence homology to the protease of the present invention.

In addition to being previously unknown, the peptides that are provided in the present invention are selected based on their ability to be used for the development of commercially important products and services. Specifically, the present peptides are selected based on homology and/or structural relatedness to known protease proteins of the hepsin protease subfamily and the expression pattern observed. Experimental data as provided in FIG. 1 indicates that protease proteins of the present invention are expressed in the liver, prostate, T cells from T cell leukemia, hepatocellular carcinoma, and lung tumor. Specifically, a virtual northern blot shows expression in the liver, prostate, T cells from T cell leukemia, hepatocellular carcinoma, and lung tumor. The art has clearly established the commercial importance of members of this family of proteins and proteins that have expression patterns similar to that of the present gene. Some of the more specific features of the peptides of the present invention, and the uses thereof, are described herein, particularly in the Background of the Invention and in the annotation provided in the Figures, and/or are known within the art for each of the known hepsin family or subfamily of protease proteins.

SPECIFIC EMBODIMENTS

Peptide Molecules

The present invention provides nucleic acid sequences that encode protein molecules that have been identified as being members of the protease family of proteins and are related to the hepsin protease subfamily (protein sequences are provided in FIG. 2, transcript/cDNA sequences are provided in FIG. 1 and genomic sequences are provided in FIG. 3). The peptide sequences provided in FIG. 2, as well as the obvious variants described herein, particularly allelic variants as identified herein and using the information in FIG. 3, will be referred herein as the protease peptides of the present invention, protease peptides, or peptides/proteins of the present invention.

The present invention provides isolated peptide and protein molecules that consist of, consist essentially of, or comprise the amino acid sequences of the protease peptides disclosed in the FIG. 2, (encoded by the nucleic acid molecule shown in FIG. 1, transcript/cDNA or FIG. 3, genomic sequence), as well as all obvious variants of these peptides that are within the art to make and use. Some of these variants are described in detail below.

As used herein, a peptide is said to be "isolated" or "purified" when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components (the features of an isolated nucleic acid molecule is discussed below).

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the protease peptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated protease peptide can be purified from cells that naturally express it, purified from cells that have been altered to express it (recombinant), or synthesized using known protein synthesis methods. Experimental data as provided in FIG. 1 indicates that protease proteins of the present invention are expressed in the liver, prostate, T cells from T cell leukemia, hepatocellular carcinoma, and lung tumor. Specifically, a virtual northern blot shows expression in the liver, prostate, T cells from T cell leukemia, hepatocellular carcinoma, and lung tumor. For example, a nucleic acid molecule encoding the protease peptide is cloned into an expression vector, the expression vector introduced into a host cell and the protein expressed in the host cell. The protein can then be isolated from the cells by an appropriate purification scheme using standard protein purification techniques. Many of these techniques are described in detail below.

Accordingly, the present invention provides proteins that consist of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). The amino acid sequence of such a protein is provided in FIG. 2. A protein consists of an amino acid sequence when the amino acid sequence is the final amino acid sequence of the protein.

The present invention further provides proteins that consist essentially of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein consists essentially of an amino acid sequence when such an amino acid sequence is present with only a few additional amino acid residues, for example from about 1 to about 100 or so additional residues, typically from 1 to about 20 additional residues in the final protein.

The present invention further provides proteins that comprise the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein comprises an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids. The preferred classes of proteins that are comprised of the protease peptides of the present invention are the naturally occurring mature proteins. A brief description of how various types of these proteins can be made/isolated is provided below.

The protease peptides of the present invention can be attached to heterologous sequences to form chimeric or fusion proteins. Such chimeric and fusion proteins comprise a protease peptide operatively linked to a heterologous protein having an amino acid sequence not substantially homologous to the protease peptide. "Operatively linked" indicates that the protease peptide and the heterologous protein are fused in-frame. The heterologous protein can be fused to the N-terminus or C-terminus of the protease peptide.

In some uses, the fusion protein does not affect the activity of the protease peptide per se. For example, the fusion protein can include, but is not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant protease peptide. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., *Current Protocols in Molecular Biology*, 1992). Moreover, many expression vectors are commercially available that already encode a fusion moiety (e.g., a GST protein). A protease peptide-encoding nucleic acid can be cloned into such an expression vector such that the fusion moiety is linked in-frame to the protease peptide.

As mentioned above, the present invention also provides and enables obvious variants of the amino acid sequence of the proteins of the present invention, such as naturally occurring mature forms of the peptide, allelic/sequence variants of the peptides, non-naturally occurring recombinantly derived variants of the peptides, and orthologs and paralogs of the peptides. Such variants can readily be generated using art-known techniques in the fields of recombinant nucleic acid technology and protein biochemistry. It is understood, however, that variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the protease peptides of the present invention. The degree of homology/identity present will be based primarily on whether the peptide is a functional variant or non-functional variant, the amount of divergence present in the paralog family and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, or 90% or more of the length of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of sequence Data, Part 1*, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). In a preferred embodiment, the percent identity between two amino acid sequences is determined using the Needleman and Wunsch (J. Mol. Biol. (48):444–453 (1970)) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al., *Nucleic Acids Res.* 12(1):387 (1984)) (available at http://www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Myers and W. Miller (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (*J. Mol. Biol.* 215:403–10 (1990)). BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (*Nucleic Acids Res.* 25(17):3389–3402 (1997)). When utilizing BLAST and gapped BLAST programs, the default parameters of the respective programs (e.g., XBLAST and NBLAST) can be used.

Full-length pre-processed forms, as well as mature processed forms, of proteins that comprise one of the peptides of the present invention can readily be identified as having complete sequence identity to one of the protease peptides of the present invention as well as being encoded by the same genetic locus as the protease peptide provided herein. As indicated by the data presented in FIG. 3, the map position was determined to be on chromosome 19 by ePCR, and confirmed with radiation hybrid mapping.

Allelic variants of a protease peptide can readily be identified as being a human protein having a high degree (significant) of sequence homology/identity to at least a portion of the protease peptide as well as being encoded by the same genetic locus as the protease peptide provided herein. Genetic locus can readily be determined based on the genomic information provided in FIG. 3, such as the genomic sequence mapped to the reference human. As indicated by the data presented in FIG. 3, the map position was determined to be on chromosome 19 by ePCR, and confirmed with radiation hybrid mapping. As used herein, two proteins (or a region of the proteins) have significant homology when the amino acid sequences are typically at least about 70–80%, 80–90%, and more typically at least about 90–95% or more homologous. A significantly homologous amino acid sequence, according to the present invention, will be encoded by a nucleic acid sequence that will hybridize to a protease peptide encoding nucleic acid molecule under stringent conditions as more fully described below.

FIG. 3 provides information on SNPs that have been identified in a gene encoding the protease protein of the present invention. Twelve (12) SNP variants were found, including 3 indels (indicated by a "-") and 1 SNP in exons, none of which cause changes in the amino acid sequence.

Paralogs of a protease peptide can readily be identified as having some degree of significant sequence homology/identity to at least a portion of the protease peptide, as being encoded by a gene from humans, and as having similar activity or function. Two proteins will typically be considered paralogs when the amino acid sequences are typically at least about 60% or greater, and more typically at least about 70% or greater homology through a given region or domain. Such paralogs will be encoded by a nucleic acid sequence that will hybridize to a protease peptide encoding nucleic acid molecule under moderate to stringent conditions as more fully described below.

Orthologs of a protease peptide can readily be identified as having some degree of significant sequence homology/identity to at least a portion of the protease peptide as well as being encoded by a gene from another organism. Preferred orthologs will be isolated from mammals, preferably primates, for the development of human therapeutic targets and agents. Such orthologs will be encoded by a nucleic acid sequence that will hybridize to a protease peptide encoding nucleic acid molecule under moderate to stringent conditions, as more fully described below, depending on the degree of relatedness of the two organisms yielding the proteins. As indicated by the data presented in FIG. 3, the map position was determined to be on chromosome 19 by ePCR, and confirmed with radiation hybrid mapping.

FIG. 3 provides information on SNPs that have been identified in a gene encoding the protease protein of the present invention. Twelve (12) SNP variants were found, including 3 indels (indicated by a "-") and 1 SNP in exons, none of which cause changes in the amino acid sequence.

Non-naturally occurring variants of the protease peptides of the present invention can readily be generated using recombinant techniques. Such variants include, but are not limited to deletions, additions and substitutions in the amino acid sequence of the protease peptide. For example, one class of substitutions are conserved amino acid substitution. Such substitutions are those that substitute a given amino acid in a protease peptide by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., *Science* 247:1306–1310 (1990).

Variant protease peptides can be fully functional or can lack function in one or more activities, e.g. ability to bind substrate, ability to cleave substrate, ability to participate in a signaling pathway, etc. Fully functional variants typically contain only conservative variation or variation in non-critical residues or in non-critical regions. FIG. 2 provides the result of protein analysis and can be used to identify critical domains/regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., *Science* 244:1081–1085 (1989)), particularly using the results provided in FIG. 2. The latter procedure introduces single alanine mutations at every residue in the molecule.

The resulting mutant molecules are then tested for biological activity such as protease activity or in assays such as an in vitro proliferative activity. Sites that are critical for binding partner/substrate binding can also be determined by structural analysis such as crystallization, nuclear magnetic resonance or photoaffinity labeling (Smith et al., *J. Mol. Biol.* 224:899–904 (1992); de Vos et al. *Science* 255:306–312 (1992)).

The present invention further provides fragments of the protease peptides, in addition to proteins and peptides that comprise and consist of such fragments, particularly those comprising the residues identified in FIG. 2. The fragments to which the invention pertains, however, are not to be construed as encompassing fragments that may be disclosed publicly prior to the present invention.

As used herein, a fragment comprises at least 8, 10, 12, 14, 16, or more contiguous amino acid residues from a protease peptide. Such fragments can be chosen based on the ability to retain one or more of the biological activities of the protease peptide or could be chosen for the ability to perform a function, e.g. bind a substrate or act as an immunogen. Particularly important fragments are biologically active fragments, peptides that are, for example, about 8 or more amino acids in length. Such fragments will typically comprise a domain or motif of the protease peptide, e.g., active site, a transmembrane domain or a substrate-binding domain. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE analysis). The results of one such analysis are provided in FIG. 2.

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in protease peptides are described in basic texts, detailed monographs, and the research literature, and they are well known to those of skill in the art (some of these features are identified in FIG. 2).

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties*, 2nd Ed., T. E. Creighton, W. H. Freeman and Company, New York (1993). Many detailed reviews are available on this subject, such as by Wold, F., *Posttranslational Covalent Modification of Proteins*, B. C. Johnson, Ed., Academic Press, New York 1–12 (1983); Seifter et al. (*Meth. Enzymol.* 182: 626–646 (1990)) and Rattan et al. (*Ann. N.Y. Acad. Sci.* 663:48–62 (1992)).

Accordingly, the protease peptides of the present invention also encompass derivatives or analogs in which a substituted amino acid residue is not one encoded by the genetic code, in which a substituent group is included, in which the mature protease peptide is fused with another compound, such as a compound to increase the half-life of the protease peptide (for example, polyethylene glycol), or in which the additional amino acids are fused to the mature protease peptide, such as a leader or secretory sequence or a sequence for purification of the mature protease peptide or a pro-protein sequence.

Protein/Peptide Uses

The proteins of the present invention can be used in substantial and specific assays related to the functional information provided in the Figures; to raise antibodies or to elicit another immune response; as a reagent (including the labeled reagent) in assays designed to quantitatively determine levels of the protein (or its binding partner or ligand) in biological fluids; and as markers for tissues in which the corresponding protein is preferentially expressed (either constitutively or at a particular stage of tissue differentiation or development or in a disease state). Where the protein binds or potentially binds to another protein or ligand (such as, for example, in a protease-effector protein interaction or protease-ligand interaction), the protein can be used to identify the binding partner/ligand so as to develop a system to identify inhibitors of the binding interaction. Any or all of these uses are capable of being developed into reagent grade or kit format for commercialization as commercial products.

Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

Substantial chemical and structural homology exists between the hepsin protein described herein and cell surface serine proteases (see FIG. 1). As discussed in the background, cell surface serine proteases are known in the art to be involved in tumor growth and consequently may play a role in cancers such as ovarian cancer. For more information, see Tanimoto, et al., Cancer Res. 1997 July 15;57(14): 2884–7. Accordingly, the hepsin protein, and the encoding gene, provided by the present invention is useful for treating, preventing, and/or diagnosing cancers such as ovarian cancer.

The potential uses of the peptides of the present invention are based primarily on the source of the protein as well as the class/action of the protein. For example, proteases isolated from humans and their human/mammalian orthologs serve as targets for identifying agents for use in mammalian therapeutic applications, e.g. a human drug, particularly in modulating a biological or pathological response in a cell or tissue that expresses the protease. Experimental data as provided in FIG. 1 indicates that protease proteins of the present invention are expressed in the liver, prostate, T cells from T cell leukemia, hepatocellular carcinoma, and lung tumor. Specifically, a virtual northern blot shows expression in the liver, prostate, T cells from T cell leukemia, hepatocellular carcinoma, and lung tumor. A large percentage of pharmaceutical agents are being developed that modulate the activity of protease proteins, particularly members of the hepsin subfamily (see Background of the Invention). The structural and functional information provided in the Background and Figures provide specific and substantial uses for the molecules of the present invention, particularly in combination with the expression information provided in FIG. 1. Experimental data as provided in FIG. 1 indicates that protease proteins of the present invention are expressed in the liver, prostate, T cells from T cell leukemia, hepatocellular carcinoma, and lung tumor. Specifically, a virtual northern blot shows expression in the liver, prostate, T cells from T cell leukemia, hepatocellular carcinoma, and lung tumor. Such uses can readily be determined using the information provided herein, that which is known in the art, and routine experimentation.

The proteins of the present invention (including variants and fragments that may have been disclosed prior to the present invention) are useful for biological assays related to proteases that are related to members of the hepsin subfamily. Such assays involve any of the known protease functions or activities or properties useful for diagnosis and treatment of protease-related conditions that are specific for the subfamily of proteases that the one of the present invention belongs to, particularly in cells and tissues that express the protease. Experimental data as provided in FIG. 1 indicates that protease proteins of the present invention are expressed in the liver, prostate, T cells from T cell leukemia, hepatocellular carcinoma, and lung tumor. Specifically, a virtual northern blot shows expression in the liver, prostate, T cells from T cell leukemia, hepatocellular carcinoma, and lung tumor.

The proteins of the present invention are also useful in drug screening assays, in cell-based or cell-free systems. Cell-based systems can be native, i.e., cells that normally express the protease, as a biopsy or expanded in cell culture. Experimental data as provided in FIG. 1 indicates that protease proteins of the present invention are expressed in the liver, prostate, T cells from T cell leukemia, hepatocellular carcinoma, and lung tumor. Specifically, a virtual northern blot shows expression in the liver, prostate, T cells from T cell leukemia, hepatocellular carcinoma, and lung tumor. In an alternate embodiment, cell-based assays involve recombinant host cells expressing the protease protein.

The polypeptides can be used to identify compounds that modulate protease activity of the protein in its natural state or an altered form that causes a specific disease or pathology associated with the protease. Both the proteases of the present invention and appropriate variants and fragments can be used in high-throughput screens to assay candidate compounds for the ability to bind to the protease. These compounds can be further screened against a functional protease to determine the effect of the compound on the protease activity. Further, these compounds can be tested in animal or invertebrate systems to determine activity/effectiveness. Compounds can be identified that activate (agonist) or inactivate (antagonist) the protease to a desired degree.

Further, the proteins of the present invention can be used to screen a compound for the ability to stimulate or inhibit interaction between the protease protein and a molecule that normally interacts with the protease protein, e.g. a substrate or a component of the signal pathway that the protease protein normally interacts (for example, a protease). Such assays typically include the steps of combining the protease protein with a candidate compound under conditions that allow the protease protein, or fragment, to interact with the target molecule, and to detect the formation of a complex between the protein and the target or to detect the biochemical consequence of the interaction with the protease protein and the target, such as any of the associated effects of signal transduction such as protein cleavage, cAMP turnover, and adenylate cyclase activation, etc.

Candidate compounds include, for example, 1) peptides such as soluble peptides, including Ig-tailed fusion peptides and members of random peptide libraries (see, e.g., Lam et al., Nature 354:82–84 (1991); Houghten et al., Nature 354:84–86 (1991)) and combinatorial chemistry-derived molecular libraries made of D- and/or L- configuration amino acids; 2) phosphopeptides (e.g., members of random and partially degenerate, directed phosphopeptide libraries, see, e.g., Songyang et al., Cell 72:767–778 (1993)); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and 4) small organic and inorganic molecules (e.g., molecules obtained from combinatorial and natural product libraries).

One candidate compound is a soluble fragment of the receptor that competes for substrate binding. Other candidate compounds include mutant proteases or appropriate fragments containing mutations that affect protease function and thus compete for substrate. Accordingly, a fragment that competes for substrate, for example with a higher affinity, or a fragment that binds substrate but does not allow release, is encompassed by the invention.

The invention further includes other end point assays to identify compounds that modulate (stimulate or inhibit) protease activity. The assays typically involve an assay of events in the signal transduction pathway that indicate protease activity. Thus, the cleavage of a substrate, inactivation/activation of a protein, a change in the expression of genes that are up- or down-regulated in response to the protease protein dependent signal cascade can be assayed.

Any of the biological or biochemical functions mediated by the protease can be used as an endpoint assay. These include all of the biochemical or biochemical/biological events described herein, in the references cited herein, incorporated by reference for these endpoint assay targets, and other functions known to those of ordinary skill in the art or that can be readily identified using the information provided in the Figures, particularly FIG. 2. Specifically, a biological function of a cell or tissues that expresses the protease can be assayed. Experimental data as provided in FIG. 1 indicates that protease proteins of the present invention are expressed in the liver, prostate, T cells from T cell leukemia, hepatocellular carcinoma, and lung tumor. Specifically, a virtual northern blot shows expression in the liver, prostate, T cells from T cell leukemia, hepatocellular carcinoma, and lung tumor.

Binding and/or activating compounds can also be screened by using chimeric protease proteins in which the amino terminal extracellular domain, or parts thereof, the entire transmembrane domain or subregions, such as any of the seven transmembrane segments or any of the intracellular or extracellular loops and the carboxy terminal intracellular domain, or parts thereof, can be replaced by heterologous domains or subregions. For example, a substrate-binding region can be used that interacts with a different substrate then that which is recognized by the native protease. Accordingly, a different set of signal transduction components is available as an end-point assay for activation.

This allows for assays to be performed in other than the specific host cell from which the protease is derived.

The proteins of the present invention are also useful in competition binding assays in methods designed to discover compounds that interact with the protease (e.g. binding partners and/or ligands). Thus, a compound is exposed to a protease polypeptide under conditions that allow the compound to bind or to otherwise interact with the polypeptide. Soluble protease polypeptide is also added to the mixture. If the test compound interacts with the soluble protease polypeptide, it decreases the amount of complex formed or activity from the protease target. This type of assay is particularly useful in cases in which compounds are sought that interact with specific regions of the protease. Thus, the soluble polypeptide that competes with the target protease region is designed to contain peptide sequences corresponding to the region of interest.

To perform cell free drug screening assays, it is sometimes desirable to immobilize either the protease protein, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of protease-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a protease-binding protein and a candidate compound are incubated in the protease protein-presenting wells and the amount of complex trapped in the well can be quantitated. Methods for detecting such complexes, in addition to those described above for the GST-immobilized complexes, include immunodetection of complexes using antibodies reactive with the protease protein target molecule, or which are reactive with protease protein and compete with the target molecule, as well as enzyme-linked assays which rely on detecting an enzymatic activity associated with the target molecule.

Agents that modulate one of the proteases of the present invention can be identified using one or more of the above assays, alone or in combination. It is generally preferable to use a cell-based or cell free system first and then confirm activity in an animal or other model system. Such model systems are well known in the art and can readily be employed in this context.

Modulators of protease protein activity identified according to these drug screening assays can be used to treat a subject with a disorder mediated by the protease pathway, by treating cells or tissues that express the protease. Experimental data as provided in FIG. 1 indicates that protease proteins of the present invention are expressed in the liver, prostate, T cells from T cell leukemia, hepatocellular carcinoma, and lung tumor. Specifically, a virtual northern blot shows expression in the liver, prostate, T cells from T cell leukemia, hepatocellular carcinoma, and lung tumor. These methods of treatment include the steps of administering a modulator of protease activity in a pharmaceutical composition to a subject in need of such treatment, the modulator being identified as described herein.

In yet another aspect of the invention, the protease proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with the protease and are involved in protease activity. Such protease-binding proteins are also likely to be involved in the propagation of signals by the protease proteins or protease targets as, for example, downstream elements of a protease-mediated signaling pathway. Alternatively, such protease-binding proteins are likely to be protease inhibitors.

The two-hybrid system is based on the modular nature of most transcription factors, which consist of separable DNA-binding and activation domains. Briefly, the assay utilizes two different DNA constructs. In one construct, the gene that codes for a protease protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a protease-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the protease protein.

This invention further pertains to novel agents identified by the above-described screening assays. Accordingly, it is within the scope of this invention to further use an agent identified as described herein in an appropriate animal model. For example, an agent identified as described herein (e.g., a protease-modulating agent, an antisense protease nucleic acid molecule, a protease-specific antibody, or a protease-binding partner) can be used in an animal or other model to determine the efficacy, toxicity, or side effects of treatment with such an agent. Alternatively, an agent identified as described herein can be used in an animal or other model to determine the mechanism of action of such an agent. Furthermore, this invention pertains to uses of novel agents identified by the above-described screening assays for treatments as described herein.

The protease proteins of the present invention are also useful to provide a target for diagnosing a disease or predisposition to disease mediated by the peptide. Accordingly, the invention provides methods for detecting the presence, or levels of, the protein (or encoding mRNA) in a cell, tissue, or organism. Experimental data as provided in FIG. 1 indicates that protease proteins of the present invention are expressed in the liver, prostate, T cells from T cell leukemia, hepatocellular carcinoma, and lung tumor. Specifically, a virtual northern blot shows expression in the liver, prostate, T cells from T cell leukemia, hepatocellular carcinoma, and lung tumor. The method involves contacting a biological sample with a compound capable of interacting with the protease protein such that the interaction can be detected. Such an assay can be provided in a single detection format or a multi-detection format such as an antibody chip array.

One agent for detecting a protein in a sample is an antibody capable of selectively binding to protein. A biological sample includes tissues, cells and biological fluids isolated from a subject, as well as tissues, cells and fluids present within a subject.

The peptides of the present invention also provide targets for diagnosing active protein activity, disease, or predisposition to disease, in a patient having a variant peptide, particularly activities and conditions that are known for other members of the family of proteins to which the present one belongs. Thus, the peptide can be isolated from a biological sample and assayed for the presence of a genetic mutation that results in aberrant peptide. This includes amino acid substitution, deletion, insertion, rearrangement, (as the result of aberrant splicing events), and inappropriate post-translational modification. Analytic methods include altered electrophoretic mobility, altered tryptic peptide digest, altered protease activity in cell-based or cell-free assay, alteration in substrate or antibody-binding pattern, altered isoelectric point, direct amino acid sequencing, and any other of the known assay techniques useful for detecting mutations in a protein. Such an assay can be provided in a single detection format or a multi-detection format such as an antibody chip array.

In vitro techniques for detection of peptide include enzyme linked immunosorbent assays (ELISAs), Western blots, immunoprecipitations and immunofluorescence using a detection reagent, such as an antibody or protein binding agent. Alternatively, the peptide can be detected in vivo in a subject by introducing into the subject a labeled anti-peptide antibody or other types of detection agent. For example, the antibody can be labeled with a radioactive marker whose presence and location in a subject can be detected by standard imaging techniques. Particularly useful are methods that detect the allelic variant of a peptide expressed in a subject and methods which detect fragments of a peptide in a sample.

The peptides are also useful in pharmacogenomic analysis. Pharmacogenomics deal with clinically significant hereditary variations in the response to drugs due to altered drug disposition and abnormal action in affected persons. See, e.g., Eichelbaum, M. (Clin. Exp. Pharmacol. Physiol. 23(10–11):983–985 (1996)), and Linder, M. W. (Clin. Chem. 43(2):254–266 (1997)). The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes effects both the intensity and duration of drug action. Thus, the pharmacogenomics of the individual permit the selection of effective compounds and effective dosages of such compounds for prophylactic or therapeutic treatment based on the individual's genotype.

The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the protease protein in which one or more of the protease functions in one population is different from those in another population. The peptides thus allow a target to ascertain a genetic predisposition that can affect treatment modality. Thus, in a ligand-based treatment, polymorphism may give rise to amino terminal extracellular domains and/or other substrate-binding regions that are more or less active in substrate binding, and protease activation. Accordingly, substrate dosage would necessarily be modified to maximize the therapeutic effect within a given population containing a polymorphism. As an alternative to genotyping, specific polymorphic peptides could be identified.

The peptides are also useful for treating a disorder characterized by an absence of, inappropriate, or unwanted expression of the protein. Experimental data as provided in FIG. 1 indicates that protease proteins of the present invention are expressed in the liver, prostate, T cells from T cell leukemia, hepatocellular carcinoma, and lung tumor. Specifically, a virtual northern blot shows expression in the liver, prostate, T cells from T cell leukemia, hepatocellular carcinoma, and lung tumor. Accordingly, methods for treatment include the use of the protease protein or fragments.

Antibodies

The invention also provides antibodies that selectively bind to one of the peptides of the present invention, a protein comprising such a peptide, as well as variants and fragments thereof. As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or F(ab')$_2$, and Fv fragments.

Many methods are known for generating and/or identifying antibodies to a given target peptide. Several such methods are described by Harlow, Antibodies, Cold Spring Harbor Press, (1989).

In general, to generate antibodies, an isolated peptide is used as an immunogen and is administered to a mammalian organism, such as a rat, rabbit or mouse. The full-length protein, an antigenic peptide fragment or a fusion protein can be used. Particularly important fragments are those covering functional domains, such as the domains identified in FIG. 2, and domain of sequence homology or divergence amongst the family, such as those that can readily be identified using protein alignment methods and as presented in the Figures.

Antibodies are preferably prepared from regions or discrete fragments of the protease proteins. Antibodies can be prepared from any region of the peptide as described herein. However, preferred regions will include those involved in function/activity and/or protease/binding partner interaction. FIG. 2 can be used to identify particularly important regions while sequence alignment can be used to identify conserved and unique sequence fragments.

An antigenic fragment will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness (see FIG. 2).

Detection on an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

Antibody Uses

The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism and over the course of normal development. Experimental data as provided in FIG. 1 indicates that protease proteins of the present invention are expressed in the liver, prostate, T cells from T cell leukemia, hepatocellular carcinoma, and lung tumor. Specifically, a virtual northern blot shows expression in the liver, prostate, T cells from T cell leukemia, hepatocellular carcinoma, and lung tumor. Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development or progression of a biological condition. Antibody detection of circulating fragments of the full length protein can be used to identify turnover.

Further, the antibodies can be used to assess expression in disease states such as in active stages of the disease or in an individual with a predisposition toward disease related to the protein's function. When a disorder is caused by an inappropriate tissue distribution, developmental expression, level of expression of the protein, or expressed/processed form, the antibody can be prepared against the normal protein. Experimental data as provided in FIG. 1 indicates that protease proteins of the present invention are expressed in the liver, prostate, T cells from T cell leukemia, hepatocellular carcinoma, and lung tumor. Specifically, a virtual northern blot shows expression in the liver, prostate, T cells from T cell leukemia, hepatocellular carcinoma, and lung tumor. If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism. Experimental data as provided in FIG. 1 indicates that protease proteins of the present invention are expressed in the liver, prostate, T cells from T cell leukemia, hepatocellular carcinoma, and lung tumor. Specifically, a virtual northern blot shows expression in the liver, prostate, T cells from T cell leukemia, hepatocellular carcinoma, and lung tumor. The diagnostic uses can be applied, not only in genetic testing, but also in monitoring a treatment modality. Accordingly, where treatment is ultimately aimed at correcting expression level or the presence of aberrant sequence and aberrant tissue distribution or developmental expression, antibodies directed against the protein or relevant fragments can be used to monitor therapeutic efficacy.

Additionally, antibodies are useful in pharmacogenomic analysis. Thus, antibodies prepared against polymorphic proteins can be used to identify individuals that require modified treatment modalities. The antibodies are also useful as diagnostic tools as an immunological marker for aberrant protein analyzed by electrophoretic mobility, isoelectric point, tryptic peptide digest, and other physical assays known to those in the art.

The antibodies are also useful for tissue typing. Experimental data as provided in FIG. 1 indicates that protease proteins of the present invention are expressed in the liver, prostate, T cells from T cell leukemia, hepatocellular carcinoma, and lung tumor. Specifically, a virtual northern blot shows expression in the liver, prostate, T cells from T cell leukemia, hepatocellular carcinoma, and lung tumor. Thus, where a specific protein has been correlated with expression in a specific tissue, antibodies that are specific for this protein can be used to identify a tissue type.

The antibodies are also useful for inhibiting protein function, for example, blocking the binding of the protease peptide to a binding partner such as a substrate. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated with a cell or cell membrane. See FIG. 2 for structural information relating to the proteins of the present invention.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the sample; means for comparing the amount of protein in the sample with a standard; and instructions for use. Such a kit can be supplied to detect a single protein or epitope or can be configured to detect one of a multitude of epitopes, such as in an antibody detection array. Arrays are described in detail below for nucleic acid arrays and similar methods have been developed for antibody arrays.

Nucleic Acid Molecules

The present invention further provides isolated nucleic acid molecules that encode a protease peptide or protein of the present invention (cDNA, transcript and genomic sequence). Such nucleic acid molecules will consist of, consist essentially of, or comprise a nucleotide sequence that encodes one of the protease peptides of the present invention, an allelic variant thereof, or an ortholog or paralog thereof.

As used herein, an "isolated" nucleic acid molecule is one that is separated from other nucleic acid present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5 KB, 4 KB, 3 KB, 2 KB, or 1 KB or less, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a transcript/cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

Accordingly, the present invention provides nucleic acid molecules that consist of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists of a nucleotide sequence when the nucleotide sequence is the complete nucleotide sequence of the nucleic acid molecule.

The present invention further provides nucleic acid molecules that consist essentially of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists essentially of a nucleotide sequence when such a nucleotide sequence is present with only a few additional nucleic acid residues in the final nucleic acid molecule.

The present invention further provides nucleic acid molecules that comprise the nucleotide sequences shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprises several hundred or more additional nucleotides. A brief description of how various types of these nucleic acid molecules can be readily made/isolated is provided below.

In FIGS. 1 and 3, both coding and non-coding sequences are provided. Because of the source of the present invention, humans genomic sequence (FIG. 3) and cDNA/transcript sequences (FIG. 1), the nucleic acid molecules in the Figures will contain genomic intronic sequences, 5' and 3' non-coding sequences, gene regulatory regions and non-coding intergenic sequences. In general such sequence features are either noted in FIGS. 1 and 3 or can readily be identified using computational tools known in the art. As discussed below, some of the non-coding regions, particularly gene regulatory elements such as promoters, are useful for a variety of purposes, e.g. control of heterologous gene expression, target for identifying gene activity modulating compounds, and are particularly claimed as fragments of the genomic sequence provided herein.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the protease peptide alone, the sequence encoding the mature peptide and additional coding sequences, such as a leader or secretory sequence (e.g., a pre-pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the nucleic acid molecule may be fused to a marker sequence encoding, for example, a peptide that facilitates purification.

Isolated nucleic acid molecules can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (antisense strand).

The invention further provides nucleic acid molecules that encode fragments of the peptides of the present invention as well as nucleic acid molecules that encode obvious variants of the protease proteins of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or organisms. Accordingly, as discussed above, the variants can contain nucleotide substitutions, deletions, inversions and insertions. Variation can occur in either or both the coding and non-coding regions. The variations can produce both conservative and non-conservative amino acid substitutions.

The present invention further provides non-coding fragments of the nucleic acid molecules provided in FIGS. 1 and 3. Preferred non-coding fragments include, but are not limited to, promoter sequences, enhancer sequences, gene modulating sequences and gene termination sequences. Such fragments are useful in controlling heterologous gene expression and in developing screens to identify gene-modulating agents. A promoter can readily be identified as being 5' to the ATG start site in the genomic sequence provided in FIG. 3.

A fragment comprises a contiguous nucleotide sequence greater than 12 or more nucleotides. Further, a fragment could at least 30, 40, 50, 100, 250 or 500 nucleotides in length. The length of the fragment will be based on its intended use. For example, the fragment can encode epitope bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50 or more consecutive nucleotides.

Orthologs, homologs, and allelic variants can be identified using methods well known in the art. As described in the Peptide Section, these variants comprise a nucleotide sequence encoding a peptide that is typically 60–70%, 70–80%, 80–90%, and more typically at least about 90–95% or more homologous to the nucleotide sequence shown in the Figure sheets or a fragment of this sequence. Such nucleic acid molecules can readily be identified as being able to hybridize under moderate to stringent conditions, to the nucleotide sequence shown in the Figure sheets or a fragment of the sequence. Allelic variants can readily be determined by genetic locus of the encoding gene.

As used herein, the term "hybridizes under stringent conditions" is intended to describe conditions for hybridization and washing under which nucleotide sequences encoding a peptide at least 60–70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. One example of stringent hybridization conditions are hybridization in 6×sodium chloride/sodium citrate (SSC) at about 45C, followed by one or more washes in 0.2×SSC, 0.1% SDS at 50–65C. Examples of moderate to low stringency hybridization conditions are well known in the art.

Nucleic Acid Molecule Uses

The nucleic acid molecules of the present invention are useful for probes, primers, chemical intermediates, and in biological assays. The nucleic acid molecules are useful as a hybridization probe for messenger RNA, transcript/cDNA and genomic DNA to isolate full-length cDNA and genomic clones encoding the peptide described in FIG. 2 and to isolate cDNA and genomic clones that correspond to variants (alleles, orthologs, etc.) producing the same or related peptides shown in FIG. 2. Twelve (12) SNPs, including 3 indels, have been identified in the gene encoding the protease protein provided by the present invention and are given in FIG. 3.

The probe can correspond to any sequence along the entire length of the nucleic acid molecules provided in the Figures. Accordingly, it could be derived from 5' noncoding regions, the coding region, and 3' noncoding regions. However, as discussed, fragments are not to be construed as encompassing fragments disclosed prior to the present invention.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful as probes for determining the chromosomal positions of the nucleic acid molecules by means of in situ hybridization methods. As indicated by the data presented in FIG. 3, the map position was determined to be on chromosome 19 by ePCR, and confirmed with radiation hybrid mapping.

The nucleic acid molecules are also useful in making vectors containing the gene regulatory regions of the nucleic acid molecules of the present invention.

The nucleic acid molecules are also useful for designing ribozymes corresponding to all, or a part, of the mRNA produced from the nucleic acid molecules described herein.

The nucleic acid molecules are also useful for making vectors that express part, or all, of the peptides.

The nucleic acid molecules are also useful for constructing host cells expressing a part, or all, of the nucleic acid molecules and peptides.

The nucleic acid molecules are also useful for constructing transgenic animals expressing all, or a part, of the nucleic acid molecules and peptides.

The nucleic acid molecules are also useful as hybridization probes for determining the presence, level, form and distribution of nucleic acid expression. Experimental data as provided in FIG. 1 indicates that protease proteins of the present invention are expressed in the liver, prostate, T cells from T cell leukemia, hepatocellular carcinoma, and lung tumor. Specifically, a virtual northern blot shows expression in the liver, prostate, T cells from T cell leukemia, hepatocellular carcinoma, and lung tumor. Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in protease protein expression relative to normal results.

In vitro techniques for detection of mRNA include Northern hybridizations and in situ hybridizations. In vitro techniques for detecting DNA includes Southern hybridizations and in situ hybridization.

Probes can be used as a part of a diagnostic test kit for identifying cells or tissues that express a protease protein, such as by measuring a level of a protease-encoding nucleic acid in a sample of cells from a subject e.g., mRNA or genomic DNA, or determining if a protease gene has been mutated. Experimental data as provided in FIG. 1 indicates that protease proteins of the present invention are expressed in the liver, prostate, T cells from T cell leukemia, hepatocellular carcinoma, and lung tumor. Specifically, a virtual northern blot shows expression in the liver, prostate, T cells from T cell leukemia, hepatocellular carcinoma, and lung tumor.

Nucleic acid expression assays are useful for drug screening to identify compounds that modulate protease nucleic acid expression.

The invention thus provides a method for identifying a compound that can be used to treat a disorder associated with nucleic acid expression of the protease gene, particularly biological and pathological processes that are mediated by the protease in cells and tissues that express it. Experimental data as provided in FIG. 1 indicates that protease proteins of the present invention are expressed in the liver, prostate, T cells from T cell leukemia, hepatocellular carcinoma, and lung tumor. Specifically, a virtual northern blot shows expression in the liver, prostate, T cells from T cell leukemia, hepatocellular carcinoma, and lung tumor. The method typically includes assaying the ability of the compound to modulate the expression of the protease nucleic acid and thus identifying a compound that can be used to treat a disorder characterized by undesired protease nucleic acid expression. The assays can be performed in cell-based and cell-free systems. Cell-based assays include cells naturally expressing the protease nucleic acid or recombinant cells genetically engineered to express specific nucleic acid sequences.

The assay for protease nucleic acid expression can involve direct assay of nucleic acid levels, such as mRNA levels, or on collateral compounds involved in the signal pathway. Further, the expression of genes that are up- or down-regulated in response to the protease protein signal pathway can also be assayed. In this embodiment the regulatory regions of these genes can be operably linked to a reporter gene such as luciferase.

Thus, modulators of protease gene expression can be identified in a method wherein a cell is contacted with a candidate compound and the expression of mRNA determined. The level of expression of protease mRNA in the presence of the candidate compound is compared to the level of expression of protease mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the nucleic acid as a target, using a compound identified through drug screening as a gene modulator to modulate protease nucleic acid expression in cells and tissues that express the protease. Experimental data as provided in FIG. 1 indicates that protease proteins of the present invention are expressed in the liver, prostate, T cells from T cell leukemia, hepatocellular carcinoma, and lung tumor. Specifically, a virtual northern blot shows expression in the liver, prostate, T cells from T cell leukemia, hepatocellular carcinoma, and lung tumor. Modulation includes both up-regulation (i.e. activation or agonization) or down-regulation (suppression or antagonization) or nucleic acid expression.

Alternatively, a modulator for protease nucleic acid expression can be a small molecule or drug identified using the screening assays described herein as long as the drug or small molecule inhibits the protease nucleic acid expression in the cells and tissues that express the protein. Experimental data as provided in FIG. 1 indicates that protease proteins of the present invention are expressed in the liver, prostate, T cells from T cell leukemia, hepatocellular carcinoma, and lung tumor. Specifically, a virtual northern blot shows expression in the liver, prostate, T cells from T cell leukemia, hepatocellular carcinoma, and lung tumor.

The nucleic acid molecules are also useful for monitoring the effectiveness of modulating compounds on the expression or activity of the protease gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The nucleic acid molecules are also useful in diagnostic assays for qualitative changes in protease nucleic acid expression, and particularly in qualitative changes that lead to pathology. The nucleic acid molecules can be used to detect mutations in protease genes and gene expression products such as mRNA. The nucleic acid molecules can be used as hybridization probes to detect naturally occurring genetic mutations in the protease gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the protease gene associated with a dysfunction provides a diagnostic tool for an active disease or susceptibility to disease when the disease results from overexpression, underexpression, or altered expression of a protease protein.

Individuals carrying mutations in the protease gene can be detected at the nucleic acid level by a variety of techniques. FIG. 3 provides information on SNPs that have been identified in a gene encoding the protease protein of the present invention. Twelve (12) SNP variants were found, including 3 indels (indicated by a "-") and 1 SNP in exons, none of which cause changes in the amino acid sequence. As indicated by the data presented in FIG. 3, the map position was determined to be on chromosome 19 by ePCR, and confirmed with radiation hybrid mapping. Genomic DNA can be analyzed directly or can be amplified by using PCR prior to analysis. RNA or cDNA can be used in the same way. In some uses, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., *Science* 241: 1077–1080 (1988); and Nakazawa et al., *PNAS* 91:360–364 (1994)), the latter of which can be particularly useful for detecting point mutations in the gene (see Abravaya et al., *Nucleic Acids Res.* 23:675–682 (1995)). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a protease gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site. Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method. Furthermore, sequence differences between a mutant protease gene and a wild-type gene can be determined by direct DNA sequencing. A variety of automated sequencing procedures can be utilized when performing the diagnostic assays (Naeve, C. W., (1995) *Biotechniques* 19:448), including sequencing by mass spectrometry (see, e.g., PCT International Publication No. WO 94/16101; Cohen et al., *Adv. Chromatogr.* 36:127–162 (1996); and Griffin et al., *Appl. Biochem. Biotechnol.* 38:147–159 (1993)).

Other methods for detecting mutations in the gene include methods in which protection from cleavage agents is used to detect mismatched bases in RNA/RNA or RNA/DNA duplexes (Myers et al., *Science* 230:1242 (1985)); Cotton et al., *PNAS* 85:4397 (1988); Saleeba et al., *Meth. Enzymol.* 217:286–295 (1992)), electrophoretic mobility of mutant and wild type nucleic acid is compared (Orita et al., *PNAS* 86:2766 (1989); Cotton et al., *Mutat. Res.* 285:125–144 (1993); and Hayashi et al., *Genet. Anal. Tech. Appl.* 9:73–79 (1992)), and movement of mutant or wild-type fragments in polyacrylamide gels containing a gradient of denaturant is assayed using denaturing gradient gel electrophoresis (Myers et al., *Nature* 313:495 (1985)). Examples of other techniques for detecting point mutations include selective oligonucleotide hybridization, selective amplification, and selective primer extension.

The nucleic acid molecules are also useful for testing an individual for a genotype that while not necessarily causing the disease, nevertheless affects the treatment modality. Thus, the nucleic acid molecules can be used to study the relationship between an individual's genotype and the individual's response to a compound used for treatment (pharmacogenomic relationship). Accordingly, the nucleic acid molecules described herein can be used to assess the mutation content of the protease gene in an individual in order to select an appropriate compound or dosage regimen for treatment.

Thus nucleic acid molecules displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The nucleic acid molecules are thus useful as antisense constructs to control protease gene expression in cells, tissues, and organisms. A DNA antisense nucleic acid molecule is designed to be complementary to a region of the gene involved in transcription, preventing transcription and hence production of protease protein. An antisense RNA or DNA nucleic acid molecule would hybridize to the mRNA and thus block translation of mRNA into protease protein. FIG. 3 provides information on SNPs that have been identified in a gene encoding the protease protein of the present invention. Twelve (12) SNP variants were found, including 3 indels (indicated by a "-") and 1 SNP in exons, none of which cause changes in the amino acid sequence.

Alternatively, a class of antisense molecules can be used to inactivate mRNA in order to decrease expression of protease nucleic acid. Accordingly, these molecules can treat a disorder characterized by abnormal or undesired protease nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the protease protein, such as substrate binding.

The nucleic acid molecules also provide vectors for gene therapy in patients containing cells that are aberrant in protease gene expression. Thus, recombinant cells, which include the patient's cells that have been engineered ex vivo and returned to the patient, are introduced into an individual where the cells produce the desired protease protein to treat the individual.

The invention also encompasses kits for detecting the presence of a protease nucleic acid in a biological sample. Experimental data as provided in FIG. 1 indicates that protease proteins of the present invention are expressed in the liver, prostate, T cells from T cell leukemia, hepatocellular carcinoma, and lung tumor. Specifically, a virtual northern blot shows expression in the liver, prostate, T cells from T cell leukemia, hepatocellular carcinoma, and lung tumor. For example, the kit can comprise reagents such as a labeled or labelable nucleic acid or agent capable of detecting protease nucleic acid in a biological sample; means for determining the amount of protease nucleic acid in the sample; and means for comparing the amount of protease nucleic acid in the sample with a standard. The compound or agent can be packaged in a suitable container. The kit can further comprise instructions for using the kit to detect protease protein mRNA or DNA.

Nucleic Acid Arrays

The present invention further provides nucleic acid detection kits, such as arrays or microarrays of nucleic acid molecules that are based on the sequence information provided in FIGS. 1 and 3 (SEQ ID NOS:1 and 3).

As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. No. 5,837,832, Chee et al., PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference. In other embodiments, such arrays are produced by the methods described by Brown et al., U.S. Pat. No. 5,807,522.

The microarray or detection kit is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray or detection kit, it may be preferable to use oligonucleotides that are only 7–20 nucleotides in length. The microarray or detection kit may contain oligonucleotides that cover the known 5', or 3', sequence, sequential oligonucleotides which cover the full length sequence; or unique oligonucleotides selected from particular areas along the length of the sequence. Polynucleotides used in the microarray or detection kit may be oligonucleotides that are specific to a gene or genes of interest.

In order to produce oligonucleotides to a known sequence for a microarray or detection kit, the gene(s) of interest (or an ORF identified from the contigs of the present invention) is typically examined using a computer algorithm which starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations it may be appropriate to use pairs of oligonucleotides on a microarray or detection kit. The "pairs" will be identical, except for one nucleotide that preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number between two and one million which lends itself to the efficient use of commercially available instrumentation.

In order to conduct sample analysis using a microarray or detection kit, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray or detection kit so that the probe sequences hybridize to complementary oligonucleotides of the microarray or detection kit. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray or detection kit. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large-scale correlation studies on the sequences, expression patterns, mutations, variants, or polymorphisms among samples.

Using such arrays, the present invention provides methods to identify the expression of the protease proteins/peptides of the present invention. In detail, such methods comprise incubating a test sample with one or more nucleic acid molecules and assaying for binding of the nucleic acid molecule with components within the test sample. Such assays will typically involve arrays comprising many genes, at least one of which is a gene of the present invention and or alleles of the protease gene of the present invention. FIG. 3 provides information on SNPs that have been identified in a gene encoding the protease protein of the present invention. Twelve (12) SNP variants were found, including 3 indels (indicated by a "-") and 1 SNP in exons, none of which cause changes in the amino acid sequence.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments of the Human genome disclosed herein. Examples of such assays can be found in Chard, T, *An Introduction to Radioimmunoassay and Related Techniques*, Elsevier Science Publishers, Amsterdam, The Netherlands (1986); Bullock, G. R. et al., *Techniques in Immunocytochemistry*, Academic Press, Orlando, Fla. Vol. 1 (1982), Vol. 2 (1983), Vol. 3 (1985); Tijssen, P., *Practice and Theory of Enzyme Immunoassays: Laboratory Techniques in Biochemistry and Molecular Biology*, Elsevier Science Publishers, Amsterdam, The Netherlands (1985).

The test samples of the present invention include cells, protein or membrane extracts of cells. The test sample used in the above-described method will vary based on the assay format, nature of the detection method and the tissues, cells or extracts used as the sample to be assayed. Methods for preparing nucleic acid extracts or of cells are well known in the art and can be readily be adapted in order to obtain a sample that is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one of the nucleic acid molecules that can bind to a fragment of the Human genome disclosed herein; and (b) one or more other containers comprising one or more of the following: wash reagents, reagents capable of detecting presence of a bound nucleic acid.

In detail, a compartmentalized kit includes any kit in which reagents are contained in separate containers. Such containers include small glass containers, plastic containers, strips of plastic, glass or paper, or arraying material such as silica. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the nucleic acid probe, containers which contain wash reagents (such as phosphate buffered saline, Tris-buffers, etc.), and containers which contain the reagents used to detect the bound probe. One skilled in the art will readily recognize that the previously unidentified protease gene of the present invention can be routinely identified using the sequence information disclosed herein can be readily incorporated into one of the established kit formats which are well known in the art, particularly expression arrays.

Vectors/Host Cells

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extra-chromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in prokaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

The regulatory sequence to which the nucleic acid molecules described herein can be operably linked include promoters for directing mRNA transcription. These include, but are not limited to, the left promoter from bacteriophage λ, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., *Molecular Cloning: A Laboratory Manual. 2nd. ed.*, Cold Spring Harbor Laboratory Press, Cold Spring Harbor, N.Y., (1989).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., *Molecular Cloning: A Laboratory Manual. 2nd. ed.*, Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, *E. coli, Streptomyces*, and *Salmonella typhimurium*. Eukaryotic cells include, but are not limited to, yeast, insect cells such as *Drosophila*, animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enteroprotease. Typical fusion expression vectors include pGEX (Smith et al., *Gene* 67:31–40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., *Gene* 69:301–315 (1988)) and pET 11d (Studier et al., *Gene Expression Technology: Methods in Enzymology* 185:60–89 (1990)).

Recombinant protein expression can be maximized in host bacteria by providing a genetic background wherein the host cell has an impaired capacity to proteolytically cleave the recombinant protein. (Gottesman, S., *Gene Expression Technology: Methods in Enzymology* 185, Academic Press, San Diego, Calif. (1990)119–128). Alternatively, the sequence of the nucleic acid molecule of interest can be altered to provide preferential codon usage for a specific host cell, for example *E. coli*. (Wada et al., *Nucleic Acids Res.* 20:2111–2118 (1992)).

The nucleic acid molecules can also be expressed by expression vectors that are operative in yeast. Examples of vectors for expression in yeast e.g., *S. cerevisiae* include pYepSec1 (Baldari, et al., *EMBO J.* 6:229–234 (1987)), pMFa (Kujan et al., *Cell* 30:933–943(1982)), pJRY88 (Schultz et al., *Gene* 54:113–123 (1987)), and pYES2 (Invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf9 cells) include the pAc series (Smith et al., Mol. *Cell Biol.* 3:2156–2165 (1983)) and the pVL series (Lucklow et al., *Virology* 170:31–39 (1989)).

In certain embodiments of the invention, the nucleic acid molecules described herein are expressed in mammalian cells using mammalian expression vectors. Examples of mammalian expression vectors include pCDM8 (Seed, B. *Nature* 329:840(1987)) and pMT2PC (Kaufman et al., *EMBO J.* 6:187–195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance propagation or expression of the nucleic acid molecules described herein. These are found for example in Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual. 2nd, ed., Cold Spring Harbor Laboratory*, Cold Spring Harbor Laboratory Press, Cold Spring Harbor, N.Y., 1989).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the peptide is desired, which is difficult to achieve with multi-transmembrane domain containing proteins such as proteases, appropriate secretion signals are incorporated into the vector. The signal sequence can be endogenous to the peptides or heterologous to these peptides.

Where the peptide is not secreted into the medium, which is typically the case with proteases, the protein can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of Vectors and Host Cells

The recombinant host cells expressing the peptides described herein have a variety of uses. First, the cells are useful for producing a protease protein or peptide that can be further purified to produce desired amounts of protease protein or fragments. Thus, host cells containing expression vectors are useful for peptide production. Host cells are also useful for conducting cell-based assays involving the protease protein or protease protein fragments, such as those described above as well as other formats known in the art. Thus, a recombinant host cell expressing a native protease protein is useful for assaying compounds that stimulate or inhibit protease protein function.

Host cells are also useful for identifying protease protein mutants in which these functions are affected. If the mutants naturally occur and give rise to a pathology, host cells containing the mutations are useful to assay compounds that have a desired effect on the mutant protease protein (for example, stimulating or inhibiting function) which may not be indicated by their effect on the native protease protein.

Genetically engineered host cells can be further used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a protease protein and identifying and evaluating modulators of protease protein activity. Other examples of transgenic animals include non-human primates, sheep, dogs, cows, goats, chickens, and amphibians.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the protease protein nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence(s) can be operably linked to the transgene to direct expression of the protease protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems that allow for regulated expression of the transgene. One example of such a system is the cre/loxP recombinase system of bacteriophage P1. For a description of the cre/loxP recombinase system, see, e.g., Lakso et al. *PNAS* 89:6232–6236 (1992). Another example of a recombinase system is the FLP recombinase system of *S. cerevisiae* (O'Gorman et al. *Science* 251:1351–1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. *Nature* 385:810–813 (1997) and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

Transgenic animals containing recombinant cells that express the peptides described herein are useful to conduct the assays described herein in an in vivo context. Accordingly, the various physiological factors that are present in vivo and that could effect substrate binding, protease protein activity/activation, and signal transduction, may not be evident from in vitro cell-free or cell-based assays. Accordingly, it is useful to provide non-human transgenic animals to assay in vivo protease protein function, including substrate interaction, the effect of specific mutant protease proteins on protease protein function and substrate interaction, and the effect of chimeric protease proteins. It is also possible to assess the effect of null mutations, that is mutations that substantially or completely eliminate one or more protease protein functions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

The invention claimed is:

1. An isolated polypeptide consisting of the amino acid sequence SEQ ID NO:2.
2. An isolated polypeptide comprising the amino acid sequence SEQ ID NO:2.
3. A composition comprising the polypeptide of claim 1 and a carrier.
4. A composition comprising the polypeptide of claim 2 and a carrier.

* * * * *

SEQUENCE LISTING

<160> NUMBER OF SEQ ID NOS: 16

<210> SEQ ID NO 1
<211> LENGTH: 1615
<212> TYPE: DNA
<213> ORGANISM: HUMAN

<400> SEQUENCE: 1

```
tgggcacctg gttgttcaca cggcagggga ggaacagccc tgtcaactgc tggccccggg      60
aaactgggcc tggggaggac atgcttgggc ataataagtt agccctgggg gcagggcaga     120
gctggcctcg ggcccagacc ctgccgcaat gaggacaggc ctggctgtgg ccccagcatg     180
gtgtctgttg caggtggccg gactgtgcca tgctgctcca gacccaaggt ggcagctctc     240
actgcgggga ccctgctact tctgacagcc atcggggcgg catcctgggc cattgtggct     300
gttctcctca ggagtgacca ggagccgctg tacccagtgc aggtcagctc tgcggacgct     360
cggctcatgg tctttgacaa gacggaaggg acgtggcggc tgctgtgctc ctcgcgctcc     420
aacgccaggt agccggact cagctgcgag gagatgggct tcctcagtga ttgccccaga     480
ggccgttcct tggccgccat ctgccaagac tgtggccgca ggaagctgcc cgtggaccgc     540
atcgtgggag ccgggacac cagcttgggc cgtggccgt ggcaagtcag ccttcgctat      600
gatggagcac acctctgtgg gggatccctg ctctccgggg actgggtgct gacagccgcc     660
cactgcttcc cggagcggaa ccgggtcctg tcccgatggc gagtgttcc cggtgccgtg      720
gcccaggcct ctccccacgg tctgcagctg ggggtgcagg ctgtggtcta ccacgggggc     780
tatcttccct tcgggaccc caacagcgag gagaacagca acgatattgc cctggtccac     840
ctctccagtc ccctgcccct cacagaatac atccagcctg tgcctccc agctgccggc      900
caggccctgg tggatggcaa gatctgtacc gtgacgggct ggggcaacac gcagtactat     960
ggccaacagg ccgggtact ccaggaggct cgagtcccca taatcagcaa tgatgtctgc    1020
aatggcgctg acttctatgg aaaccagatc aagcccaaga tgttctgtgc tggctacccc    1080
gagggtggca ttgatgcctg ccaggggcgac agcggtggtc cctttgtgtg tgaggacagc    1140
atctctcgga cgccacgttg gcggctgtgt ggcattgtga gttggggcac tggctgtgcc    1200
ctggcccaga agcaggcgt ctacaccaaa gtcagtgact ccgggagtg gatcttccag     1260
gccataaaga ctcactccga agccagcggc atggtgaccc agctctgacc ggtggcttct    1320
cgctgcgcag cctccaggc cgaggtgat cccggtggtg ggatccacgc tgggccgagg     1380
atgggacgtt tttcttcttg ggcccggtcc acaggtccaa ggacaccctc cctccaggt    1440
cctctcttcc acagtggcgg gcccactcag ccccgagacc acccaacctc accctcctga    1500
cccccatgta aatattgttc tgctgtctgg gactcctgtc taggtgcccc tgatgatggg    1560
atgctcttta aataataaag atggttttga ttaaaaaaaa aaaaaaaaaa aaaaa          1615
```

<210> SEQ ID NO 2
<211> LENGTH: 376
<212> TYPE: PRT
<213> ORGANISM: HUMAN

<400> SEQUENCE: 2

```
Met Val Ser Val Ala Gly Gly Arg Thr Val Pro Cys Cys Ser Arg Pro
 1               5                  10                  15

Lys Val Ala Ala Leu Thr Ala Gly Thr Leu Leu Leu Leu Thr Ala Ile
            20                  25                  30
```

-continued

Gly Ala Ala Ser Trp Ala Ile Val Ala Val Leu Leu Arg Ser Asp Gln
             35                  40                  45

Glu Pro Leu Tyr Pro Val Gln Val Ser Ser Ala Asp Ala Arg Leu Met
 50                  55                  60

Val Phe Asp Lys Thr Glu Gly Thr Trp Arg Leu Leu Cys Ser Ser Arg
 65                  70                  75                  80

Ser Asn Ala Arg Val Ala Gly Leu Ser Cys Glu Glu Met Gly Phe Leu
                 85                  90                  95

Ser Asp Cys Pro Arg Gly Arg Phe Leu Ala Ala Ile Cys Gln Asp Cys
             100                 105                 110

Gly Arg Arg Lys Leu Pro Val Asp Arg Ile Val Gly Arg Asp Thr
             115                 120                 125

Ser Leu Gly Arg Trp Pro Trp Gln Val Ser Leu Arg Tyr Asp Gly Ala
 130                 135                 140

His Leu Cys Gly Gly Ser Leu Leu Ser Gly Asp Trp Val Leu Thr Ala
145                 150                 155                 160

Ala His Cys Phe Pro Glu Arg Asn Arg Val Leu Ser Arg Trp Arg Val
                 165                 170                 175

Phe Ala Gly Ala Val Ala Gln Ala Ser Pro His Gly Leu Gln Leu Gly
             180                 185                 190

Val Gln Ala Val Val Tyr His Gly Gly Tyr Leu Pro Phe Arg Asp Pro
             195                 200                 205

Asn Ser Glu Glu Asn Ser Asn Asp Ile Ala Leu Val His Leu Ser Ser
 210                 215                 220

Pro Leu Pro Leu Thr Glu Tyr Ile Gln Pro Val Cys Leu Pro Ala Ala
225                 230                 235                 240

Gly Gln Ala Leu Val Asp Gly Lys Ile Cys Thr Val Thr Gly Trp Gly
                 245                 250                 255

Asn Thr Gln Tyr Tyr Gly Gln Gln Ala Gly Val Leu Gln Glu Ala Arg
             260                 265                 270

Val Pro Ile Ile Ser Asn Asp Val Cys Asn Gly Ala Asp Phe Tyr Gly
             275                 280                 285

Asn Gln Ile Lys Pro Lys Met Phe Cys Ala Gly Tyr Pro Glu Gly Gly
 290                 295                 300

Ile Asp Ala Cys Gln Gly Asp Ser Gly Gly Pro Phe Val Cys Glu Asp
305                 310                 315                 320

Ser Ile Ser Arg Thr Pro Arg Trp Arg Leu Cys Gly Ile Val Ser Trp
                 325                 330                 335

Gly Thr Gly Cys Ala Leu Ala Gln Lys Pro Gly Val Tyr Thr Lys Val
             340                 345                 350

Ser Asp Phe Arg Glu Trp Ile Phe Gln Ala Ile Lys Thr His Ser Glu
 355                 360                 365

Ala Ser Gly Met Val Thr Gln Leu
 370                 375

<210> SEQ ID NO 3
<211> LENGTH: 21784
<212> TYPE: DNA
<213> ORGANISM: HUMAN
<220> FEATURE:
<221> NAME/KEY: misc_feature
<222> LOCATION: (1)...(21784)
<223> OTHER INFORMATION: n = A,T,C or G

<400> SEQUENCE: 3

-continued

```
ctgggaataa atccctttt cctgtgccac caggcctccc cagctggccc cagccttggt      60
tcccactacc ttccccaagc tctggccatc tggccatctc gatggcctct ccagcctctg    120
acataagaga gcctgcttat tcttgcctca aggcctttgc ctgtgctgtt ccctctgccc    180
acagtgccct tccttgtggt ctgtgtgtgg ctggcacctc acctttcaga gcttagctca    240
gaagtctcct ctaggggagg ccctgtgatc cctgatcccc tgcagaagcc cacctgctgc    300
cccagcctgc acggttttct tcacagcctc tgccacaatc tggaaattat tgggttcatt    360
tacttgtttc cttgttaatg tctcccactc cccacctaca cgcatgagaa cgtgaacccc    420
tgagagtcgt aaccttatct gtcttctttg ggttatgttc ccggaaccta gaaaggtgcc    480
aagcacacag cggatgttca gtaggatggt aaacaaataa agcttcttta ggctgatgaa    540
aaaactgagg gtcaggcgcg gtggctcacg cctgcaattc caacactttg tttgggaggc    600
tgagacaagc agataacttg agtctgggag ttcacgacca gcctggtcaa catggcaaac    660
cccgtcaata caaaaaatac aaaaattagc catgtgtggt ggtgtgcgcc tataatccca    720
gctactcggg aggctcagaa ttacctgagc ctgagcgctt gagactgcag tgtgccatga    780
tcgcgccgct gcactccagc ctgggcagca cagtgaaacc ctgtctcaaa aaaaaaaaa    840 agaaaaagaa aggagagaga gagagaagaa agaaagaaag aaagaaagaa agaaagaaag    900
aaagaaagaa agaaaaaagg aaggaaggaa ggaaggaaaa gaaaaaaact gaggctgagg    960
ctcagagagg ggaggggagt tgctcaggcc cacacatctc tgatgattta taaagcattt   1020
atagagaact tgctatgtgc caggcacttc cgcacagtga gagccaggat ggcttcgtgg   1080
ctgtacacag gggacctggc atcaaacctg cccagggttc tggacgctgc tctgcctctt   1140
ccaggctgtc actgtgggca cgtgaccccca cttctctgag ctatctcaaa aacaggaatc   1200
atagttgtgg gattgaaata aggactaaat gagctgatgt atttagaacg gtgcttagca   1260
cctggaggca tcaatacaat ttgagctatt cttcttcttc ttgaaaataa ctttaaatta   1320
ttatttttag aagtaggtgc tcagtggatg cccatttaat agataagaaa gttgaggctc   1380
aaagatatga tggcacctgc cttaggttcc agctaggaag gggtagggtc aatattttta   1440
aatgaggctg ccagacgca gtggctcact cctgtaatct cagcattttg ggaggctgag   1500
gaaggaagat cgcttcagcc caggagtttg agaccagcct gggcaacata gcaagaccac   1560
gtcgctaaaa aaattaatac ataaaataaa atgaggctgg cagattttca agtggagggg   1620
caaatttgat cttgcaactg gtaccatga gagaggtctg atttaggggg tatctagggg   1680
caaagcatct agaacagcag aaacgactga ggcagcgagg aaatgccagc ggcagggaag   1740
agagctacca agagggcaaa ggttgggggt cacagtccca agaagagatg cccaaagca   1800 aagacagaaa tacaaaagca cagtgtcact ggggaggaga cattccctaa gtgccccaag   1860
gaaaacgtga caggcggtcg ggannnnnnnn nnnnnnnnnn nnnnnnnnnn nnnnnnnnnn   1920
nnnnnnnnnn nnnnnnnnnn nnnnnnnnnn nnnnnnnnnn nnnnnnnnnn nnnnnnnnnn   1980
nnnnnnnnnn nnnnnnnnnn aataagttag ccctgggggc agggcagact ggcctcgggc   2040
ccagaccctg ccgcaatgag gacaggcctg gctgtggccc cagcatggtg tctgttgcag   2100
gtggccggac tgtgccatgc tgctccagac ccaaggtggc agctctcact gcggggaccc   2160
tgctacttct gacagccatc ggggcggcat cctgggccat tggtgagagc ggttcctgtg   2220
cctctgacct cccctggccc ctgcagcctc cagcctgcct gccctcaccc ctcccttctc   2280
tgcagtggct gttctcctca ggagtgacca ggagccgctg tacccaggtg agtggagcag   2340
gctgggaccc tctgggggag ccctggagga cacgtgtatc tggcgggagc tcaacaagcg   2400
```

-continued

```
tatttgttga ataaatgcac aaatgcatgc agaaatgcta atcataatag tgcatttgta    2460
ttgagtgcct gctatgtacc aggcactatt ctaagcaccc cacatgtcta acccagactt    2520
tttcagacac cagtgtatta ctcatgagtg cctcataaaa ttaaattagt gagttggaaa    2580
accatgtttt tttttaagt atgaaataga ttcgattaca gactatcaca gtacatctct     2640
cagtaagtaa aggttatgct aattttgtt tgttttttt tttttgcat ccatatacat       2700 gtaatcccac tgcatcccca cactctgagg gtgggactgt tattctccct gttttacaga    2760
tggggaaact gaggctttga gcaatgcggc agtttgcccc agactacaga gctatgggct    2820
acatcaggat gtaaaaatgt gtttcttact gcgtggcatg gtgaaaacat gttggggagg    2880
catgatataa attcagtgga cccttctaac tctcctagga ggtagttttt ttgtttgttt    2940
gttttaaaaa agaaaaaagt cttgctctgt cacccaggct agagtgcaat ggtgcagtct    3000
cagctcaccg caacctctgc ctcccaggtt caagcgattc tcctgcttca gcctcccaag    3060
tacctgggaa tacaggcgtg tgccaccatg cccagttaat ttttgtatt tttagtagag     3120 atgagatttc accatgttgg ccaggacggt ctcgatctcc tgaccttgtg atccacccgc    3180
ctcagcctcc caaagtgctg ggattacagg catgagccac tgcgcctgtc cctggtatta    3240
gctccatttt acagatgtgc aaaatgagga ccagagagga catgcagctg ggaacgagg     3300 ggccaggaac agctcttaga cttatccact gtaagtgtgt ctgcaggcat gtggaatgaa    3360
tggccacaca aataaataga taaagaaact aactgtggga tgaatgaatg aatcttccca    3420
aatgccaact tcaagctgcc attccctgat gcaggacagc aggaaaaaag gggaagttgg    3480
gtggtgggat gtattttca tgtctgtgag cctcatctaa ttccataaag gattcagttc     3540
acactaaaat cagaaatgaa aatccagaca agaaaagcca acatcaacat taatcatcat    3600
taccagcact tagcatttgt atgcaccagc caaggccttg ggaccttatg atatcaactc    3660
attaagtctt cccaacaacc tgttgttttt ctttctttt ttttctttt ctttctttct     3720 ttcttttttt tttttttttt ttgagatggg gtcttgctct gtcgcccagg ctggagtgca    3780
gtgacacgat cttagctcat tgtaacctac atctcctggg ctcaagcaat cctcccatct    3840
cagccttctg agtagctggg actataggct aatgccacca tgcctacaca aaattatttt    3900
gtcaataaca aattattgtt atttttatct ttttgagcca gagtctcgct gtgtcgccca    3960
ggcaggagtg ctgtggcgcg atcttggctc actgcaatct ccatctccca ggttcaagtg    4020
attctcctgc ctcagcctcc tgagtagcta ggactacagg cacgtgccac cacacccagc    4080
taatttttgt attttagta gaggcgggt ttcaccatgt tggccaggat ggtctcaaac       4140
tcctgacctc aggtgatcca cccgtctcgg cctcccaaag tgctgggact acaggcatga    4200
gccaccacac ccaacctcat tttttaaatt tttagtagag atgggatctt gctacattgc    4260
ccagtctgat cttgaactcc tgagctcaaa gcagtcctct cagatcagcc tcccaaagtg    4320
cagggattac aggtgtgcac caccacaacc catttttccta tggggatgct gaggcacaga    4380
aaggctgagt gacttgcccc aggtcatgga gctagtcagt gtcagggctg ggatttgaac    4440
ccaggcagcc tgcgtagtaa ctgtatatag tgtctacact tgattgcttg ttaaaaaaaa    4500 aaaaagaac agctgaattc attgccatag taaagactga catatgccag gccctggcgg    4560
cagcctttac ccagcaggcc tatgaagtta gggctgttac atcccaacat tttgcatttg    4620
ggggaaattg agtcccagtg aagcaaactg acttgcccga ggctgaccac acatcagaga    4680
cagagcgaag ggatcacgcc cctgtcaaaa gcccctccgt gacaacacgt ggcattgaga    4740
```

```
taaaatccca acccatcaca ggctccaagc ctcctagtgt ggaggcccct ctccaccccc    4800
acctcacact ggcttctagc accctcaggg cccagtccct tgctcaaatg acctgctcac    4860
acagaagtct ctactcaccc acttctttct agctcacacc cagaggcaga tttcagttct    4920
gcacagttcc ttctgagctg tggggcctcc caccagtccc tactctctcc aagactcaat    4980
ttcctcatct gtgagatggg ggtaagaaga atcagtggga ataagaggag ataaaaatct    5040
gtgtagtact tgggcggggt gcggtggctc acccctgtaa tcccagcact ttgggaggcc    5100
gaggcaggca gatcacctga ggtcaggagt tcgagaccag cctggccaac gtggtgaaac    5160
ctcatctgta ctaaaaacac aaaaattggc caggcgtggt ggcgggcgcc tgtaatccca    5220
gctactcagg aggctgaggc aggagaactg tttgaacctg ggaggcgcgg gttgcaggtt    5280
gcagtgaact gagatcacgc cactgcactc cagcctgggt gacagagcaa gagtctgtct    5340
caaaaaaaaa aaaaaaaaaa aggctgtgca gtacttgcct cttagccagc acagtggaca    5400
ttggcttttg tatctcactc ctgaaattct ttcttgaaat ttcttgagca agatcttcct    5460
ggacttccag actctatggc ctctcaccct atggtgtgtc cctgccaccc cggtaaaacc    5520
ctcctcactc attgtgaatt atttactcct ggcgaactcc aggaaggcag ggaccttttg    5580
tggtcagacg gtgcctggca catagtaggt tctcaggaaa tccttgagtt atgagtgcac    5640
ccaaagccaa aacactggga tgaactagag agtcatgggc ctccagctgg aaaggagcga    5700
ggccaccact cacaaccggc tctggccagc accacgccgc caccctgcag aggtatttgg    5760
gtttttcaac aactcaggga aatgatgaaa caaacaaaca aacaaaaaca accccaagct    5820
tgtatcccca cctcgctttt ttttttcctgg gattttcaca cttctaaata tatccaacaa    5880
cttggcaggc acaccaggtg acccagaaca tccttttttgt gttgcctgaa atgataggaa    5940
caagaataaa gaatttaaaa gtgagaaaca gcagcagaga gtgtgacttt aaaaatagcc    6000
agaggggaca tttgatgttc tctccccact cccatctccc caacacaca tctataaagt    6060 gattttcccc cctaaaacct cacactttct ggaaatcaca tttccagagc agttaacagt    6120
cattttaaaa taagaatcca cccctcttcc tgccccagct ggtgtttcaa actccaagcc    6180
ttggctttca tggggtgatg aggaccccccc agctagaggt gccaggcatt ccctgcccca    6240
accccagagc aggagaccgt aattaaggca ggccaggccg gtgcggtggc tcacgcctgt    6300
aatcccagca ctttgggagg cccaaatggg cagatcactt gaggtcagga gaccagcctg    6360
gccaacatgg caaaacccca tctctactaa aaatacaaaa attagccggg cgtggtggct    6420
ggtgcctgta atcccagcta tttgggaggc tgaggcatga gaatcgcttg aactcaggag    6480
gcagaggttg cagtgagctg agatcgtgcc actgcactct agcctgggag acagagcaag    6540
actccatctc aaaacaaact taaaatagaa taaaataaaa taagaatccg cccccctccc    6600
cgccccagtt ggtgtttcaa accctgagac ttggccttgg aattcatggg gtgatgagga    6660
ccccacagcc agaggtgcca ggcgttccct gccccaaccc cagagcagga ggccatcatt    6720
aaggcaggcc agccaggtgg cttttcagtg ccagccgtag ctgaatatat taggcaggga    6780
gacaggcaag ggtttgtatg agacccacag aaggaacagg gaatatgctg gtctgggttc    6840
aagtcccggt tttgctggtt agccgtgtgc ctctgggcaa gtttattcct ctgaggctta    6900
gttttcccat ctgtaagatg ggcatagaag tggtcactac tggctgggca cagtggctca    6960
cgcctgtaat cccagcactt ggggaggcca aggcaggtgg atcacctgag gccagaagtt    7020
cgagaccagc ctggccaaca tggtgaaacg ctgtttctac taagaacaca aaagttagcc    7080
aggtgtagta gcatgtgcct gtaatcccag ctactcggga ggctgaggca ggaggatcgc    7140
```

```
ttgaacctgg gaggcagagg ttgcagtgag ccgagatcat gccactgcac tccagcctga   7200
gcaacagagc aagattatgt ctcaaaaaaa aaaaaaaaa ccgaagtggt cactatctcc   7260
gaggatggtt gtgggattca gagagccact tggataggat gcatagcatg gggccagccc   7320
actgacaccc cccagtaaac gtagccagtg ctattattac tgtgctgttg tttaaccctc   7380
cagaggggaa gtctcttgag aggctgtcca gggcaatgtt aaaagcttgg ggtttgaagt   7440
cactcagacc tgatttcgaa tcctctctcc ctgcttctcg tgcatttggt gacgttgggg   7500
aagccacccc acctctctga gcctcagctt ccccgtctgg aatttgggga tgatcttcgt   7560
ggctcctggg gtgtgcgacg aggccttggt tgatggtggg gcagaggtag cctagcccca   7620
ggaacacagt aggtcctcag ctggggagag ttctacttgg aagtcttgct tctccttgtc   7680
ccaacctgcg gggctgtggg aagacccctc agctggtgtg tggcctcacc aggttccttc   7740
taagaggatg caaaagcaag ttttcatttg actcggtttc ccagaatgtg ctctcagagc   7800
ccaggccagg caggaggctc ttgagaaaag gacaaaaaga catggtggct cacacctgcc   7860
atcccagcac tttgggaggc caaggtggga ggattgcttg aggccaggag tttgagatca   7920
gcctggacaa tatagcaata ccctgtctct acagaaaaaa ataaatttaa aaggcgtttt   7980
tagctcaggc tttgctgggt tctaacctgg ctattgtcac tcagctttat cctaacataa   8040
aaaaataaac aaattagcag ggtgtggtgg tatgcccctg tggtcctagc tacttgggag   8100
gttgaggcgg gaggatcgtt tgagcccagg aggttgaggc tgcaatgagc tatgatcgtg   8160
ccactgcact ccagcctggg tggtggagcg agacccgtc tcaaaaaga aaaaaaaaa    8220 gtggcaggga gaaggaaagg aaaggacaaa gaggttcaca gctgatctct ccctgaacct   8280
gctccttccg tccccatctc tgtcagcccc atcttttcag gctcaggcca aacccctcgg   8340
ttaccctccc agttcctcca gtcacccatg aatcagatct gcaggaaac cctgtcagct    8400 gcacctacag aacctctcca aaatctgaac tcttctcccc gtccactgcc ccacccctgc   8460
tccagccccc ttccctccc ctctggacat cccagagcct cctccctggc ctccctgctc    8520
ccatccctgc cccccaatca tatcccacaa aggggatatg actcactcac ttaaccggca   8580
attctggagg gtcttaaaac ctggctgcct caagaggctt taaaatgtta tcagatgggg   8640
gccaggtaca gtggctcatg ctggttcccc acttgcagcc agaggagct ggtgaccacc    8700 tgagtcaggt cagggccctc cctggctgc acctcacacc aggtgccagc aaagccctga    8760
tgttgctcta tttctagctc ccacctgatc tgccctccc tggctcactc tgctctggcc    8820
tcccactgtt cctggagcac tccccccagt ccccacacc agccttggga tctttgcatc    8880
tgcaagtccc tctgtctccg tgctgatctc acacacctcc tgacactttc tcacctcctg   8940
caggtctttg ttcctgcacc accttcccag ggacgctctc cttgcagcga ctgaaaagtg   9000
caacctcacc ccaccctcca caccggcact cccctccctc ggtggcattt tattttctc    9060 tgtggcccct tcctatcttg tgacacataa tatatcctac ttatttgtcc ctttcttgat   9120
ttgtctcacc tactgagctt tgagttccac aggggtcggg gttttttgtct gatttgttca   9180 ttgcagtggt gatttgttca ctgcctaaaa tagagcctgg caggtacaaa gtgtttggta   9240
aatagaaatc aataccccag ggtctgtgac ctgacttagg tgttaacagg ttcctctgag   9300
gtgtgtgggg aacagactga ggggtttcag gggacatctg ttctcaccac aaattgcccc   9360
ccaaccagcc ccagacatga acagtctccc gggagctccc tctagccttc tcgtatatcc   9420
cagccctgcc tcatgtcaca atttgtaatg atgtgtttgg ctgggtgaca ttttatggcc   9480
```

```
atctgtctcc ctatccccta taatgtggtt tgccgaaagc aaagcccagg actgtctcgg    9540
ccatctgtgt ctccaggatc acccctcact gggcatggag tatgtgtcca gttaacgctt    9600
gctgagtgaa tgaatgaata ctccatcctc tgcctggaga attacgcact ttagcatatc    9660
caaggctctg acaagtcctg cataaaagag cattattgtt ttctttcttt ctttccttct    9720
ttccctcttc ttttctttct gactatagga tattgattat caatctggca atagtcaaga    9780
ttggcagtct ggtgtattag tcaaaggttt tcagcctaca aaagacaaaa agaaaaaata    9840
aactggctaa aaacaaaagg ggatatgatt tactaactca cttaaccgac agtcacagag    9900
gttcttcaaa cctggctgta tcaaggggct ttaaaatgtt atcagatggg ggccaggtgc    9960
agtagctcac gcctgtcatc cagcactttg ggaggccaag acaggcagat cacttgaggt    10020
caggagttcg agaccagcct ggccaacatg gtgaaacccc gtgtctacta aaatacaaa    10080 aaattagcca gtgtggtgg catgtgtctg tagctccagc tactcgggag gctgaggcag    10140
gacaatggct tgaatccggg aggcggaggt tacagtgacc caaggttgca ccagtgcatt    10200
ccagcctggg tgacagagcg agactctgtc tcaaaaaaaa aaaaaagtt atcagatggg    10260 aaatgaattc cgatattaaa aattgatatg tatttatact atattattaa agttattttt    10320
cataaaacat agaagggtaa gtttaagaaa tgagaagtat ttataccaaa atgattaaat    10380
attatttaat ttaaagatat aaatgtcttg ttggacaaaa aattcaaaat ttccattaga    10440
caggaaaaat aagttcaaga gatatattga acaacatggt gattatagtt aataacaata    10500
tattatatac ttgaacattg ctaaaagata ttttaagtgt tctcaccaca cacaaagggt    10560
agtgcatgtg ttaattagct tgatttagcc gttccacaac gtatacatat ttcacatcat    10620
cttgtacacc atcaatgtat ataattttgt caattaaaat aaatacatat tttaaggccg    10680
ggtgcagtgg ctcacaccta taatcgcagc actttgggag gccgaggcag gcagatcacc    10740
tgaggtcagg agtttgagac tagcctggcc aacatggtga acccccattc tctacttaaa    10800
atacaaaaaa attagctggg catggtggtg catgtctgta atcccagcca ctcgggaggc    10860
tgaggcagaa gaatcgcttg aacccgggag gcagaggttg cagtgagctg agattgcacc    10920
actgcacacc agcctggaca acagaagtga gactccgtct caaaaaaata aataaataaa    10980
aataaaataa atacatatat attttttgaga tggagtctca ctctgtcgcc caaactggag    11040
tgcagtggca cgatcttggc tcactgcaac ctctgctgcc caggttcaag caattctcct    11100
gcctcagcct cccgagtagc tgggattaca ggcacctgcc atcatgcctg gctaattttt    11160
gtagttttca tagagacgag gtttcatcat cttggccagg ctggtcttga actcctgacc    11220
ttgtgatcca cccatctcgg cctcccaaat aaatacatat tttaaaagat agaaatcact    11280
ctggaaggag agttaatctg tttgatataa taataatata ttaatattat attataacaa    11340
tatattagta tttatattcta ataatatatt aatattatat taatataata tattattata    11400
ttataacaat atattaatat tatattataa caatatatta atattatatt atgtaataat    11460
actactactc catatagcta tggaaaagtt catatgaaga aaccaggcta tgatctacaa    11520
actggcaaca aatttgttct tctatttttcc atatgctgtc tgtgtacgta taaagtgaga    11580
ggtcttttta tatgagttaa gggtgtgacc aaagacaaat ggaaaagac aaatgacaaa    11640 catactaata aagagcttcg gtttctccac aaaaaataca ataataaaat aaaatgttat    11700
cagaaatctc ttgactctcc tccacgttag ctcactttt ccctcaagag ggtgaacatg    11760
acccttaaca gatccagcct caagtgctgg attctcttgg gaacttggtt aaatggtttt    11820
ttttcttccc gaatgtccaa gtcaccttcc agacctgcag ctcctgagca gccaacttag    11880
```

-continued

```
gacttctaat ggagagtgaa gttcccctgg ttcgcggagg ggccggccac agcctcaagg    11940
ctgctgttga ttggtccgac ctgagtcctt gagtctggca gagtgccatg gtgctctgta    12000
atcccacctg taatcccagc attttaggag gcagaggcag gaagattgct tgagcctagg    12060
agttcaagac cagcctgggc aacatagcaa gacccgtctc tacaaaacaa acaaaacaa     12120 aacaaacaaa caaaaaaatt agccaggtgt ggtggtgcac gcctgtggtc ctagctactc    12180
aggaggttga ggtaggagga tttcttgagt ctgggaggtc aaggctacag tgagccaaga    12240
tcacaccact acactccagc ctgggcaaca gagcgagacc ctgtctttaa aaaaaaaag    12300 tccttgagtc atgattccag atgcaatcgc agatgtgggg gctgcaaccc tccgatgggc    12360
tggggttcac gtctacacca catgctgga gcacaggcca ggaggggctc cggctgggga    12420
agcatgtggg gagcctggct gtgggaccca ggcggccccg ggccctgtcg ccctgcagtg    12480
caggtcagct ctgcggacgc tcggctcatg gtctttgaca agacggaagg gacgtggcgg    12540
ctgctgtgct cctcgcgctc caacgccagg gtagccggac tcagctgcga ggagatgggc    12600
ttcctcaggt actgggggcc ctcggagggg tgggagccgg gaggggctgg ggagcaggcc    12660 taaccctgc cccgcccagg gcactgaccc actccgagct ggacgtgcga acggcgggcg    12720
ccaatggcac gtcgggcttc ttctgtgtgg acgaggggag gctgcccac acccagaggc     12780 tgctggaggt catctccgtg tggtgaggag ggcagcgggc aggtggggca cacctcaga    12840 cccccaaggc actccctctc ccgttttcc ttccacctgt cttaactggt ctctatttcc     12900
tttctttctg tgtctccaat cccatctctc ccagtgattg cccagaggc cgtttcttgg     12960 ccgccatctg ccaaggtgag atcctaaaac tcagaaccct ctcctttagg cccttgggga    13020
ggccacgtcc cctcaagctc cccaggatgg ggccatgtac tttcagaccc cctagggcag    13080
ggccaagcct gggctctggg gacctgggct ccagtccct gtcgccgccc cctgctgacc      13140
cttgtcccac agactgtggc cgcaggaagc tgcccgtgga ccgcatcgtg ggaggccggg    13200
acaccagctt gggccggtgg ccgtggcaag tcagccttcg ctatgatgga gcacacctct    13260
gtgggggatc cctgctctcc ggggactggg tgctgacagc cgcccactgc ttcccggagt    13320
gagtgccccc caatggcgct gatgatgggg aggcagagga gcggagagac agtggggagg    13380
agggcggatt gtgcccaggc aggtggccac cctccacccc tttccctggt aggcggaacc    13440
gggtcctgtc ccgatggcga gtgtttgccg gtgccgtggc ccaggcctct ccccacggtc    13500
tgcagctggg ggtgcaggct gtggtctacc acggggcta tcttcccttt cgggaccca     13560 acagcgagga gaacagcaac gatattgccc tggtccacct ctccagtccc ctgcccctca    13620
caggtaagtc taagggctga gccatggggc ttgaggaccc gaggcagga ggacagagga     13680 ggggaccagg ggcacaaggc aatcaactta tggctcaggc atccttggca ataagggaa     13740 tgatctcgag ggagcacaaa gtgggcctta actatcaatg atcagtgcag ccaatttgga    13800
aaatttgcca gcatttcccc aagaagtata cataaagtta ccattggacc caacacttcc    13860
actcccagga caggaggtat ataccctaaga caaatggaaa ctgtgtctgc accaaaactc    13920
gtacatcagt gttcatagca gcattattca taatagccca aagatggaaa cagcccaaga    13980
gtgtttcatc ggacaaatgc ataaagaaaa tgtggtatat tgaccgggcg cggtggctca    14040
tgcctgtaat cccagcactt tgggaggccg aggtgggtgg atacacgagg tcaggagttt    14100
gaaaccagcc tggccaacat ggtgaaactc ctctctacta aaaatacaaa aattagnnnn    14160
nnnnnnnnnn nnnnnnnnnn nnnnnnnnnn nnnnnnnnnn nnnnnnnnnn nnnnnnnnnn    14220
```

| | |
|---|---|
| nnnnnnnnnn nnnnnnnnnn nnnnnnnnnn nnnnnnnnnn nnnnnnnnnn nnnnnnnnnn | 14280 |
| nnnnnnnnnn nnnnnnnnnn nnnnnnnnnn nnnnnnnnnn nnnnnnnnnn nnnnnnnnnn | 14340 |
| nnnnnnnnnn nnnnnnnnnn nnnnnnnnnn nnnnnnnnnn nnnnnnnnnn nnnnnnnnnn | 14400 |
| nnnnnnnnnn nnnnnnnnnn nnnnnnnnnn nnnnnnnnnn nnnnnnnnnn nnnnnnnnnn | 14460 |
| nnnnnnnnnn nnnnnnnnnn nnnnnnnnnn nnnnnnnnnn nnnnnnnnnn nnnnnnnnnn | 14520 |
| nnnnnnnnnn nnnnnnnnnn nnnnnnnnnn nnnnnnnnnn nnnnnnnnnn nnnnnnnnnn | 14580 |
| nnnnnnnnnn nnnnnnnnnn nnnnnnnnnn nnnnnnnnnn nnnnnnnnnn nnnnnnnnnn | 14640 |
| nnnnnnnnnn nnnnnnnnnn nnnnnnnnnn nnnnnnnnnn nnnnnnnnnn nnnnnnnnnn | 14700 |
| nnnnnnnnnn nnnnnnnnnn nnnnnnnnnn nnnnnnnnnn nnnnnnnnnn nnnnnnnnnn | 14760 |
| nnnnnnnnnn nnnnnnnnnn nnnnnnnnnn nnnnnnnnnn nnnnnnnnnn nnnnnnnnnn | 14820 |
| nnnnnnnnnn nnnnnnnnnn nnnnnnnnnn nnnnnnnnnn nnnnnnnnnn nnnnnnnnnn | 14880 |
| nnnnnnnnnn nnnnnnnnnn nnnnnnnnnn nnnnnnnnnn nnnnnnnnnn nnnnnnnnnn | 14940 |
| nnnnnnnnnn nnnnnnnnnn nnnnnnnnnn nnnnnnnnnn nnnnnnnnnn nnnnnnnnnn | 15000 |
| nnnnnnnnnn nnnnnnnnnn nnnnnnnnnn nnnnnnnnnn nnnnnnnnnn nnnnnnnnnn | 15060 |
| nnnnnnnnnn nnnnnnnnnn nnnnnnnnnn nnnnnnnnnn nnnnnnnnnn nnnnnnnnnn | 15120 |
| nnnnnnnnnn nnnnnnnnnn nnnnnnnnnn nnnnnnnnnn nnnnnnnnnn nnnnnnnnnn | 15180 |
| nnnnnnnnnn nnnnnnnnnn nnnnnnnnnn nnnnnnnnnn nnnnnnnnnn nnnnnnnnnn | 15240 |
| nnnnnnnnnn nnnnnnnnnn nnnnnnnnnn nnnnnnnnnn nnnnnnnnnn nnnnnnnnnn | 15300 |
| nnnnnnnnnn nnnnnnnnnn nnnnnnnnnn nnnnnnnnnn nnnnnnnnnn nnnnnnnnnn | 15360 |
| nnnnnnnnnn nnnnnnnnnn nnnnnnnnnn nnnnnnnnnn nnnnnnnnnn nnnnnnnnnn | 15420 |
| nnnnnnnnnn nnnnnnnnnn nnnnnnnnnn nnnnnnnnnn nnnnnnnnnn nnnnnnnnnn | 15480 |
| nnnnnnnnnn nnnnnnnnnn nnnnnnnnnn nnnnnnnnnn nnnnnnnnnn nnnnnnnnnn | 15540 |
| nnnnnnnnnn nnnnnnnnnn nnnnnnnnnn nnnnnnnnnn nnnnnnnnnn nnnnnnnnnn | 15600 |
| nnnnnnnnnn nnnnnnnnnn nnnnnnnnnn nnnnnnnnnn nnnnnnnnnn nnnnnnnnnn | 15660 |
| nnnnnnnnnn nnnnnnnnnn nnnnnnnnnn nnnnnnnnnn nnnnnnnnnn nnnnnnnnnn | 15720 |
| nnnnnnnnnn nnnnnnnnnn nnnnnnnnnn nnnnnnnnnn nnnnnnnnnn nnnnnnnnnn | 15780 |
| nnnnnnnnnn nnnnnnnnnn nnnnnnnnnn nnnnnnnnnn nnnnnnnnnn nnnnnnnnnn | 15840 |
| nnnnnnnnnn nnnnnnnnnn nnnnnnnnnn nnnnnnnnnn nnnnnnnnnn nnnnnnnnnn | 15900 |
| nnnnnnnnnn nnnnnnnnnn nnnnnnnnnn nnnnnnnnnn nnnnnnnnnn nnnnnnnnnn | 15960 |
| nnnnnnnnnn nnnnnnnnnn nnnnnnnnnn nnnnnnnnnn nnnnnnnnnn nnnnnnnnnn | 16020 |
| nnnnnnnnnn nnnnnnnnnn nnnnnnnnnn nnnnnnnnnn nnnnnnnnnn nnnnnnnnnn | 16080 |
| nnnnnnnnnn nnnnnnnnnn nnnnnnnnnn nnnnnnnnnn nnnnnnnnnn nnnnnnnnnn | 16140 |
| nnnnnnnnnn nnnnnnnnnn nnnnnnnnnn nnnnnnnnnn nnnnnnnnnn nnnnnnnnnn | 16200 |
| nnnnnnnnnn nnnnnnnnnn nnnnnnnnnn nnnnnnnnnn nnnnnnnnnn nnnnnnnnnn | 16260 |
| nnnnnnnnnn nnnnnnnnnn nnnnnnnnnn nnnnnnnnnn nnnnnnnnnn nnnnnnnnnn | 16320 |
| nnnnnnnnnn nnnnnnnnnn nnnnnnnnnn nnnnnnnnnn nnnnnnnnnn nnnnnnnnnn | 16380 |
| nnnnnnnnnn nnnnnnnnnn nnnnnnnnnn nnnnnnnnnn nnnnnnnnnn nnnnnnnnnn | 16440 |
| nnnnnnnnnn nnnnnnnnnn nnnnnnnnnn nnnnnnnnnn nnnnnnnnnn nnnnnnnnnn | 16500 |
| nnnnnnnnnn nnnnnnnnnn nnnnnnnnnn nnnnnnnnnn nnnnnnnnnn nnnnnnnnnn | 16560 |
| nnnnnnnnnn nnnnnnnnnn nnnnnnnnnn nnnnnnnnnn nnnnnnnnnn nnnnnnnnnn | 16620 |

```
nnnnnnnnnn nnnnnnnnnn nnnnnnnnnn nnnnnnnnnn nnnnnnnnnn nnnnnnnnnn    16680
nnnnnnnnnn nnnnnnnnnn nnnnnnnnnn nnnnnnnnnn nnnnnnnnnn nnnnnnnnnn    16740
nnnnnnnnnn nnnnnnnnnn nnnnnnnnnn nnnnnnnnnn nnnnnnnnnn nnnnnnnnnn    16800
nnnnnnnnnn nnnnnnnnnn nnnnnnnnnn nnnnnnnnnn nnnnnnnnnn nnnnnnnnnn    16860
nnnnnnnnnn nnnnnnnnnn nnnnnnttgc cacacccttc tccttagtga aaagtagtga    16920
gagagttaat attgaagtaa ggacgcatct ttgaggacag gtggacaggt ggaagcggct    16980
gggatttcag acacagggct gaggggtca cagcatgggc tttggggtca gattcagata    17040
tttgccaact gtgtgatctt ggacacatga cttcacctca ccgtgtctca gtttccctta    17100
tctgtaaaat gacttcctag ggttattgag acaattaaaa gggttaatat gagtaaagag    17160
cttagagaac tgccagcaca tagtgaacac tggtaaatgt tagcaattgc tactattgtt    17220
gtttaatact tttactagtt atatgaacac ttgctgtttg cctggcatgc aactcaatga    17280
ctcaccaatt tctcactaca acttctgggg ataagtgatt attatttcca ttctacatct    17340
gagagctcta agactcaggc aggtgatgtc atcagcaggc agcaggcaac aggcagggct    17400
gccaggaacc cttgcatagg ttgtgcactg cacaaggaca ccacatctca gggttaccac    17460
tctctctgta gacctgtgta tttattatta tgattttctg ccaggtggaa gtcaaatgtc    17520
tcaagatagg agtgtctctc tctctctctc tcttcttct ctctctctct ttcttttttt    17580
gagacagagt cttgctctgt cacccaggct ggagtgcaat ggcgcaatct cggctccctg    17640
caaactctgc ctcctaggtt caagcgattc tcctgcctca gcctcctgag tagctgggat    17700
tacaggcacc tgccatctgt aatcccagtg ctttgggagg ctgaggcagg aggattgctt    17760
gagcccagga ggccgaggct gcagtgagcc atgttcctgc cactgcactc tggcctgggt    17820
gacactgcag gcttagaaat gaaaacaagc tgtgttaaaa catacatgtt atgaaacttt    17880
ggacacgtga cttggcctca ttttccccct ctctaaaatg ggataatata gaccctacct    17940
ctctgggctg atgaaacatt aaagaaaatg gtgcaggaag gcgcctagta tgcgatgagc    18000
tcttggtacg tggcgacttc cgttgtggct ttttgtttg tttgtttgtt tttgagacag    18060
agtcttgctc tgtcgcccag gctggagtgc aatgacatga tctcggctca ctgcaacctc    18120
cacctcctgg gttcaagtga ttcttctgcc tcagtctccc gagtagctgg gattacaggt    18180
gcgtgccacc atgcccggct aattttgta ttttagtag agatgaggtt tcgccatgtt    18240
ggccaggctg gtctcaaact cctgacatca agtgatcctc ctgcctcggc ctcccaaagt    18300
gctggtatta caggcatgag ccactgtgcc cagcctattg tggttttttt tttaaagaac    18360
agagagggca gggtgtgtta ggggccatgg tagcagctgg acagaggttt gtaccaggtg    18420
gggcaggcca gcagggctg gaccagcatt gtctctctca cagaatacat ccagcctgtg    18480
tgcctcccag ctgccggcca ggccctggtg gatggcaaga tctgtaccgt gacgggctgg    18540
ggcaacacgc agtactatgg tgagtcctgt cctctgcctc tgatgccacc atttgggaga    18600
ctctgaactg ggctggggat gggcagtctg gctggttgga tgagtcttga ccatgaggag    18660
tagggatgct gaggggaatg gggtgggcac caggagggaa gggggggtgtg tacaccccc    18720 agctctggcc agccttgcct gcacaccccc aggccaacag gccggggtac tccaggaggc    18780
tcgagtcccc ataatcagca atgatgtctg caatggcgct gacttctatg gaaaccagat    18840
caagcccaag atgttctgtg ctggctaccc cgagggtggc attgatgcct gccaggtgag    18900
ggactctgta ggggcagccc cctggtcgct gccaccccag ggatggagac gcaggggagt    18960
```

```
gggtggtcgg gctccccatc taaaagcctg agggctctgg ggccacagcc catgtcatcc   19020 cggggggggcc tcctgtctaa ccactttggc ctccagccag acctccctct cccctcccag   19080
ggcgacagcg gtggtccctt tgtgtgtgag gacagcatct ctcggacgcc acgttggcgg   19140
ctgtgtggca ttgtgagttg gggcactggc tgtgccctgg cccagaagcc aggcgtctac   19200
accaaagtca gtgacttccg ggagtggatc ttccaggcca taaaggtgaa agttgggtcc   19260
agatgggagc cagggtgggg acgtttggt gtctaatggg ggaagggagg cagagatttg   19320
ttttaggaaa cctacgctca ggcctagaag agggcccccc ttgggaacag atggactttg   19380
aagggttcct ggggaaggga agccagtggt gggacgtgga agcctctcag acctcgggag   19440
cccccagctg tctttcccca gactcactcc gaagccagcg gcatggtgac ccagctctga   19500
ccggtggctt ctcgctgcgc agcctccagg gcccgaggtg atcccggtgg tgggatccac   19560
gctgggccga ggatgggacg ttttttcttct tgggcccggt ccacaggtcc aaggacaccc   19620
tccctccagg gtcctctctt ccacagtggc gggcccactc agccccgaga ccacccaacc   19680
tcaccctcct gacccccatg taaatattgt tctgctgtct gggactcctg tctaggtgcc   19740
cctgatgatg ggatgctctt taaataataa agatggtttt gattaatgtg gcctccgagc   19800
ttacaaatgt acacagcaat gaggacattt tgtcaggaag gaagagaaga attaggacct   19860
ggcgcaaatc agacagagag tgtgggtccc tcagttccca ctgatttgag atttaagatt   19920
ttaattggtt cacttaactg gaattttcct ggagcaaatt ggcttcaggt acagctggat   19980
ccagctgctc tctcaaatct gccttaggct gtgttagctt catttccaag cagcctctcc   20040
tacaaccaga gagagagatg tccccttcca cacaaactct ttcccaatca ctgcagaaaa   20100
agacccaggc aacaacaaca acaaaaaccc aggcccagct cccattgtac agatttgggt   20160
cacgtgctca tcccttggca aatcactgtg caccggatgt acgcggtagg ggtggagcgg   20220
ggtggagtgg gaggagctag gccttcaaga atcgtgtgac ctgagtgtgg gagtcccaaa   20280
ggaaataggg tgctatttcc agaagtggaa atagatgctc agtgagcaaa aaagacatct   20340
accttgaacc aacacggaaa acggggcccct gtaaggtgga gatagggaga cgctgggaac   20400
acagcctgag accctccccc aacccctttc tccatctggg cagcttctgg ggaggaaccc   20460
ccttctgtag agcctctgca gagcctcatg cagccccgat ggccaccagg gggcactgct   20520 gcccccaacat tgtgacacat taagggtttt cctgcctgga gtcagccgca tgttgctgaa   20580
aacctgctgt tctgctgaag aaaggctcag cggggggagcc tgttcaccat gactttaaat   20640
aataacaatt atcatacatc acccatggac cacagcttcc aagcaatttc cttttttttt   20700
tttttttttt ttttttgaga cagagtttca ctcttgtctc ccaggttgga gtgcagtggc   20760
gtgatcttag ctcactacaa cctccgcctc ctgggttcaa gcgattctcc tgcctcggcc   20820
tcccgagtag ctgggattac aggcgtgccc caccacgccc agctgatttt tgtattttta   20880
gtagagacgg gctgtcacca tgttggccag gctgctctcg aactcctgac ctcaggtgat   20940
ccacctgcct cggcctccca aagtgctggg tgtcacgcgc atccatgtga agagaccacc   21000
aaacaggctt tgtgtgagca ataaagcttt ctaatcacct gggtgcaggc aggctgagtc   21060
cgaaaagaga gtcagtgaag ggaggtaggg gtgggccgt tttatgggat ttggataggt   21120
agtggaaaat tacagtcaaa gggggttgtt ctctggcggg caggggtggg ggtcacaagg   21180
tgctcagtgg gggagcttct gagccaggag aaggaatttc acaaggtaat gtcatcagtt   21240
aaggcaggaa ccggccatttt tcacttcttt tgtgattctt cagttacttc aggccatctg   21300
gatgtataca tgcaggcttg ggctcagagg cctgacactg ggattacaga tgtctgctgc   21360
```

-continued

```
cacacctggc taattttgt attttagta gagacgggtt tcaccatgtt ggcaggctgg  21420
tctcgaactc ctgacctcag gtgatccgcc caccttggcc tcccaaagtg ctgggattac  21480
aagcctaagc cactgcaccc agcccagctt cctaaaatat agatgatcta caagagctcc  21540
tttgagaaac tgacaaactg tgcatttgga aaacgatccc agcgtcactc cccgatcccc  21600
acacccctgg cgaggttgag ccccaccact gctttgttgg tcaggagccc ccaggcccac  21660
atcgtgttag cagagcctca gtgcagtttc cccaaacgtc tacctctggc tgtggtgttc  21720
tacccatggc atgtgggatg taatttgaga cctgacctac ggcttgcttt gttagaaacg  21780
tatt                                                              21784
```

<210> SEQ ID NO 4
<211> LENGTH: 417
<212> TYPE: PRT
<213> ORGANISM: HUMAN

<400> SEQUENCE: 4

```
Met Ala Gln Lys Glu Gly Gly Arg Thr Val Pro Cys Cys Ser Arg Pro
 1               5                  10                  15

Lys Val Ala Ala Leu Thr Ala Gly Thr Leu Leu Leu Thr Ala Ile
            20                  25                  30

Gly Ala Ala Ser Trp Ala Ile Val Ala Val Leu Leu Arg Ser Asp Gln
        35                  40                  45

Glu Pro Leu Tyr Pro Val Gln Val Ser Ser Ala Asp Ala Arg Leu Met
    50                  55                  60

Val Phe Asp Lys Thr Glu Gly Thr Trp Arg Leu Leu Cys Ser Ser Arg
65                  70                  75                  80

Ser Asn Ala Arg Val Ala Gly Leu Ser Cys Glu Glu Met Gly Phe Leu
                85                  90                  95

Arg Ala Leu Thr His Ser Glu Leu Asp Val Arg Thr Ala Gly Ala Asn
            100                 105                 110

Gly Thr Ser Gly Phe Phe Cys Val Asp Glu Gly Arg Leu Pro His Thr
        115                 120                 125

Gln Arg Leu Leu Glu Val Ile Ser Pro Ser Asp Cys Pro Arg Gly Arg
    130                 135                 140

Phe Leu Ala Ala Ile Cys Gln Asp Cys Gly Arg Arg Lys Leu Pro Val
145                 150                 155                 160

Asp Arg Ile Val Gly Gly Arg Asp Thr Ser Leu Gly Arg Trp Pro Trp
                165                 170                 175

Gln Val Ser Leu Arg Tyr Asp Gly Ala His Leu Cys Gly Gly Ser Leu
            180                 185                 190

Leu Ser Gly Asp Trp Val Leu Thr Ala Ala His Cys Phe Pro Glu Arg
        195                 200                 205

Asn Arg Val Leu Ser Arg Trp Arg Val Phe Ala Gly Ala Val Ala Gln
    210                 215                 220

Ala Ser Pro His Gly Leu Gln Leu Gly Val Gln Ala Val Val Tyr His
225                 230                 235                 240

Gly Gly Tyr Leu Pro Phe Arg Asp Pro Asn Ser Glu Glu Asn Ser Asn
                245                 250                 255

Asp Ile Ala Leu Val His Leu Ser Ser Pro Leu Pro Leu Thr Glu Tyr
            260                 265                 270

Ile Gln Pro Val Cys Leu Pro Ala Ala Gly Gln Ala Leu Val Asp Gly
        275                 280                 285
```

```
Lys Ile Cys Thr Val Thr Gly Trp Gly Asn Thr Gln Tyr Tyr Gly Gln
        290                 295                 300

Gln Ala Gly Val Leu Gln Glu Ala Arg Val Pro Ile Ile Ser Asn Asp
305                 310                 315                 320

Val Cys Asn Gly Ala Asp Phe Tyr Gly Asn Gln Ile Lys Pro Lys Met
                325                 330                 335

Phe Cys Ala Gly Tyr Pro Glu Gly Gly Ile Asp Ala Cys Gln Gly Asp
            340                 345                 350

Ser Gly Gly Pro Phe Val Cys Glu Asp Ser Ile Ser Arg Thr Pro Arg
        355                 360                 365

Trp Arg Leu Cys Gly Ile Val Ser Trp Gly Thr Gly Cys Ala Leu Ala
370                 375                 380

Gln Lys Pro Gly Val Tyr Thr Lys Val Ser Asp Phe Arg Glu Trp Ile
385                 390                 395                 400

Phe Gln Ala Ile Lys Thr His Ser Glu Ala Ser Gly Met Val Thr Gln
                405                 410                 415

Leu
```

<210> SEQ ID NO 5
<211> LENGTH: 601
<212> TYPE: DNA
<213> ORGANISM: HUMAN

<400> SEQUENCE: 5

```
aaaaggctgt gcagtacttg cctcttagcc agcacagtgg acattggctt ttgtatctca   60
ctcctgaaat tctttcttga aatttcttga gcaagatctt cctggacttc agactctat  120
ggcctctcac cctatggtgt gtccctgcca ccccggtaaa accctcctca ctcattgtga  180
attatttact cctggcgaac tccaggaagg cagggacctt tgtggtcag acggtgcctg  240
gcacatagta ggttctcagg aaatccttga gttatgagtg cacccaaagc caaaacactg  300
rgatgaacta gagagtcatg gcctccagc tggaaaggag cgaggccacc actcacaacc  360
ggctctggcc agcaccacgc cgccaccctg cagaggtatt tgggttttc aacaactcag  420
ggaaatgatg aaacaaacaa acaaacaaaa acaaccccaa gcttgtatcc ccacctcgct  480
tttttttttcc tgggattttc acacttctaa atatatccaa caacttggca ggcacaccag  540
gtgacccaga acatcctttt tgtgttgcct gaaatgatag gaacaagaat aaagaattta  600
a                                                                  601
```

<210> SEQ ID NO 6
<211> LENGTH: 601
<212> TYPE: DNA
<213> ORGANISM: HUMAN

<400> SEQUENCE: 6

```
tcactcctga aattctttct tgaaatttct tgagcaagat cttcctggac ttccagactc   60
tatggcctct caccctatgg tgtgtccctg ccaccccggt aaaaccctcc tcactcattg  120
tgaattattt actcctggcg aactccagga aggcagggac cttttgtggt cagacggtgc  180
ctggcacata gtaggttctc aggaaatcct tgagttatga gtgcacccaa agccaaaaca  240
ctgggatgaa ctagagagtc atgggcctcc agctggaaag gagcgaggcc accactcaca  300
mccggctctg gccagcacca cgccgccacc ctgcagaggt atttgggttt tcaacaact   360
cagggaaatg atgaaacaaa caaacaaaca aaaacaaccc caagcttgta tccccacctc  420
gcttttttttt tcctgggatt ttcacacttc taaatatatc caacaacttg gcaggcacac  480
```

```
caggtgaccc agaacatcct ttttgtgttg cctgaaatga taggaacaag aataaagaat        540
ttaaaagtga gaaacagcag cagagagtgt gactttaaaa atagccagag gggacatttg        600
a                                                                        601

<210> SEQ ID NO 7
<211> LENGTH: 601
<212> TYPE: DNA
<213> ORGANISM: HUMAN

<400> SEQUENCE: 7
atagaataaa ataaaataag aatccgcccc cctccccgcc ccagttggtg tttcaaaccc         60
tgagacttgg ccttggaatt catggggtga tgaggacccc acagccagag gtgccaggcg        120
ttccctgccc aacccccaga gcaggaggcc atcattaagg caggccagcc aggtggcttt        180
tcagtgccag ccgtagctga atatattagg caggagacag gcaagggtt tgtatgagac         240
ccacagaagg aacagggaat atgctggtct gggttcaagt cccggttttg ctggttagcc        300
rtgtgcctct gggcaagttt attcctctga ggcttagttt tcccatctgt aagatgggca        360
tagaagtggt cactactggc tgggcacagt ggctcacgcc tgtaatccca gcacttgggg        420
aggccaaggc agtggatca cctgaggcca aagttcgag accagcctgg ccaacatggt         480
gaaacgctgt ttctactaag aacacaaaag ttagccaggt gtagtagcat gtgcctgtaa        540
tcccagctac tcgggaggct gaggcaggag gatcgcttga acctgggagg cagaggttgc        600
a                                                                        601

<210> SEQ ID NO 8
<211> LENGTH: 601
<212> TYPE: DNA
<213> ORGANISM: HUMAN

<400> SEQUENCE: 8
agtttattcc tctgaggctt agttttccca tctgtaagat gggcatagaa gtggtcacta         60
ctggctgggc acagtggctc acgcctgtaa tcccagcact ggggaggcc aaggcaggtg        120
gatcacctga ggccagaagt tcgagaccag cctggccaac atggtgaaac gctgtttcta        180
ctaagaaacac aaaagttagc caggtgtagt agcatgtgcc tgtaatccca gctactcggg        240
aggctgaggc aggaggatcg cttgaacctg ggaggcagag gttgcagtga gccgagatca        300
ygccactgca ctccagcctg agcaacagag caagattatg tctcaaaaaa aaaaaaaaa        360
accgaagtgg tcactatctc cgaggatggt tgtgggattc agagagccac ttggatagga        420
tgcatagcat ggggccagcc cactgacacc ccccagtaaa cgtagccagt gctattatta        480
ctgtgctgtt gtttaaccct ccagagggga agtctcttga gaggctgtcc agggcaatgt        540
taaaagcttg gggtttgaag tcactcagac ctgatttcga atcctctctc cctgcttctc        600
g                                                                        601

<210> SEQ ID NO 9
<211> LENGTH: 601
<212> TYPE: DNA
<213> ORGANISM: HUMAN

<400> SEQUENCE: 9
cctggctgca cctcacacca ggtgccagca aagccctgat gttgctctat ttctagctcc         60
cacctgatct gcccctccct ggctcactct gctctggcct cccactgttc ctggagcact        120
```

```
cccccagtc ccccacacca gccttgggat ctttgcatct gcaagtccct ctgtctccgt    180
gctgatctca cacacctcct gacactttct cacctcctgc aggtctttgt tcctgcacca    240
ccttcccagg gacgctctcc ttgcagcgac tgaaaagtgc aacctcaccc caccctccac    300
rccggcactc ccctccctcg gtggcatttt attttctct gtggcccctt cctatcttgt     360
gacacataat atatcctact tatttgtccc tttcttgatt tgtctcacct actgagcttt    420
gagttccaca ggggtcgggg ttttttgtctg atttgttcat tgcagtggtg atttgttcac  480
tgcctaaaat agagcctggc aggtacaaag tgtttggtaa atagaaatca ataccccagg   540
gtctgtgacc tgacttaggt gttaacaggt tcctctgagg tgtgtgggga acagactgag   600
g                                                                   601
```

<210> SEQ ID NO 10
<211> LENGTH: 601
<212> TYPE: DNA
<213> ORGANISM: HUMAN

<400> SEQUENCE: 10

```
gtatatccca gccctgcctc atgtcacaat ttgtaatgat gtgtttggct gggtgacatt     60
ttatggccat ctgtctccct atcccctata atgtggtttg ccgaaagcaa agcccaggac    120
tgtctcggcc atctgtgtct ccaggatcac ccctcactgg gcatgagta tgtgtccagt    180 taacgcttgc tgagtgaatg aatgaatact ccatcctctg cctggagaat tacgcacttt    240
agcatatcca aggctctgac aagtcctgca taaagagca ttattgtttt ctttctttct    300
ttccttcttt ccctcttctt ttctttctga ctataggata ttgattatca atctggcaat    360
agtcaagatt ggcagtctgg tgtattagtc aaaggttttc agcctacaaa agacaaaaag   420
aaaaaataaa ctggctaaaa acaaaagggg atatgattta ctaactcact taaccgacag   480
tcacagaggt tcttcaaacc tggctgtatc aagggctttt aaaatgttat cagatggggg   540
ccaggtgcag tagctcacgc ctgtcatcca gcactttggg aggccaagac aggcagatca   600
c                                                                   601
```

<210> SEQ ID NO 11
<211> LENGTH: 601
<212> TYPE: DNA
<213> ORGANISM: HUMAN

<400> SEQUENCE: 11

```
tatcccagcc ctgcctcatg tcacaatttg taatgatgtg tttggctggg tgacatttta     60
tggccatctg tctccctatc cctataatg tggtttgccg aaagcaaagc ccaggactgt    120
ctcggccatc tgtgtctcca ggatcacccc tcactgggca tgagtatgt gtccagttaa    180 cgcttgctga gtgaatgaat gaatactcca tcctctgcct ggagaattac gcactttagc   240
atatccaagg ctctgacaag tcctgcataa agagcatta ttgttttctt tctttctttc    300
cttctttccc tcttcttttc tttctgacta taggatattg attatcaatc tggcaatagt   360
caagattggc agtctggtgt attagtcaaa ggttttcagc ctacaaaaga caaaagaaa    420 aaataaactg gctaaaaaca aaaggggata tgatttacta actcacttaa ccgacagtca   480
cagaggttct tcaaacctgg ctgtatcaag ggctttaaa atgttatcag atggggggcca  540 ggtgcagtag ctcacgcctg tcatccagca ctttgggagg ccaagacagg cagatcactt   600
g                                                                   601
```

<210> SEQ ID NO 12
<211> LENGTH: 601
<212> TYPE: DNA
<213> ORGANISM: HUMAN

<400> SEQUENCE: 12

| | | | | | |
|---|---|---|---|---|---|
| tccagttaac | gcttgctgag | tgaatgaatg | aatactccat | cctctgcctg | gagaattacg | 60 |
| cactttagca | tatccaaggc | tctgacaagt | cctgcataaa | agagcattat | tgttttcttt | 120 |
| ctttctttcc | ttctttccct | cttcttttct | ttctgactat | aggatattga | ttatcaatct | 180 |
| ggcaatagtc | aagattggca | gtctggtgta | ttagtcaaag | gttttcagcc | tacaaaagac | 240 |
| aaaagaaaa | aataaactgg | ctaaaaacaa | aaggggatat | gatttactaa | ctcacttaac | 300 |
| sgacagtcac | agaggttctt | caaacctggc | tgtatcaagg | gctttaaaa | tgttatcaga | 360 |
| tgggggccag | gtgcagtagc | tcacgcctgt | catccagcac | tttgggaggc | caagacaggc | 420 |
| agatcacttg | aggtcaggag | ttcgagacca | gcctggccaa | catggtgaaa | ccccgtgtct | 480 |
| actaaaaata | caaaaaatta | gccaagtgtg | gtggcatgtg | tctgtagctc | cagctactcg | 540 |
| ggaggctgag | gcaggacaat | ggcttgaatc | cgggaggcgg | aggttacagt | gacccaaggt | 600 |
| t | | | | | | 601 |

<210> SEQ ID NO 13
<211> LENGTH: 601
<212> TYPE: DNA
<213> ORGANISM: HUMAN

<400> SEQUENCE: 13

| | | | | | |
|---|---|---|---|---|---|
| tagttttcat | agagacgagg | tttcatcatc | ttggccaggc | tggtcttgaa | ctcctgacct | 60 |
| tgtgatccac | ccatctcggc | ctcccaaata | aatacatatt | ttaaaagata | gaaatcactc | 120 |
| tggaaggaga | gttaatctgt | ttgatataat | aataatatat | taatattata | ttataacaat | 180 |
| atattagtat | tatattctaa | taatatatta | atatttatatt | ataataatat | attattatat | 240 |
| tataacaata | tattaatatt | atattataac | aatatattaa | tattatatta | tgtaataata | 300 |
| mtactactcc | atatagctat | ggaaaagttc | atatgaagaa | accaggctat | gatctacaaa | 360 |
| ctggcaacaa | atttgttctt | ctattttcca | tatgctgtct | gtgtacgtat | aaagtgagag | 420 |
| gtcttttttat | atgagttaag | ggtgtgacca | agacaaatg | gaaaagaca | aatgacaaac | 480 |
| atactaataa | agagcttcgg | tttctccaca | aaaaatacaa | taataaaata | aaatgttatc | 540 |
| agaaatctct | tgactctcct | ccacgttagc | tcacttttc | cctcaagagg | gtgaacatga | 600 |
| c | | | | | | 601 |

<210> SEQ ID NO 14
<211> LENGTH: 601
<212> TYPE: DNA
<213> ORGANISM: HUMAN

<400> SEQUENCE: 14

| | | | | | |
|---|---|---|---|---|---|
| cacctcagac | ccccaaggca | ctccctctcc | ccgttttcct | tccacctgtc | ttaactggtc | 60 |
| tctatttcct | ttcttctgt | gtctccaatc | ccatctctcc | cagtgattgc | cccagaggcc | 120 |
| gtttcttggc | cgccatctgc | caaggtgaga | tcctaaaact | cagaaccctc | tcctttaggc | 180 |
| ccttggggag | gccacgtccc | ctcaagctcc | ccaggatggg | gccatgtact | ttcagacccc | 240 |
| ctagggcagg | gccaagcctg | ggctctgggg | acctggctc | cagtcccctg | tcgccgcccc | 300 |
| ctgctgaccc | ttgtcccaca | gactgtggcc | gcaggaagct | gcccgtggac | cgcatcgtgg | 360 |

-continued

```
gaggccggga caccagcttg ggccggtggc cgtggcaagt cagccttcgc tatgatggag    420
cacacctctg tgggggatcc ctgctctccg gggactgggt gctgacagcc gcccactgct    480
tcccggagtg agtgccccc aatggcgctg atgatgggga ggcagaggag cggagagaca    540
gtggggagga gggcggattg tgcccaggca ggtggccacc ctccacccct ttccctggta    600
g                                                                    601

<210> SEQ ID NO 15
<211> LENGTH: 601
<212> TYPE: DNA
<213> ORGANISM: HUMAN

<400> SEQUENCE: 15
gcaagtcagc cttcgctatg atggagcaca cctctgtggg ggatccctgc tctccgggga     60
ctgggtgctg acagccgccc actgcttccc ggagtgagtg cccccaatg gcgctgatga    120
tggggaggca gaggagcgga gagacagtgg ggaggagggc ggattgtgcc caggcaggtg    180
gccaccctcc acccctttcc ctggtaggcg aaccgggtc ctgtcccgat ggcgagtgtt    240
tgccggtgcc gtgcccagg cctctcccca cggtctgcag ctgggggtgc aggctgtggt    300
ytaccacggg ggctatcttc cctttcggga ccccaacagc gaggagaaca gcaacgatat    360
tgccctggtc cacctctcca gtcccctgcc cctcacaggt aagtctaagg gctgagccat    420
ggggcttgag gacccgaggc caggaggaca gaggagggga ccaggggcac aaggcaatca    480
acttatggct caggcatcct tggcaataag gggaatgatc tcgagggagc acaaagtggg    540
ccttaactat caatgatcag tgcagccaat ttggaaaatt tgccagcatt tccccaagaa    600
g                                                                    601

<210> SEQ ID NO 16
<211> LENGTH: 601
<212> TYPE: DNA
<213> ORGANISM: HUMAN

<400> SEQUENCE: 16
ccctttccct ggtaggcgga accgggtcct gtcccgatgg cgagtgtttg ccggtgccgt     60
ggcccaggcc tctccccacg gtctgcagct gggggtgcag ctgtggtct accacggggg    120
ctatcttccc tttcgggacc ccaacagcga ggagaacagc aacgatattg ccctggtcca    180
cctctccagt cccctgcccc tcacaggtaa gtctaagggc tgagccatgg ggcttgagga    240
cccgaggcca ggaggacaga ggaggggacc aggggcacaa ggcaatcaac ttatggctca    300
kgcatccttg gcaataaggg gaatgatctc gagggagcac aaagtgggcc ttaactatca    360
atgatcagtg cagccaattt ggaaaatttg ccagcatttc cccaagaagt atacataaag    420
ttaccattgg acccaacact tccactccca ggacaggagg tatataccta agacaaatgg    480
aaactgtgtc tgcaccaaaa ctcgtacatc agtgttcata gcagcattat tcataatagc    540
ccaaagatgg aaacagccca agagtgtttc atcggacaaa tgcataaaga aaatgtggta    600
t                                                                    601
```